United States Patent [19]

Waddell et al.

[11] Patent Number: 5,332,807
[45] Date of Patent: Jul. 26, 1994

[54] PROCESS OF PRODUCING 8A- AND 9A-AZALIDE ANTIBIOTICS

[75] Inventors: Sherman T. Waddell, Westfield; Timothy A. Blizzard, Rahway, both of N.J.

[73] Assignee: Merck & Co., Inc., Rahway, N.J.

[21] Appl. No.: 48,048

[22] Filed: Apr. 14, 1993 (Under 37 CFR 1.47)

[51] Int. Cl.$^5$ .................. C07D 273/01; C07H 17/08
[52] U.S. Cl. ................. 536/7.4; 540/463; 540/467
[58] Field of Search .......... 540/463, 467; 536/7.4

[56] References Cited

U.S. PATENT DOCUMENTS

| | | | |
|---|---|---|---|
| 3,869,444 | 3/1975 | Freiberg | 536/7.4 |
| 3,979,511 | 9/1976 | Hung et al. | 514/29 |
| 4,152,424 | 5/1979 | Kierstead et al. | 424/120 |
| 4,328,334 | 5/1982 | Kobrehel et al. | 536/7.4 |
| 4,349,545 | 7/1982 | Gouin d/Ambrieres et al. | 514/29 |
| 4,464,527 | 8/1984 | Bright et al. | 536/7.4 |
| 4,465,674 | 8/1985 | Bright et al. | 514/29 |
| 4,492,688 | 1/1985 | Bright et al. | 536/7.2 |
| 4,512,982 | 4/1985 | Hauske et al. | 514/29 |
| 4,517,359 | 5/1985 | Kobrehel et al. | 536/7.4 |
| 4,518,590 | 5/1985 | Hauske et al. | 514/29 |
| 4,526,889 | 7/1985 | Bright | 514/29 |
| 4,680,386 | 7/1987 | Morimoto et al. | 536/7.4 |
| 4,886,792 | 12/1989 | Djokic | 514/183 |
| 4,921,839 | 5/1990 | Brain et al. | 514/29 |
| 4,957,905 | 9/1990 | Hunt et al. | 514/29 |
| 4,990,602 | 2/1991 | Morimoto | 536/7.4 |

FOREIGN PATENT DOCUMENTS

| | | |
|---|---|---|
| 0101186 | 2/1984 | European Pat. Off. |
| 0109253 | 5/1984 | European Pat. Off. |
| 0136831 | 4/1985 | European Pat. Off. |
| 0259789 | 3/1986 | European Pat. Off. |
| 0283055 | 9/1988 | European Pat. Off. |
| 0307128 | 5/1989 | European Pat. Off. |
| 0316128 | 5/1989 | European Pat. Off. |
| 0298650 | 11/1989 | European Pat. Off. |
| 0342990 | 11/1989 | European Pat. Off. |

OTHER PUBLICATIONS

Djokic, et al., *Erythromycin Series 12: Antibacterial in Vitro Evaluation of 10-Dehydro-11-deoxo-11-azaerythromycin A*, Journal of Antibiotics, vol. 40, No. 7, (Jul. 1987).

Djokic, et al., *Erythromycin Series Part II: Ring Expansion of Erythromycin A Oxime by the Beckman Rearrangement*, J. Chem. Soc., Perkins Trans. 1, pp. 1881-1890 (1986).

Djokic, et al., *Erythromycin Series Part 13: Synthesis and Structure Elucidation of 10-Dihydro-1-Deoxo-11-methyl-11-aza erythromycin A*, J. Chem. Research (S), pp. 152-153 (1988).

Bright, et al., *Sythesis, In Vitro and In Vivo Activity of Novel 9-Deoxo-9-a-Aza-9a-Homoerythromycin A Derivatives*, The Journal of Antibiotics, vol. 61, No. 8, pp. 1029-1047 (1988).

Massey, et al., *Erythromycylamine*, Tetrahedron Letters, No. 2, pp. 157-160 (1970).

Gasc et al., *New Ether Oxime Derivatives of Erythromycin A*, The Journal of Antibiotics, vol. 44, No. 3, pp. 313-329 (1990).

Thornsberry et al., *The Macrolide Revival: 35 Years After Erythromycin*, Antimicrobic Newsletter, vol. 4, No. 4, pp. 25-36 (1987).

Egan, et al., *Configuration of 9-Imino Derivatives of Erythromycin*, J. Org. Chem., vol. 39, pp. 2492-2494, (1974).

Jones, Brian A., J. Org. Chem., (1992) 57(16) 4361-4367.

Primary Examiner—Mukund J. Shah
Assistant Examiner—Matthew V. Grumbling
Attorney, Agent, or Firm—Richard C. Billups; Mark R. Daniel

[57] ABSTRACT

A process of producing 8a- and 9a- azalide compounds is disclosed, comprised of reacting an 8a- aza or 9a- aza azalide eastern fragment or a derivative thereof with a compound of the formula:

$$X-A'-Y$$

wherein X and Y are appropriate reactive groups and A' is a fragment or compound which forms the western portion of the azalide, and cyclizing this intermediate to form the target 8a- or 9a-azalide compound. Compounds of formula I, II and III as well as other azalides can be synthesized according to this process.

9 Claims, No Drawings

PROCESS OF PRODUCING 8A- AND 9A-AZALIDE ANTIBIOTICS

BACKGROUND OF THE INVENTION

The present invention is drawn to a process of producing azalide antibiotics which are useful in the therapy of bacterial infections in mammals.

Modifications of the western fragment of erythromycin A have been difficult to obtain. There is a long felt need for new azalide antibiotics, and in particular, for a process of varying the western fragment of such azalides. The invention thus provides a process of making azalide compounds with modified western fragments.

Erythromycin A has been the subject of investigation for many years. Erythromycin A has the following structural formula:

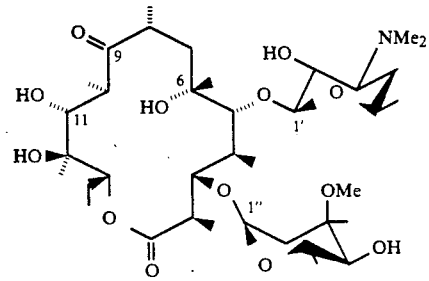

Reactions can be conducted which lead to rupture of the ring and formation of the $C_1$ carboxylate. This reaction can generally be conducted as follows:

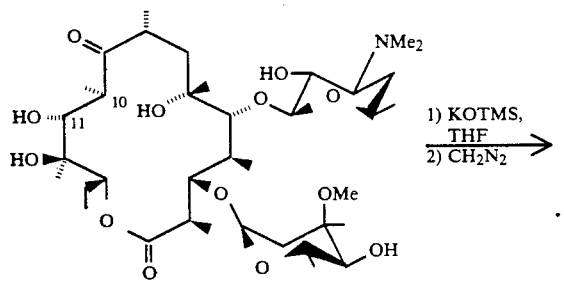

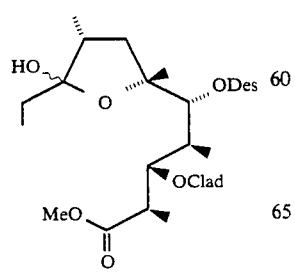

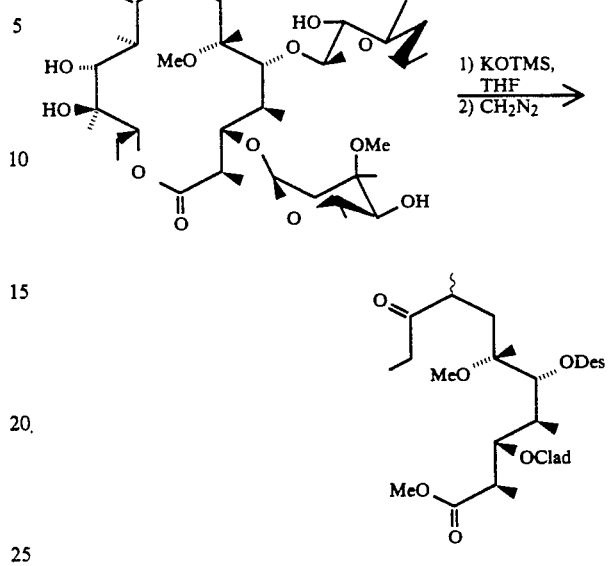

The present invention utilizes the fragments above, as well as other eastern fragments to produce novel 8a- and 9a- azalides. By modifying these fragments to produce 8a- and 9a- aza fragments, and combining the modified eastern fragments or derivatives thereof with an appropriate compound which forms the western portion of the molecule, the azalide ring structure can be formed. Thus, a large number of azalides can now be produced with modifications in the western portion of the molecule.

SUMMARY OF THE INVENTION

A process of producing 8a- and 9a- azalide compounds is disclosed, comprised of reacting an 8a- aza or 9a- aza azalide eastern fragment or a derivative thereof with a compound of the formula:

$$X-A'-Y$$

wherein X and Y are appropriate reactive groups and A' is a compound which forms the western portion of the azalide, and cyclizing this intermediate to form the target 8a- or 9a-azalide compound. Compounds of formula I, II and III as well as other azalides can be synthesized according to this process.

Compounds of formula I are represented by the formula:

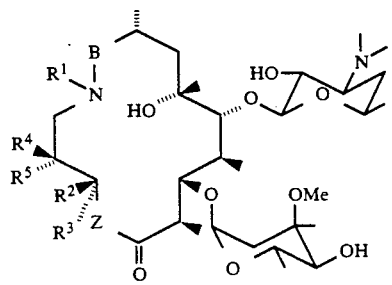

I $R^1$ represents hydrogen, $C_1$ to $C_7$ alkyl, arylsulfonyl or aralkyl, said alkyl, arylsulfonyl or aralkyl groups being unsubstituted or substituted with fluoro, alkyl or $R^{10}O$.

One of $R^2$ and $R^3$ represents hydrogen and the other represents hydrogen, $C_1$ to $C_7$ alkyl, cycloalkyl, aryl or aralkyl, said groups other than hydrogen being unsubstituted or substituted with $R^{10}O$, $R^{11}R^{12}N$, azide, alkyl, cycloalkyl or F.

$R^4$ and $R^5$ are independently hydrogen, $C_1$ to $C_7$ alkyl, fluoroalkyl, cycloalkyl, aryl, aralkyl, $R^{10}O$, $R^{11}R^{12}N$, azide or F.

In $OR^{10}$, $R^{10}$ represents hydrogen, $C_1$ to $C_7$ alkyl, fluoroalkyl, cycloalkyl, aryl or aralkyl.

$R^{11}$ represents hydrogen, $C_1$ to $C_7$ alkyl, fluoroalkyl, cycloalkyl, aryl or aralkyl.

$R^{12}$ represents hydrogen, $C_1$ to $C_7$ alkyl, fluoroalkyl, cycloalkyl, aryl, aralkyl or arylsulfonyl.

Z represents O or $NR^1$, and

B represents $C^*HCH_2CH_3$, the asymmetric carbon atom * of which is in the (R) or (S) stereoconfiguration, or a bond between the carbon and nitrogen atoms to which B is attached.

Compounds of formula II are represented by the formula:

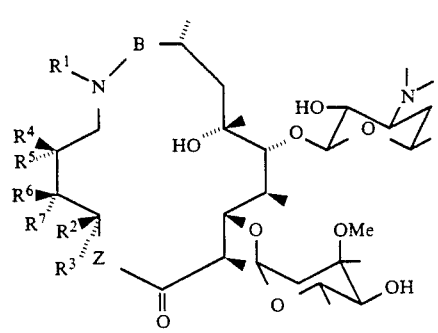

II $R^1$ represents hydrogen, $C_1$ to $C_7$ alkyl, arylsulfonyl or aralkyl, said alkyl, arylsulfonyl and aralkyl groups being unsubstituted or substituted with fluoro, alkyl or $R^{10}O$.

$R^2$ and $R^3$ independently represent hydrogen, $C_1$ to $C_7$ alkyl, cycloalkyl, aryl or aralkyl, said groups other than hydrogen being unsubstituted or substituted with $R^{10}O$, $R^{11}R^{12}N$, azide, alkyl, cycloalkyl or F.

$R^4$, $R^5$, $R^6$ and $R^7$ independently represent hydrogen, $C_1$ to $C_7$ alkyl, fluoroalkyl, cycloalkyl, aryl, aralkyl, $R^{10}O$, $R^{11}R^{12}N$, azide or F, or one of the pair $R^4$ and $R^6$, $R^4$ and $R^7$, $R^5$ and $R^6$, and $R^5$ and $R^7$ may be taken to represent cyclic carbonate (—OC(O)O—), cyclic acetonide ($OC(CH_3)_2O$), or a $C_1$ to $C_5$ alkanediyl group which forms a ring with the carbon atoms to which they are attached, said alkanediyl group being unsubstituted or substituted with $C_1$ to $C_7$ alkyl, fluoroalkyl, cycloalkyl, aryl, aralkyl, $R^{10}O$, $R^{11}R^{12}N$, azide or F.

$R^{10}$ represents hydrogen, $C_1$ to $C_7$ alkyl, fluoroalkyl, cycloalkyl, aryl or aralkyl.

Z represents O or $NR^1$, and

B represents $C^*HCH_2CH_3$, the asymmetric carbon atom * of which is in the (R) or (S) stereoconfiguration, or a bond between the carbon and nitrogen atoms to which B is attached.

Compounds of formula III are represented by the formula:

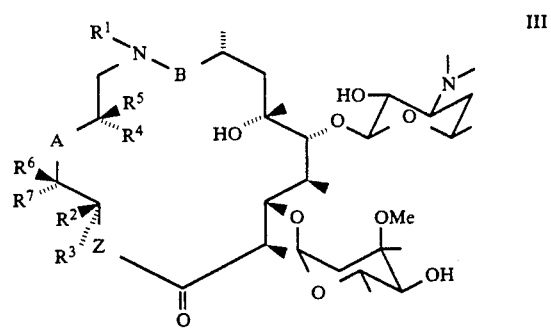

III $R^1$ represents hydrogen, $C_1$ to $C_7$ alkyl, arylsulfonyl or aralkyl, said alkyl, arylsulfonyl and aralkyl groups being unsubstituted or substituted with fluoro, alkyl or $R^{10}O$.

$R^2$ and $R^3$ independently represent hydrogen, $C_1$ to $C_7$ alkyl, cycloalkyl, aryl or aralkyl, said groups other than hydrogen being unsubstituted or substituted with $R^{10}O$, $R^{11}R^{12}N$, azide, alkyl, cycloalkyl or F;

A represents

$R^{12}N$, O or S.

$R^4$, $R^5$, $R^6$ and $R^7$ independently represent hydrogen, $C_1$ to $C_7$ alkyl, fluoroalkyl, cycloalkyl, aryl, aralkyl, $R^{10}O$, $R^{11}R^{12}N$, azide, or F;

When A represents $CR^8R^9$, $R^8$ and $R^9$ independently represent hydrogen, $OR^{10}$, $C_1$ to $C_7$ alkyl, fluoroalkyl, cycloalkyl, aryl, $R^{11}R^{12}N$, azide or F.

$R^{10}$ is hydrogen, $C_1$ to $C_7$ alkyl, fluoroalkyl, cycloalkyl, aryl or aralkyl.

$R^{11}$ is hydrogen, $C_1$ to $C_7$ alkyl, fluoroalkyl, cycloalkyl, aryl or aralkyl.

$R_{12}$ is hydrogen, $C_1$ to $C_7$ alkyl, fluoroalkyl, cycloalkyl, aryl, aralkyl or arylsulfonyl.

Alternatively, one of the pairs $R^4$ and $R^8$, $R^4$ and $R^9$, $R^5$ and $R^8$, $R^5$ and $R^9$, $R^6$ and $R^8$, $R^6$ and $R^9$, $R^7$ and $R^8$, and $R^7$ and $R^9$ represents a cyclic carbonate (—OC(O)O—), cyclic acetonide (—OC(CH_3)_2O—), or a $C_1$ to $C_5$ alkanediyl group which forms a ring with the carbon atoms to which such group is attached, said alkanediyl group being unsubstituted or substituted with $C_1$ to $C_7$ alkyl, fluoroalkyl, cycloalkyl, aryl, aralkyl, $R^{10}O$, $R^{11}R^{12}N$, azide or F.

Z represents O or $NR^1$, and

B represents $C^*HCH_2CH_3$, the asymmetric carbon atom *of which is in the (R) or (S) stereoconfiguration, or a bond between the carbon and nitrogen atoms to which B is attached.

DETAILED DESCRIPTION

The following terms have the meanings set forth below unless otherwise indicated.

Erythromycin A has the structure shown above. Numbering of the molecule as well as derivatives thereof, is conventional, starting with the ring lactone carbonyl group. Representative examples of fragment and compounds names are follows.

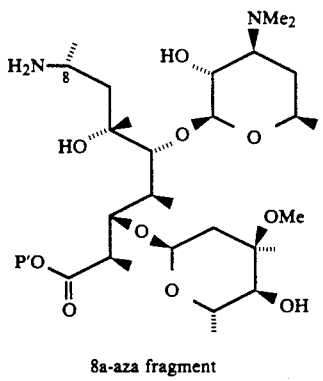

8a-aza fragment

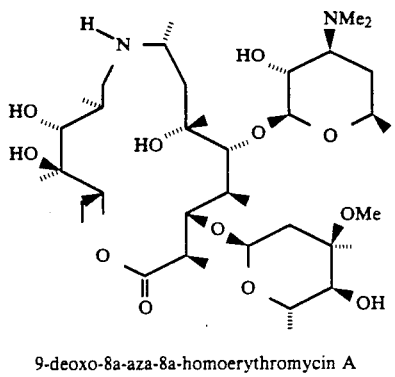

9-deoxo-8a-aza-8a-homoerythromycin A

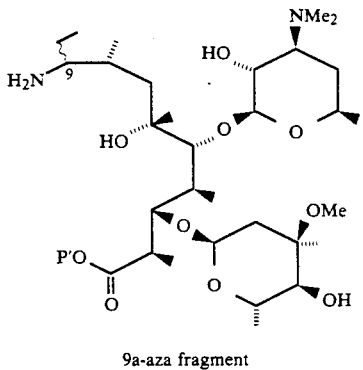

9a-aza fragment

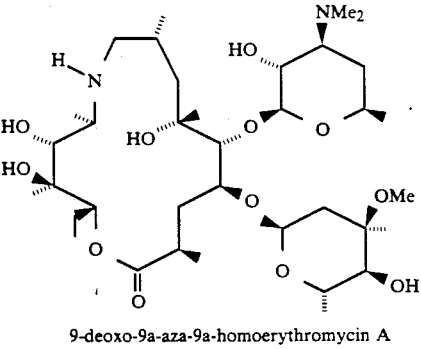

9-deoxo-9a-aza-9a-homoerythromycin A where P' is a protecting group. The 8a and 9a fragments are most typically in unprotected form.

The 8a- and 9a-aza fragments are useful intermediates in the synthesis of the present invention. These fragments have high structural homology to 9-deoxo-8a-aza-9a-homoerythromycin A and 9-deoxo-9a-aza-8a-homoerythromycin A in their "eastern" sides. By varying the compound A' which is used in combination with the reactive groups X and Y, the "western side" of the molecule can vary within wide limits. (The term "western side" refers to the compound or fragment which is used to complete the azalide ring with the 8a- and 9a-aza fragments shown above).

The term azalide is used throughout the specification, and refers to macrolide molecules which contain 13 to 16 atoms in a ring, with a nitrogen present at position 8a or 9a.

Amino refers to a group —$NH_2$ or the divalent group —NH—. Substituted amino refers to amino groups noted above with one or two substituents thereon, unless otherwise specified. Substituents can include lower alkyl, benzenesulfonyl, toluenesulfonyl, benzyloxycarbonyl and t-butyloxycarbonyl.

The term alkyl refers to an alkane, (hydrocarbon) group with 1 to 10 carbon atoms contained therein. Alkyl groups can be straight, branched or cyclic. Preferred alkyl groups include methyl, ethyl, propyl, butyl, t-butyl, pentyl and hexyl. When the alkyl group is substituted, e.g., fluoroalkyl, the fluoro group can be attached to the alkyl moiety at any available point of attachment. When the alkyl group is substituted with an alkyl group, which may be the same as a branched alkyl group. Lower alkyl refers to $C_1$ to $C_6$ alkyl groups.

Aryl refers to an aromatic ring or rings, e.g., phenyl, biphenyl, or rings which are fused, e.g., naphthalenyl, containing from 6 to 15 carbon atoms, and showing alternating double bonds in the ring structure. The preferred aryl group is phenyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms, said heteroaryl group being optionally substituted with up to four $R^q$ groups.

Heteroaryl thus includes aromatic and partially aromatic groups which contain one or more heteroatoms. The monocyclic heteroaryl has at least one nitrogen atom, and optionally one additional oxygen or sulfur heteroatom may be present. Examples of this type are pyrrole, pyridine, oxazole, thiazole and oxazine. Additional nitrogen atoms may be present together with the first nitrogen and oxygen or sulfur, giving, e.g., thiadiazole. The preferred heteroaryls are those where only nitrogen heteroatoms are present when there is more than one. Typical of these are pyrazole, tetrazole, imidazole, pyrimidine and pyrazine and triazine.

The term "heterocycloalkyl" refers to a cycloalkyl group (nonaromatic) in which one of the carbon atoms in the ring is replaced by a heteroatom selected from O, S, NH, or N($C_1$-$C_4$ alkyl), and in which up to three additional carbon atoms may be replaced by said hetero groups.

Halogen, or "halo" refers to atoms of bromine, chlorine, fluorine and iodine.

Alkoxy refers to $C_1$-$C_4$ alkyl—O—, with the alkyl group optionally substituted with the variable $R^q$.

Aralkyl is a specie of substituted alkyl, containing up to three aryl groups substituted on a straight, branched or cycloalkyl group. The most preferred aralkyl specie is benzyl.

Cycloalkyl is a specie of alkyl and refers to a hydrocarbon ring or rings containing 3 to 15 carbon atoms. When more than one ring is present, the rings can be fused. Cycloalkyl does not contain alternating or resonating double bonds in the structural drawing, as in aryl. The preferred cycloalkyl groups are cyclopentyl and cyclohexyl.

Alkanediyl refers to a divalent hydrocarbon chain, e.g., -alkylene-, which may be substituted or unsubstituted as appropriate. Typically there are two to five carbon atoms in alkanediyl, which may form a ring by attaching to two other atoms joined directly to each other or through other atoms.

When any of the groups noted above is termed "substituted", up to 6, and preferably 1-3 such substitutions are included at any available point(s) of attachment. Preferred substitute groups used herein are $C_{1-7}$ alkyl and $OR^{10}$ where $R^{10}$ is H, alkyl and fluoroalkyl. When an alkyl group is said to be substituted with an alkyl group, this refers to a straight or cycloalkyl group with an alkyl branch attached thereto, and thus may have the same meaning as branched alkyl.

The term "cyclic carbonate" refers to —OC(O)O— which is divalent. It typically forms a ring when attached to joined atoms. Likewise the term "cyclic acetonide" refers to —OC(Me)$_2$O— which forms a ring when attached to joined atoms.

The term "desosamine" (Des) refers to the compound 3,4,6-trideoxy-3-(dimethylamino)-D-xylo-hexose, which serves as one of the sugar components bonded to the azalide or the eastern fragment at carbon atom 5.

The term "cladinose" (Clad) refers to the compound 2,6-dideoxy-3C-methyl-3-O-methyl-alpha-L-ribo-hexopyranose, which serves as one of the sugars bonded to the azalide or eastern fragment thereof at carbon atom 3.

Vicinal hydroxy groups refer to hydroxyl groups on adjacent carbon atoms. Vicinal hydroxy groups can be protected together, such as by forming a cyclic carbonate.

Derivatives of eastern and western fragments are fragments which have one or more functional groups in protected form.

The stereochemical configuration of the compounds of the invention can be varied within wide limits, particularly in the western fragment, depending on the starting materials and the particular reaction parameters selected. All such stereoconfigurations are included herein, in pure form as well as in mixtures.

The designation X—A'—Y refers to the compound used to form the western half of the azalide molecule. Thus, X and Y constitute the groups which are reactive with the amino and ester or carboxylate groups of azalide eastern fragments. As shown in detail in the examples, the group Y is reactive with the amine group of the 8a- or 9a- aza eastern fragment, and includes, e.g., aldehydes, allyl groups, groups which contain leaving groups, such as a chloride and the like, groups which eliminate water upon reaction, such as hydroxyl groups. Other reactive groups can also be used.

The group X is reactive with the ester or carboxylate moiety of the azalide fragment, and includes, e.g., hydroxy groups, amino groups and other groups which can be convened to hydroxy and amino groups. It is recognized that X may be reactive with the carboxylate which is generated in many instances prior to reaction with X. Thus, X is said to be reactive with the ester or carboxylate derivative thereof.

The ester functional group is shown as P'OC(O)— in which P' typically is methyl or benzyl. Other ester forming groups are also contemplated.

It can also be noted that the X and Y groups can be selectively protected to facilitate reactions in the desired sequence. For example, the Y group can be protected, and the X group reacted with the ester or carboxylate moiety in the azalide eastern fragment. Likewise, the X group can be protected to facilitate reaction between the amino moiety and the Y reactive group.

The preferred process begins with a 9a-aza or 8a-aza fragment which can be derived from erythromycin A or one of its derivatives. The conversion of erythromycin A to the prototypical fragments is shown in the following diagram.

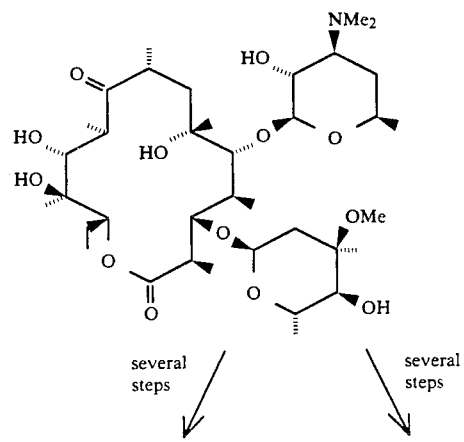

-continued

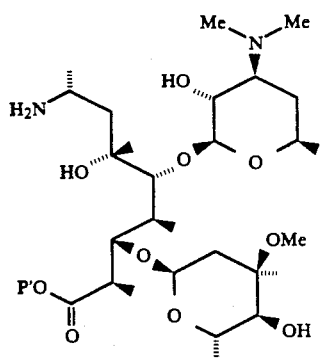
1

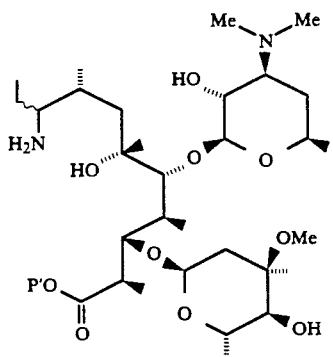
2

↓ several steps

↓ several steps

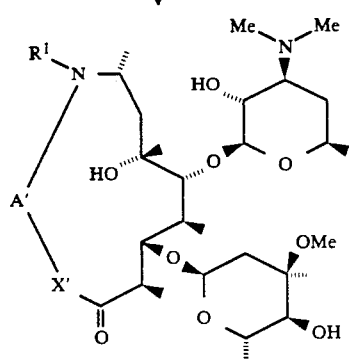
3

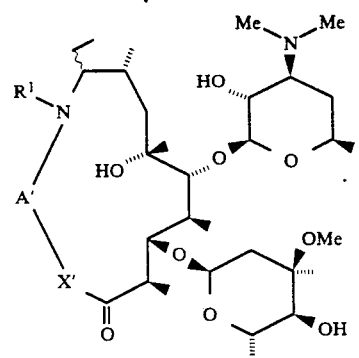
4

X' = O or NR$^1$

In fragments 1 and 2 above, P' represents methyl or benzyl. For simplicity, it is shown in the following diagrams as methyl. Briefly, the erythromycin precursor can be cleaved via a retro-aldol process in a polar, aprotic solvent, e.g., THF, with a strong base, e.g., potassium trimethylsilanoate. The resulting compound is typically a carboxylate salt, which can be esterified at $C_1$, e.g., via an acid catalyzed condensation with an alcohol or nucleophilic displacement on an electrophilic species by the carboxylate ion, e.g., alkyl halides, alkyl triflates, alkyl tosylates and the like. The most preferred method of esterification is via a reaction with diazomethane.

After cleavage of the erythromycin or erythromycin-like starting material, the eastern fragment can be converted into an oxime as shown below. This oxime can be produced from the ketone or the hemiketal which may be in equilibrium therewith. The ketone can be converted to the oxime using, e.g., hydroxylamine hydrochloride and base in a suitable solvent. Preferably the solvent is pyridine which is basic. Alternatively, an alcohol, e.g., ethanol, can be used in combination with an amine base, e.g., $Et_3N$.

The oxime can be reduced to the corresponding amine using a variety of techniques, e.g., high pressure catalytic hydrogenation, with, e.g., $PtO_2$ as a catalyst. Other catalysts can also be used, e.g., Pd/C, Raney Ni, and the like. Likewise, dissolving metal reduction, (Na, Na-Hg or Al-Hg), metal hydride reducing agents ($NaBH_4/TiCl_4$ or $NaBH_4/NiCl_2$) or $TiCl_3$ and $NaBH_3CN$ can be used.

The oxime can likewise be subjected to a Beckmann rearrangement as shown in the following flow chart.

Flow Chart 1
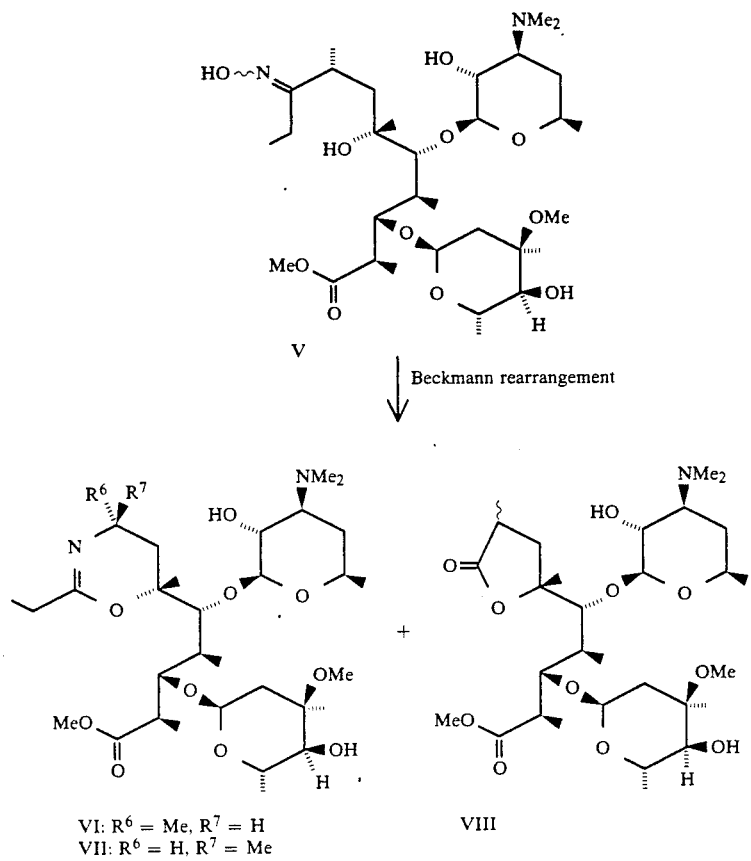
VI: R⁶ = Me, R⁷ = H
VII: R⁶ = H, R⁷ = Me
VIII
Flow Chart 2
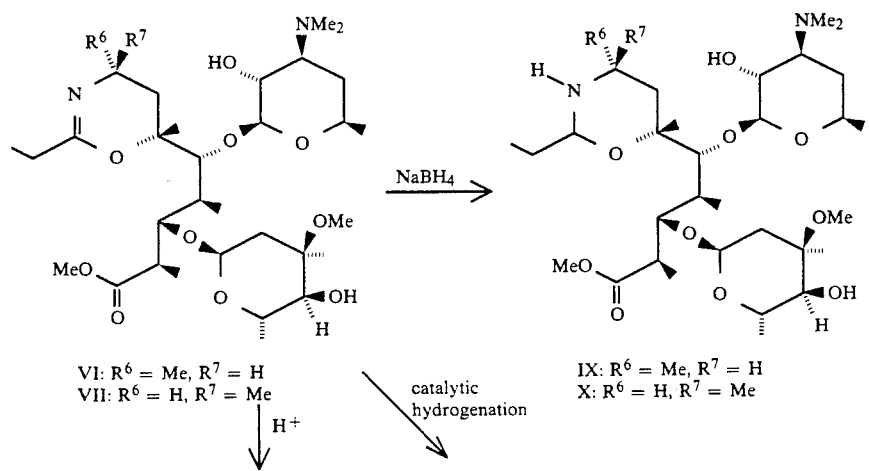
VI: R⁶ = Me, R⁷ = H
VII: R⁶ = H, R⁷ = Me
IX: R⁶ = Me, R⁷ = H
X: R⁶ = H, R⁷ = Me

Flow Chart 2 -continued

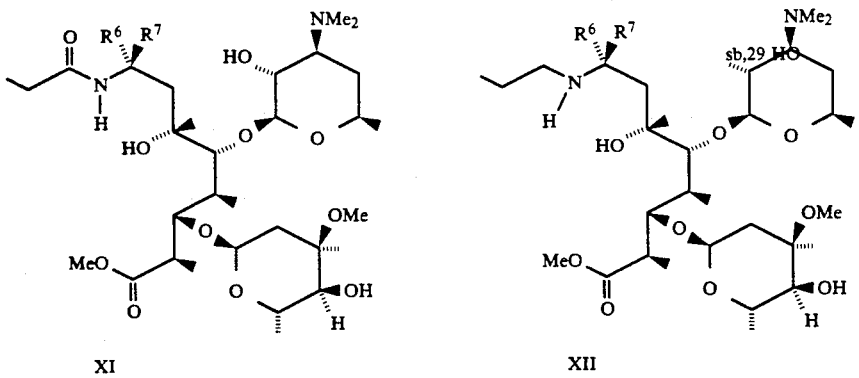

XI   XII

Flow Chart 3

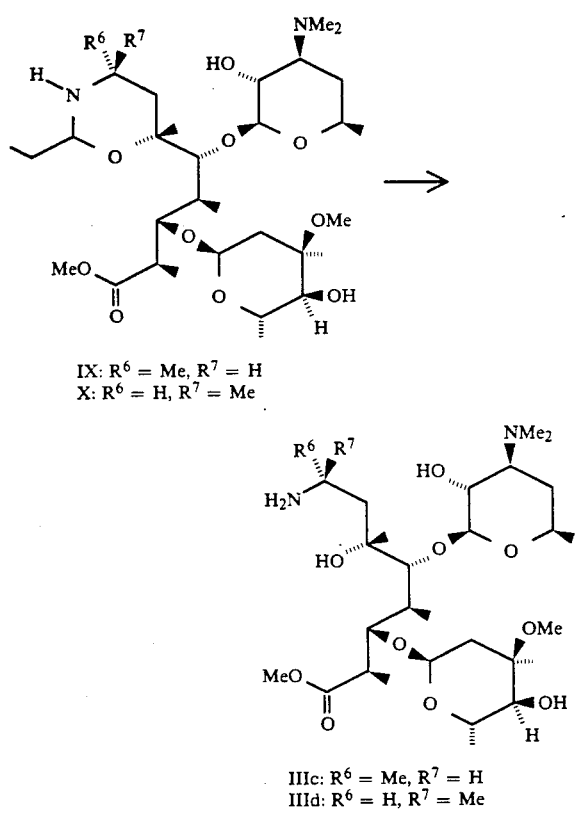

IX: $R^6$ = Me, $R^7$ = H
X: $R^6$ = H, $R^7$ = Me

IIIc: $R^6$ = Me, $R^7$ = H
IIId: $R^6$ = H, $R^7$ = Me

In general, the Beckmann rearrangement of ketoximes leads to carboxamides. The amine hydroxyl group is converted to a leaving group, which is lost with migration of the oxime carbon substituent that is situated anti to the leaving group. In aqueous media, the intermediate nitrilium cation thus formed is usually trapped by water to afford the amide product. The nitrilium intermediate can also be trapped by other nucleophiles, including intramolecular trapping by hydroxyl groups located elsewhere in the molecule.

There are many ways to accomplish the Beckmann rearrangement under acidic, neutral or basic conditions (see *Comprehensive Organic Chemistry*, I. O. Sutherland (ed.), Pergamon Press, New York, 1979, Vol. 2, pgs. 398–400 & 967–968). The macrolide fragment (particularly the cladinose residue) is sensitive to strong acid, e.g., concentrated sulfuric acid, polyphosphoric acid, thionyl chloride, phosphorus pentachloride, sulfur dioxide, and formic acid.

A preferred method for effecting the Beckmann rearrangement involves initial O-acylation of the oxime group with an alkylsulfonyl halide, arylsulfonyl halide or arylsulfonic anhydride. The intermediate oxime sulfonate thus formed can be isolated or, as more commonly practiced, converted in situ to the rearranged products. The acylation and rearrangement reactions are generally performed in the presence of an organic or inorganic base.

Preferred acylating reagents for effecting the rearrangement of the oxime include methanesulfonyl chloride, benzenesulfonyl chloride, 4-acetamidobenzenesulfonyl chloride, p-toluenesulfonyl chloride, benzenesulfonic anhydride, and p-toluenesulfonic anhydride. The reaction can be carried out in the presence of an inorganic base (such as sodium bicarbonate or potassium carbonate) or an organic base such as pyridine, 4-dimethylaminopyridine, triethylamine, or N,N-diisopropylethylamine. Suitable solvents include anhydrous organic solvents such as dichloromethane, chloroform, ethyl acetate, diethyl ether, tetrahydrofuran, toluene, acetonitrile, and pyridine. Mixtures of organic solvents, especially those containing pyridine, are very useful. Aqueous mixtures such as aqueous acetone or aqueous dioxane are unsuitable because they favor formation of the amide XI. The reaction is generally performed using 1–5 molar equivalents of the acylating reagent and one or more molar equivalents of base at −10° C. to 60° C. Pyridine can be used as both the solvent and the base.

The distribution of products resulting from the Beckmann rearrangement of oxime V depends on the particular reaction conditions employed. In general, treating a 0.05 to 0.1M solution of the oxime in pyridine with one equivalent of activating reagent (such as p-toluenesulfonyl chloride or p-toluenesulfonic anhydride) at room temperature leads to incomplete conversion of starting material to the desired imino ether VI. If the reaction is conducted at 60° C. it proceeds essentially to completion, but with substantial formation of the lactone by-products VIII (along with a smaller amount of the epimeric by-product VII). Conducting the reaction at room temperature with 5 equivalents of the activating reagent also forces the reaction to near completion, but with substantial formation of epimeric by-product VII (along with smaller amounts of VIII.).

Catalytic hydrogenation (1000 psi $H_2$ with $PtO_2$ catalyst in acetic acid) furnishes the propylamine XII in good yield. Reduction of iminoether VI with sodium borohydride at room temperature or at pH<6 also furnishes predominantly the propylamine XII.

The preferred means of reducing the iminoether VI to the aminal IX essentially follows the method developed by Myers et al and described in *J. Org. Chem.*, Vol. 38, No. 1, p. 36, 1973. This involves cooling a solution of the iminoether VI (0.005M to 0.5M) in a 1:1 mixture of tetrahydrofuran and 95% ethanol to between −35° C. and −45° C., and then treating this solution with from 1 to 5 mole equivalents (3 most preferred) of sodium borohydride in a small amount of water. To this solution is then added 850 ml of 2N HCl for each millimole of sodium borohydride used. This produces a solution which "tests" as pH 6 to 7 when applied to damp pH paper. The reaction is allowed to stir for 4 to 24 hours at a temperature of between −35° and −45° C. Any lactone contaminant in the starting material is unaffected by this reaction.

The aminal IX produced in this manner can be isolated by silica chromatography using ammonia as a component of the eluent. Normally the aminal is not isolated, however, but is directly hydrolyzed to the amine fragment IIIc. This hydrolysis can be accomplished by exposing the aminal to a mild acid in the presence of water. A preferred method of accomplishing this hydrolysis involves exposing the aminal to a mixture of THF, ethanol, and pH 4 aqueous acetic acid at room temperature. The reaction is allowed to proceed for between 5 and 48 hours, with 16 hours preferred.

Compounds 3 and 4 can be prepared readily from amine fragments 1 and 2, respectively, using readily available starting materials, reagents and conventional synthesis procedures.

It is necessary to synthesize or procure an appropriate fragment which will become the western portion of 3 or 4. Shown in the flow charts generally as —A'—, in its simplest form, this can be a carbon chain of 3 to 5 atoms which can bear an aldehyde or allylic function at one end and an amino or hydroxy group at the other, in protected or unprotected form. This chain may also bear a variety of substituents, including hydrogen, alkyl, aryl, aralkyl, hydroxy or protected hydroxy, cyclic carbonate, cyclic acetonide, protected amino, cyclic carbamate and halogen. This segment —A'— can be referred to as the "chimeric segment".

The chimeric segment can generally be a carbon chain ranging from 3 to 6 carbon atoms, said chain being uninterrupted or interrupted by up to two heteroatoms, O, S or $NR^1$ with $R^1$ as defined above. Likewise, the chain can be interrupted by or substituted with one or two aryl, heteroaryl, cycloalkyl, or heterocycloalkyl groups. The carbon atoms of the chimeric segment and of the optional interrupting groups can be unsubstituted or can be substituted with lower alkyl, halo, e.g., F, Br, Cl or I, hydroxyl, alkoxyl, amino, aryl, heteroaryl, cycloalkyl, heterocycloalkyl, aryloxy, arylsulfonyl, arylsulfonylamino, substituted aryl, substituted heteroaryl, substituted alkyl, substituted cycloalkyl, substituted heterocycloalkyl, substituted aryloxy, substituted arylsulfonyl and substituted arylsulfonylamino groups, at any available point of attachment.

Simple chimeric segments can be constructed from common α,ω-hydroxyaldehydes, α,ω-diols and α,ω-hydroxyamines. Carbohydrates represent a large and versatile pool of precursors for polyhydroxylated chimeric segments of various lengths and stereochemistries. Amino acids can similarly be converted into amine containing chimeric segments. Many other desirable chimeric segments can be simply prepared by asymmetric total synthesis.

In, for example, the hydroxyaldehydes, the hydroxyl group is reactive with the ester group of the 8a- or 9a-aza fragment. Thus, the hydroxy group is designated X and the aldehyde group is designated Y. The carbon atom to which the X hydroxy group is attached is considered part of the carbon chain —A'—, as is the carbon atom which forms part of the aldehyde moiety.

Attachment of the chimeric segment to the primary amine of fragment 1 or 2 can be accomplished, e.g., by reductive amination if the chimeric fragment contains an aldehyde function, or, e.g., by metal catalyzed (e.g. palladium catalyzed) coupling if the chimeric segment contains an allylic acetate. (Y=aldehyde or allylic group). Naturally, other types of chimeric segments can be attached in other ways. In the most commonly practiced manifestation of the invention, the chimeric segment contains an aldehyde function, and the attachment can be accomplished by reductive amination. The preferred method of reductive amination uses sodium cyanoborohydride in a minimum of methanol, with heating if necesssary. Other means of reductive amination may also be used.

In an alternative embodiment of the invention, the chimeric segment can be attached to the amine fragment 1 or 2 by forming an amide or ester bond between the carboxylate of the amine fragment and an amino or hydroxy group on the chimeric segment. (X=amino or hydroxy). Cyclization is then onto the 8a or 9a nitrogen and can be accomplished by intramolecular reductive amination, metal catalyzed coupling, or by other processes which form C—N bonds.

Macrolactonization

In the macrolactonization sequence, cyclization is best performed with the 8a or 9a nitrogen and any nitrogens on the chimeric segment rendered non-basic by the presence of an appropriate protecting group, such as alkyloxycarbonyl, aralkyloxycarbonyl or arylsulfonyl. The most preferred group for this purpose is benzenesulfonyl, which can be efficiently and selectively removed at the end of the sequence. The benzenesulfonyl group can be introduced using benzenesulfonyl chloride in methylene chloride with triethylamine and N,N-dimethylaminopyridine, with heating if necessary.

Hydroxy groups on the chimeric segment can also be rendered non-nucleophilic by the presence of an appropriate protecting group, such as benzyl, substituted aralkyl, or trialkylsilyl. Vicinal hydroxy groups can be protected as cyclic acetals or ketals, or cyclic carbonates. Vicinal amino and hydroxy groups can also be protected together as a cyclic carbamate.

In one embodiment of the invention, a single hydroxy group is deprotected for the cyclization. In the most commonly practiced manifestation of the invention, there is a single hydroxy group protected as a t-butyldimethylsilyl or t-butyldiphenylsilyl ether, and any other hydroxy groups on the chimeric segment are protected as methyl or benzyl ethers or cyclic acetonides, carbonates or carbamates. In this case, the single hydroxy group can be revealed by reaction with tetra-n-butylammonium fluoride in tetrahydrofuran.

Prior to macrolactonization, the ester moiety of the eastern fragment can be hydrolyzed. This can be accomplished using a mixture of tetrahydrofuran, methanol and 1N aq. NaOH. After the saponification is complete, the mixture can be neutralized, the solvent removed under vacuum, and the residue can be used in the cyclization reaction with or without purification.

The most preferred method of macrolactonization is a Mitsunobu cyclization: reaction of a dilute solution of the hydroxycarboxylate in tetrahydrofuran with diethyl or diisopropyl azodicarboxylate and triphenylphosphine. This gives satisfactory cyclization at primary and many secondary hydroxy groups. Other proximate nucleophiles can effect displacement, but the unprotected hydroxy groups at C-2', C-4" and C-6, and the basic amine at C-3' generally do not pose a problem in the cyclization. Macrolactonization methods which activate the carboxylate to intramolecular attack by a hydroxy group can fail because cyclization tends to occur onto the C-6 or C-2' hydroxy, but in certain cases these methods can work well.

Once cyclization has occurred, protecting groups may be removed from any protected atoms in the chimeric segment or in the 8a- or 9a- aza fragment. In the most commonly practiced manifestation of the invention, ring nitrogens which are protected with the benzenesulfonyl group can be deprotected simultaneously. The preferred method of removing the benzenesulfonyl group is that described by Yonemitsu et. al. in *J. Am. Chem. Soc.* 1986, 108, 140: photolysis in 95% ethanol in the presence of 1,5-dimethoxynaphthalene and a reducing agent such as ascorbic acid or hydrazine. Sodium amalgam in buffered methanol can also be used to effect this deprotection, but the high concentration of methoxide under these conditions can lead to ring opening of the lactone. Hydroxy groups which are often protected as benzyl ethers can be removed by catalytic hydrogenation, either before or after the deprotection of the nitrogen. Deprotection of hydroxy groups on the chimeric segment can result in translactonization. Vicinal hydroxy groups which are protected as cyclic carbonates can be deprotected with mild base.

A commonly practiced embodiment of the invention is summarized in flow chart 4 for easy visual reference. It is not intended to exclude other embodiments of the invention as described above.

Flow Chart 4

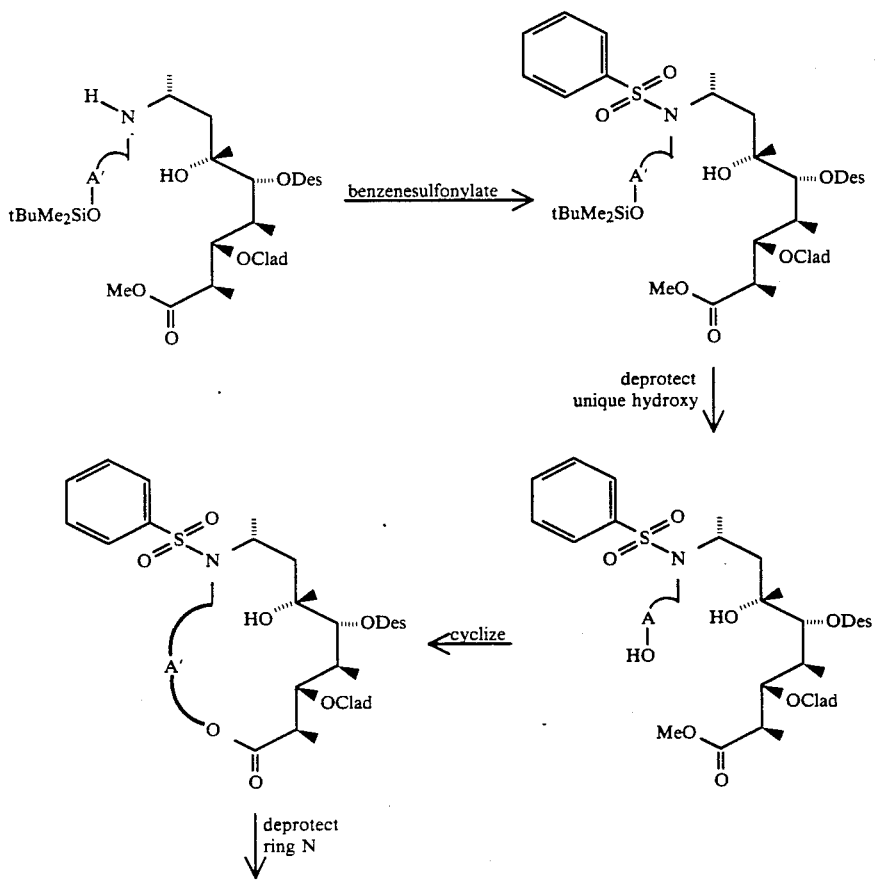

Flow Chart 4

-continued

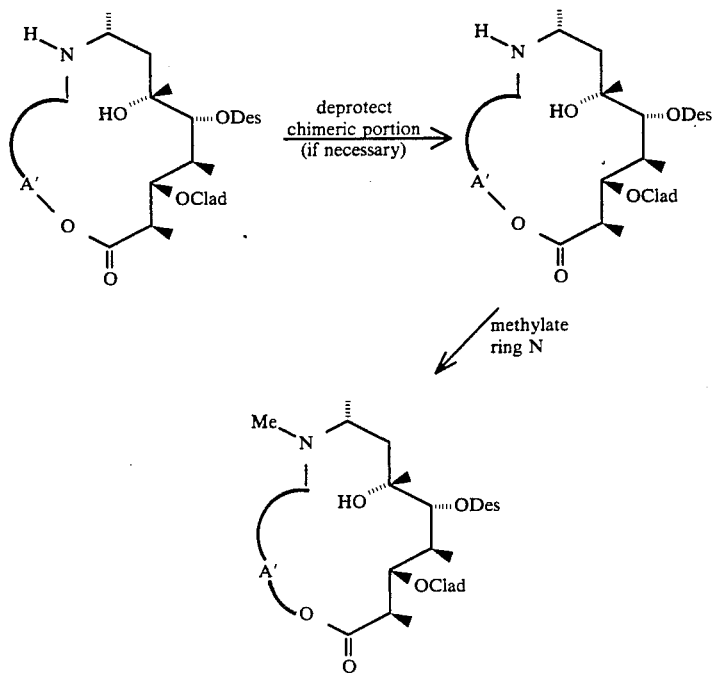

Macrolactamization

The basic ring nitrogen (8a or 9a) does not substantially interfere with the macrolactamization reaction as long as it is a tertiary amine (tertiary amines on the chimeric segment are likewise tolerated.) After attachment of the chimeric segment, the 8a or 9a nitrogen can be either benzenesulfonlylated (in order to produce 8a or 9a-NH macrocycles) or simply alkylated (which produces 8a or 9a-N-alkyl macrocycles). In the most commonly practiced manifestation of the invention, the 8a or 9a nitrogen is methylated at this point using formaldehyde and sodium cyanoborohydride. Other reductive amination methods, such as the Eschweiler-Clark procedure (formic acid and formaldehyde) may also be used.

It should also be noted that oxygen nucleophiles do not substantially interfere with the macrolactamization reaction, so that the chimeric segment may bear unprotected hydroxy groups.

In the macrolactamization sequence, the chimeric segment bears X as either a protected amine or an amine equivalent. Suitable protecting groups for an amine on the chimeric segment include e.g., the alkoxycarbonyl or aralkoxycarbonyl groups, with the benzyloxycarbonyl group being most preferred. If the 8a or 9a nitrogen is alkylated, arylsulfonyl groups may be used. The benzyloxycarbonyl group can be removed at this stage by catalytic hydrogenation. However, in the most commonly practiced manifestation of the invention, the chimeric segment bears an amine equivalent, usually azide, which can be converted to an amine at this stage by reduction. The most preferred method for reduction of the azide is reaction with triphenylphosphine in aqueous tetrahydrofuran, although other methods, such as catalytic hydrogenation, may also be used.

The macrolactamization reaction typically begins with hydrolysis of the methyl ester. This can be accomplished using a mixture of tetrahydrofuran, methanol and 1N aq. NaOH. After the saponification is complete, the mixture can be neutralized, the solvent removed under vacuum, and the residue can be used in the cyclization reaction with or without purification. The most preferred method of macrolactamization is reaction of the aminocarboxylate with diphenylphosphorylazide at low temperature.

After cyclization, if the 8a or 9a nitrogen was protected as N-benzenesulfonyl, this group can be removed to produce the 8a or 9a-NH macrocycle as described above for the macrolactones.

A commonly practiced embodiment of the invention is summarized in flow chart 5 for easy visual reference. It is not intended to exclude other embodiments of the invention as described above.

Flow Chart 5

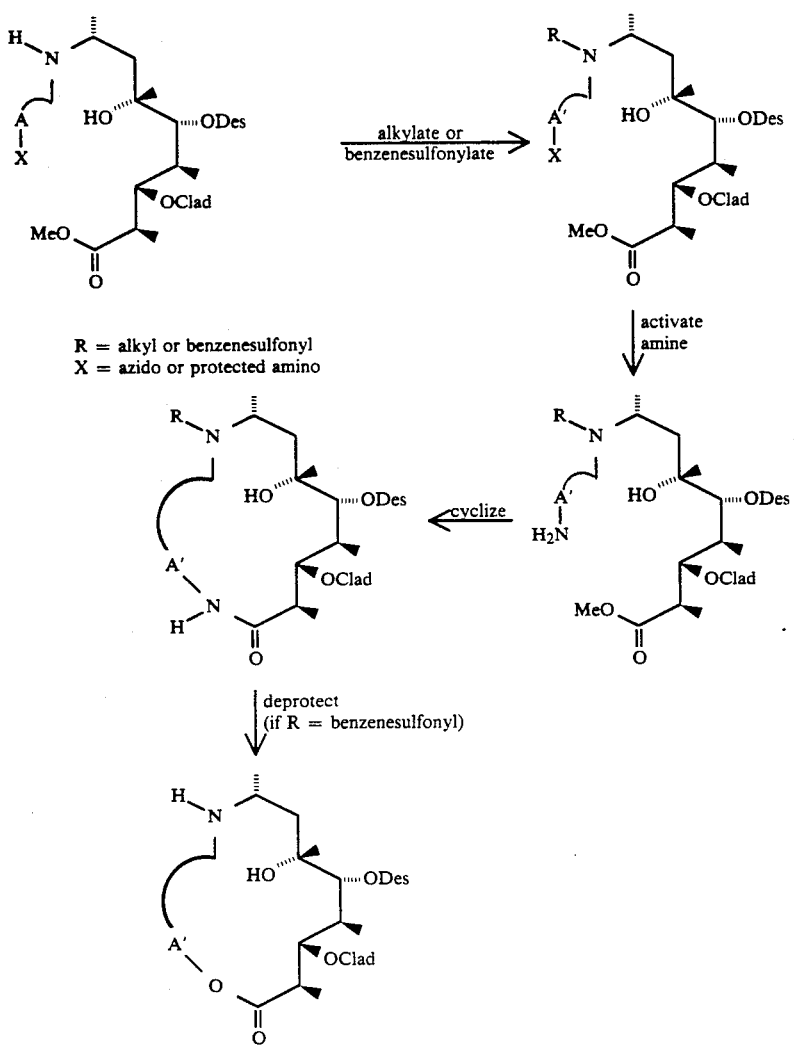

R = alkyl or benzenesulfonyl
X = azido or protected amino

The invention is further described in connection with the following non-limiting examples.

EXAMPLE 1

Preparation of (S)-3-t-Butyldimethylsilyloxybutanal

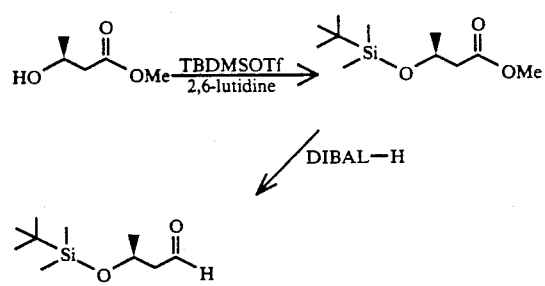

To a 500 ml round bottom flask was introduced 2.54 g (21.5 mmol) of methyl (S)-3-hydroxybutanoate (Aldrich Chemicals), to which was added 70 ml $CH_2Cl_2$, and 5 ml of 2,6-lutidine. The reaction was stirred in an ice bath, and 4.94 ml (5.68 g, 21.5 mmol) of t-butyldimethylsilyl triflate was added dropwise. After stirring for 1 hour, the reaction was diluted with 250 ml of $CH_2Cl_2$ and extracted three times with 50 ml of water. The organic layer was dried over $MgSO_4$ and the solvent was removed under reduced pressure. The residue was chromatographed on silica gel using 10% ethyl acetate in hexane. This afforded 4.3 g (86%) of the product, methyl (S)-3-t-butyldimethylsilyloxybutanoate.

To a 50 ml round bottom flask was introduced 200 mg (0.86 mmol) of methyl (S)-3-t-butyldimethylsilyloxybutanoate, to which was added 2.5 ml dry $CH_2Cl_2$. The reaction was stirred in a dry ice/acetone bath, and 1.72 ml (2 eq.) of 1M diisobutylaluminum hydride in toluene was added dropwise. After stirring for 1 hour at −78° C., the reaction was quenched with 2 ml of MeOH and warmed to room temperature. The reaction was diluted with 25 ml of $CH_2Cl_2$ and 8 ml saturated aq. potassium sodium tartrate was added. The organic layer was separated and dried over $MgSO_4$ and the solvent was removed under reduced pressure. Thin layer chromatography using 10% ethyl acetate in hexane showed complete and clean conversion to a lower Rf spot. This afforded 170 mg (98%) of the product, (S)-3-t-butyldimethylsilyloxybutanal, which was used without purification to avoid racemization.

EXAMPLE 2

General Preparation of t-Butyldimethylsilyloxy Aldehydes from Hydroxyesters

Following the procedure given in example 1, a variety of hydroxyesters can be converted to t-butyldimethylsilyloxy aldehydes. A representative but nonlimiting sampling of the compounds that can be produced in this manner include those in the following table:

TABLE 1

| hydroxyester | t-butyldimethylsilyloxyaldehyde |
|---|---|
| 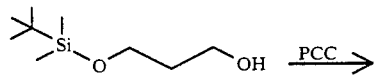 | |

EXAMPLE 3

Preparation of 3-t-butyldimethylsilyloxypropanal

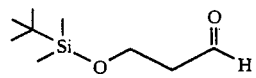

To a 500 ml round bottom flask was introduced 5.23 g (27.5 mmol) of 3-t-butyldimethylsilyloxypropanol (prepared according to the method of McDougal et al, *J. Org. Chem.* 1986, 51, 3388), to which was added 175 ml CH$_2$Cl$_2$, and 8.13 g (36.4 mmol, 1.3 eq) of pyridinium chlorochromate. The reaction was stirred 90 minutes, diluted with ether, and filtered through Florisil ™. The solvent was removed under reduced pressure and the residue was chromatographed on silica gel using 10% ether in hexane. This afforded 2.63 g (50%) of the product, 3-t-butyldimethylsilyloxypropanal.

EXAMPLE 4

General Preparation of t-Butyldimethylsilyloxy Aldehydes from Symmetric Diols In a two step sequence, beginning with t-butyldimethylsilylation according to the method of McDougal et al, *J. Org. Chem.* 1986, 51, 3388, and followed by oxidation according to the procedure given in example 3, a variety of symmetric diols can be converted to t-butyldimethylsilyloxy aldehydes. A representative but nonlimiting sampling of the compounds that can be produced in this manner include those in the following table:

TABLE 2

| Starting Diol | t-Butyldimethylsilyl Aldehyde |
|---|---|

EXAMPLE 5

Preparation of 2-(R)-3-(S)-4-(R)-trialkoxy-5-t-butyldimethylsilyloxypentanal

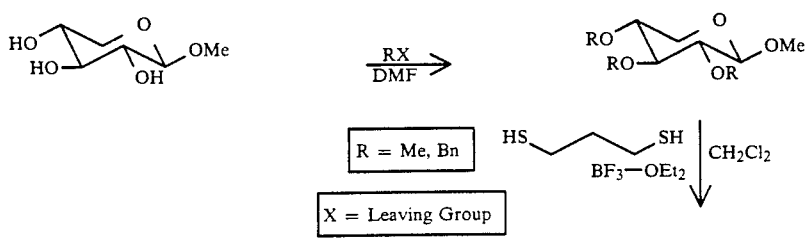

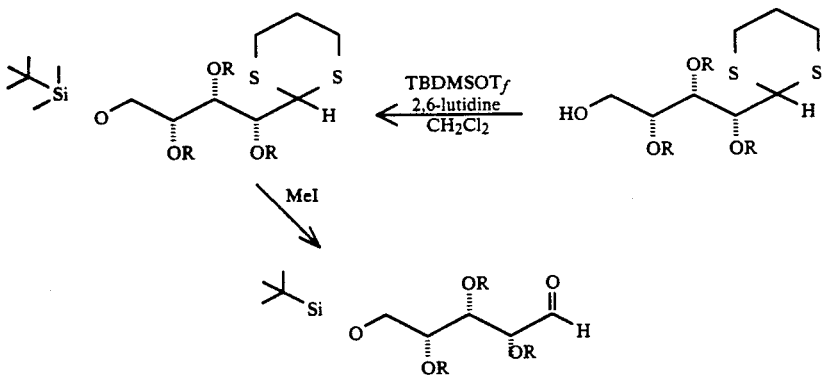

Preparation of 2-(R)-3-(S)-4-(R)-trimethoxy-5-t-butyldimethylsilyloxypentanal To a 100 ml round bottom flask was introduced 164 mg (1 mmol) of methyl-β-D-xylopyranoside, to which was added 10 ml dry DMSO and 0.28 ml MeI (4.5 eq.). This mixture was stirred at room temperature and 120 mg (4.5 eq.) of NaH (80% oil dispersion) was added in several small portions. The reaction was stirred for 18 hours and then added to 250 ml of methylene chloride and extracted four times with 50 ml of water. The organic layer was dried over magnesium sulfate and the solvent was removed under vacuum. This afforded 181 mg (88%) of 2,3,4-tris-(O-methyl)-methyl-β-D-xylopyranoside which was sufficiently pure to be used directly in the next reaction.

To a 100 ml round bottom flask was introduced 310 mg (1.5 mmol) of 2,3,4-tris-(O-methyl)-methyl-β-D-xylopyranoside, to which was added 15 ml dry CH$_2$Cl$_2$ and 0.23 ml 1,3-propanedithiol (248 mg, 2.30 mmol, 1.5 eq.). This mixture was stirred in an ice bath and 1.15 ml (1.32 g, 9.36 mmol, 6.2 eq.) of boron trifluoride etherate was added dropwise. The reaction was stirred for 3 hours at 0° C., at which time it was judged to be complete by TLC (2:1 EtOAc/hexane, product is lower R$_f$). The reaction was quenched with 15 ml of aq. sat. NaHCO$_3$, and the organic layer was separated and extracted twice with 5 ml of aq. sat. NaHCO$_3$. The organic layer was dried over magnesium sulfate and the solvent was removed under vacuum. The residue was chromatographed on silica, eluting with 66% ethyl acetate/hexane. This afforded 157 mg (37%) of 2-(R)-3-(S)-4-(R)-trimethoxy-5-hydroxypentanal-1,3-dithiane.

To a 100 ml round bottom flask was introduced 116 mg (0.411 mmol) of 2-(R)-3-(S)-4-(R)-tris(methoxy)-5-hydroxypentanal-1,3-dithiane, to which was added 10 ml dry THF and 0.270 ml 2,6-lutidine (248 mg, 2.32 mmol, 5.6 eq.). This mixture was stirred in an ice bath and 0.295 ml (339 mg, 1.28 mmol, 3.1 eq.) of t-butyldimethylsilyl triflate was added dropwise. The reaction was stirred for 30 minutes at 0° C., at which time it was judged to be complete by TLC (1:4 EtOAc/hexane, product is higher R$_f$). The reaction was diluted with 200 ml of CH$_2$Cl$_2$ and extracted twice with 15 ml of aq. sat. NaHCO$_3$. The organic layer was dried over magnesium sulfate and the solvent was removed under vacuum. The residue was chromatographed on silica, eluting with 7.5% ethyl acetate/hexane. This afforded 143 mg (82%) of 2-(R)-3-(S)-4-(R)-trimethoxy-5-t-butyldimethylsilyloxypentanal-1,3-dithiane.

To a 100 ml round bottom flask was introduced 71 mg (0.18 mmol) of 2-(R)-3-(S)-4-(R)-trimethoxy-5-t-butyldimethylsilyloxypentanal-1,3-dithiane, to which was added 3 ml 4:1 acetonitrile/water and 0.200 ml MeI (456 mg, 3.21 mmol, 17.8 eq.). This mixture was heated to 55° C. and stirred for 18 hours, at which time it was judged to be complete by TLC (1:1 EtOAc/hexane, product is slightly lower R$_f$). The reaction was diluted with 200 ml of CH$_2$Cl$_2$ and extracted twice with 15 ml of aq. sat. NaHCO$_3$. The organic layer was dried over magnesium sulfate and the solvent was removed under vacuum. The residue was chromatographed on silica, eluting with 7.5% ethyl acetate/hexane. This afforded 40 mg (73%) of 2-(R)-3-(S)-4-(R)-trimethoxy-5-t-butyldimethylsilyloxypentanal.

Selected spectral data for 2-(R)-3-(S)-4-(R)-trimethoxy-5-t-butyldimethylsilyloxypentanal.:

$^1$H NMR (400 MHz, CDCl$_3$) δ 9.68 (s, 1H), 3.81 (d, 1H), 3.70 (m, 2H), 3.50 (s, 3H), 3.47 (s, 3H), 3.39 (m, 1H), 3.27 (s, 3H), 0.86 (s, 9H), 0.04 (s, 6H).

Preparation of 2-(R)-3-(S)-4-(R)-tribenzyloxy-5-t-butyldimethylsilyloxy-pentanal To a 50 ml round bottom flask was introduced 2.44 g (14.8 mmol) of methyl-β-D-xylopyranoside, to which was added 65 ml dry DMSO, 3 g of tetra-n-butylammonium iodide and 6.5 ml benzyl bromide (9.4 g, 55 mmol, 3.7 eq.). This mixture was stirred at room temperature and 1.65 g (55 mmol, 3.7 eq.) of NaH (80% oil dispersion) was added in several portions. The reaction was stirred for 18 hours and then added to 800 ml of methylene chloride and extracted four times with 200 ml of water. The organic layer was dried over magnesium sulfate and the solvent was removed under vacuum. The residue was chromatographed on silica, eluting with 10% ethyl acetate/hexane. This afforded 6.26 g (88%) of 2,3,4-tris-(O-benzyl)-methyl-β-D-xylopyranoside. Following the procedures given above for the three subsequent steps afforded 2-(R)-3-(S)-4-(R)-tris(benzyloxy)-5-t-butyldimethylsilyloxypentanal.

Selected spectral data for 2-(R)-3-(S)-4-(R)-tribenzyloxy-5-t-butyldimethylsilyloxypentanal.:

$^1$H NMR (400 MHz, CDCl$_3$) δ 9.75 (s, 1H), 7.3 (m, 15H), 4.8 (d, 1H), 4.79 (d, 1H), 4.66 (d, 1H), 4.52 (m, 2H), 4.50 (d, 1H), 4.00 (m, 1H), 3.92 (d, 1H), 3.7 (m, 2H), 3.57 (m, 1H), 0.90 (s, 9H), 0.01 & −0.01 (singlets, 3H each).

EXAMPLE 6

General Preparation of Carbohydrate Derived t-Butyldimethylsilyloxyalkanals

Using the procedure given in example 5, a wide variety of monosaccharides can be convened into a t-butyldimethylsilylalkanal. A representative but nonlimiting sampling of the compounds that can be produced in this manner include those in the following table:

TABLE 2-1

| Starting Carbohydrate | t-Butyldimethylsilyl Aldehyde R = Me or Bn |
|---|---|
| 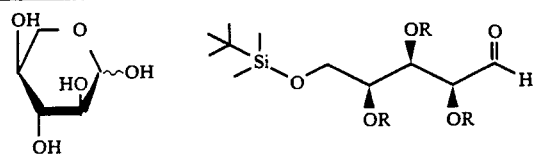 | |
| 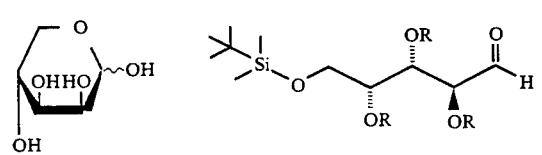 | |
| 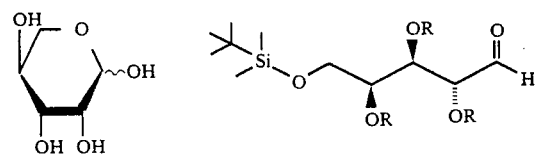 | |
| 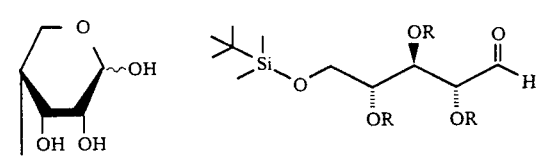 | |
| 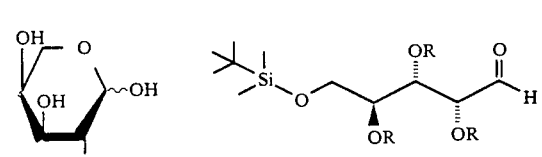 | |
| 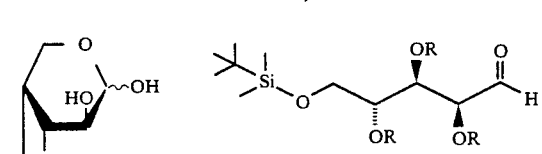 | |

TABLE 2-2

| Starting Carbohydrate | t-Butyldimethylsilyl Aldehyde R = Me or Bn |
|---|---|
| 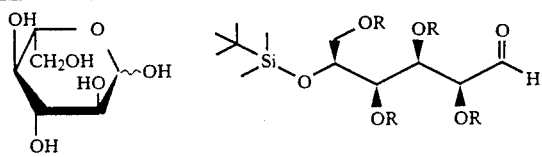 | |

TABLE 2-2-continued

| Starting Carbohydrate | t-Butyldimethylsilyl Aldehyde R = Me or Bn |
|---|---|

TABLE 2-3

| Starting Carbohydrate | t-Butyldimethylsilyl Aldehyde R = Me or Bn |
|---|---|

| TABLE 2-3-continued | |
|---|---|
| Starting Carbohydrate | t-Butyldimethylsilyl Aldehyde R = Me or Bn |
| 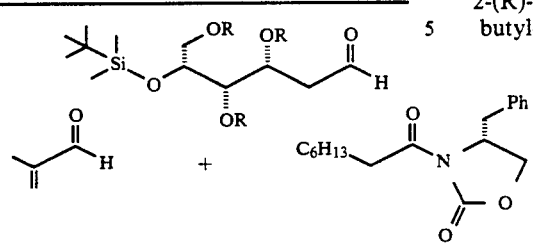 | |

EXAMPLE 7

Preparation of 2-(R)-hexyl-3-(R)-hydroxy-4-hydroxy-4-methyl-5-t-butyldiphenylsilyloxypentanal 3-O,4-O-acetonide

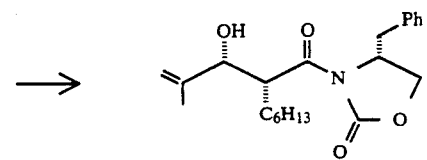

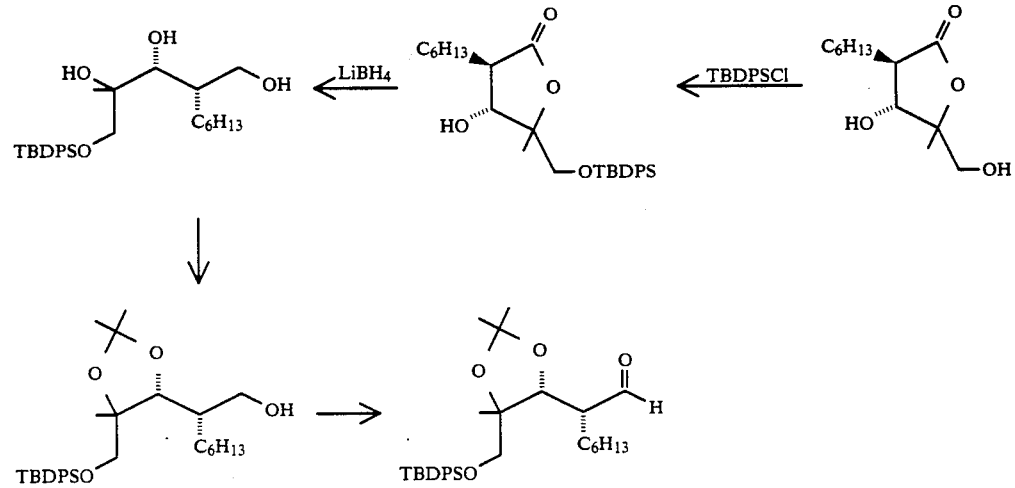

| TABLE 2-4 | |
|---|---|
| Starting Carbohydrate | t-Butyl dimethyl silyl aldehyde |
| | |
| | |
| | |

Preparation of 3-(1-Oxo-2-(R)-hexyl-3-(R)-hydroxy-4-methyl-4-pentenyl)-4-(R)-(phenylmethyl)-2-oxazolidinone This material was prepared from (R)-3-(1-oxooctyl)-4-(phenylmethyl)-2-oxazolidinone and methacrolein following the method of Evans and Gage, as described in Org. Syn., Vol. 68, 1989, p. 83.

Selected spectral data for 3-(1-oxo-2-(R)-hexyl-3-(R)-hydroxy-4-methyl-4-pentenyl)-4-(R)-(phenylmethyl)-2-oxazolidinone $^1$H NMR (400 MHz, CDCl$_3$) δ 7.25 (m, 5H), 5.07 (s, 1H), 4.92 (s, 1H), 4.68 (m, 1H), 4.31 (br s, 1H), 4.15 (m, 2H), 3.32 (dd, 1H), 1.73 (s, 3H), 0.83 (br t, 3H).

Preparation of 2-(R)-hexyl-3-(R)-hydroxy-4-methyl-4-hydroxymethyl-butyrolactone

To a 100 ml round bottom flask was introduced 340 mg (0.91 mmol) of 3-(1-oxo-2-(R)-hexyl-3-(R)-hydroxy-4-methyl-4-pentenyl)-4-(R)-(phenylmethyl)-2-oxazolidinone, to which was added 14 ml THF, 0.36 ml water, and 532 mg 4-methylmorpholine N-oxide (4.55 mmol, 5 eq.). The reaction was stirred at room temperature and 0.36 ml of 0.25M OsO$_4$ in THF was added dropwise. After 1 hour, the reaction was quenched with 2 ml of 20% aq. NaHSO$_3$, added to 30 ml of ethyl acetate and extracted twice with 10 ml 20% aq. NaHSO$_3$ then with 10 ml water. The organic layer was separated, dried over MgSO$_4$, and the solvent was removed under vacuum. A 400 MHz proton NMR of the crude reaction product revealed that a mixture of diastereomers at C-4 was formed in about an 8 to 1 ratio, with the stereochemistry of the major product uncertain. The residue was taken up in 60% hexane/ethyl acetate and chromatographed on silica gel using the same solvent mixture. The two diastereomers and the chiral auxilliary proved to be difficult to cleanly separate from each other by chromatography: the minor diastereomer elutes first, followed by the major diastereomer, followed by the chiral auxilliary. Careful chromatography afforded fractions enriched in each product. The total mass of the three products combined was 318 mg (86%).

Selected spectral data for 2-(R)-hexyl-3-(R)-hydroxy-4-methyl-4-hydroxymethylbutyrolactone (major stereoisomer at C-4)

$^1$H NMR (400 MHz, CDCl$_3$) δ 4.32 (d, 1H), 3.68 (d, 1H), 3.58 (d, 1H), 2.64 (m, 1H).

Selected spectral data for 2-(R)-hexyl-3-(R)-hydroxy-4-methyl-4-hydroxymethylbutyrolactone (minor stereoisomer at C-4)

$^1$H NMR (400 MHz, CDCl$_3$3) δ 3.97 (d, 1H), 3.86 (d, 1H), 3.72 (d, 1H), 2.77 (m, 1H).

Preparation of
2-(R)-hexyl-3-(R)-hydroxy-4-methyl-4-t-butyldiphenylsilyloxymethylbutyrolactone To a 100 ml round bottom flask was introduced a mixture of 68 mg (0.30 mmol) of 2-(R)-hexyl-3-(R)-hydroxy-4-methyl-4-hydroxy-methylbutyrolactone (major stereoisomer at C-4 from the previous reaction) and 117 mg of the chiral auxilliary which failed to be separated after the previous reaction, to which was added 2 ml sieve dried CH$_2$Cl$_2$, 15 mg of dimethylaminopyridine, 0.276 ml sieve dried triethylamine (202 mg, 2 mmol, 6.7 eq.), and 0.156 ml t-butyldiphenylsilyl chloride (166 mg, 0.6 mmol, 2 eq.). The reaction was stirred at 50° C. for 24 hours, then introduced directly to a silica column and chromatographed with 85% hexane/ethyl acetate. This afforded 40 mg (50%) of 2-(R)-hexyl-3-(R)-hydroxy-4-methyl-4-t-butyldiphenylsilyloxymethylbutyrolactone.

Selected spectral data for 2-(R)-hexyl-3-(R)-hydroxy-4-methyl-4-t-butyldiphenylsilyloxymethylbutyrolactone (major isomer at C-4)

$^1$H NMR (400 MHz, CDCl$_3$) δ 4.32 (dd, 1H), 3.71 (d, 1H), 3.67 (d, 1H), 2.60 (m, 1H), 1.95 (d, 1H), 1.26 (s, 3H), 1.05 (s, 9H).

Selected spectral data for 2-(R)-hexyl-3-(R)-hydroxy-4-methyl-4-t-butyldiphenylsilyloxymethylbutyrolactone (minor isomer at C-4)

$^1$H NMR (400 MHz, CDCl$_3$) δ 3.99 (dd, 1H), 3.89 (d, 1H), 3.76 (d, 1H), 2.90 (m, 1H), 1.95 (d, 1H), 1.28 (s, 3H), 1.07 (s, 9H).

Preparation of
1-Hydroxy-2-(S)-hexyl-3-(R)-hydroxy-4-hydroxy-4-methyl-5-t-butyldiphenylsilyloxypentane To a 50 ml round bottom flask was introduced a mixture of 62 mg (0.13 mmol) of 2-(R)-hexyl-3-(R)-hydroxy-4-methyl-4-t-butyldiphenylsilyloxymethylbutyrolactone (major isomer at C-4), to which was added 2 ml sieve dried THF and 0.270 ml of 1M LiBH$_4$ in THF (0.27 mmol, 2 eq.). The reaction was stirred at 50° C. for 24 hours, then added to 10 ml of water in a separatory funnel and the pH was adjusted to 3–5 with dilute HCl, at which point 10 ml of brine was added and the aqueous layer was extracted three times with 20 ml of methylene chloride. The organic layer was separated, dried over MgSO$_4$, and the solvent was removed under vacuum. The residue was chromatographed with 80% hexane/ethyl acetate. This afforded 40 mg (55%) of 1-hydroxy-2-(S)-hexyl-3-(R)-hydroxy-4-hydroxy-4-methyl-5-t-butyldiphenylsilyloxy-pentane.

Selected spectral data for 1-hydroxy-2-(S)-hexyl-3-(R)-hydroxy-4-hydroxy-4-methyl-5-t-butyldiphenylsilyloxypentane $^1$H NMR (400 MHz, CDCl$_3$) δ 7.65 (m, 4H), 7.40 (m, 6H), 4.32 (dd, 1H), 3.72 (d, 1H), 3.65 (m, 3H), 3.56 (d, 1H), 3.12 (br s, 1H), 2.78 (br m, 1H), 2.42 (d, 1H), 1.18 (s, 3H), 1.08 (s, 9H), 0.86 (br t, 3H), Preparation of
1-Hydroxy-2-(S)-hexyl-3-(R)-hydroxy-4-hydroxy-4-methyl-5-t-butyldiphenylsilyloxypentane
3-O,4-O-acetonide To a 50 ml round bottom flask was introduced a mixture of 7 mg (0.02 mmol) of 1-hydroxy-2-(S)-hexyl-3-(R)-hydroxy-4-hydroxy-4-methyl-5-t-butyldiphenylsilyloxypentane, to which was added 3 ml sieve dried acetone, 15 mg of pyridinium p-toluenesulfonate, and 25 mg anh. CuSO$_4$. The reaction was stirred at 85° C. for 24 hours, then the solvent was removed under reduced pressure, at which point 10 ml of brine/aq. sat. NaHCO$_3$ and 20 ml methylene chloride was added. The aqueous layer was extracted three times with 10 ml of methylene chloride. The combined organic layers were dried over MgSO$_4$, and the solvent was removed under vacuum. The residue was chromatographed with 80% hexane/ethyl acetate. This afforded 7 mg (95%) of 1-hydroxy-2-(S)-hexyl-3-(R)-hydroxy-4-hydroxy-4-methyl-5-t-butyldiphenylsilyloxypentane 3-O,4-O-acetonide.

Selected spectral data for 1-hydroxy-2-(S)-hexyl-3-(R)-hydroxy-4-hydroxy-4-methyl-5-t-butyldiphenylsilyloxypentane 3-O,4-O-acetonide $^1$H NMR (400 MHz, CDCl$_3$) δ 7.65 (m, 4H), 7.40 (m, 6H), 3.81 (d, 1H), 3.73 (d, 1H), 3.70 (m, 2H), 3.30 (d, 1H), 1.95 (m, 1H), 1.54 (s, 3H), 1.40 (s, 3H), 1.29 (s, 3H), 1.05 (s, 9H), 0.86 (br t, 3H), Preparation of
2-(S)-hexyl-3-(R)-hydroxy-4-hydroxy-4-methyl-5-t-butyldiphenylsilyloxypentanal 3-O,4-O-acetonide To a 50 ml round bottom flask was introduced a mixture of 7 mg (0.02 mmol) of 1-hydroxy-2-(S)-hexyl-3-(R)-hydroxy-4-hydroxy-4-methyl-5-t-butyldiphenylsilyloxypentane 3-O,4-O-acetonide, to which was added 1 ml sieve dried isopropyl acetate and 0.010 ml DMSO (ca. 10 eq.). The reaction was stirred at −25° C. and 25 ml of sieve dried triethylamine (ca. 12 eq) followed by 11 ml of phenyldichlorophosphate (ca. 5 eq.) The reaction was stirred at 0° C. for 5 hours, after which the reaction was introduced directly to a silica column and chromatographed with 90% hexane/ethyl acetate. This afforded 5 mg (70%) of 1-hydroxy-2-(S)-hexyl-3-(R)-hydroxy-4-hydroxy-4-methyl-5-t-butyldiphenylsilyloxypentanal 3-O,4-O-acetonide.

Selected spectral data for 1-hydroxy-2-(S)-hexyl-3-(R)-hydroxy-4-hydroxy-4-methyl-5-t-butyldiphenylsilyloxypentanal 3-O,4-O-acetonide $^1$H NMR (400 MHZ, CDCL$_3$) Δ 9.70 (D, 1H), 7.63 (D, 4H), 7.40 (M, 6H), 4.10 (D, 1H), 3.65 (D, 1H), 3.23 (D, 1H), 3.04 (M, 1H), 1.95 (M, 1H), 1.31 (S, 3H), 1.29 (S, 3H), 1.26 (S, 3H), 1.04 (S, 9H), 0.86 (BR T, 3H),

EXAMPLE 8

General Preparation of 2-(X)-alkyl-3-(X)-hydroxy-4-hydroxy-4-alkyl-5-t-butyl-diphenylsilyloxypentanal 3-O,4-O-acetonide (X=R or S)

Following the procedure given in example 7, a variety of 2-(X)-alkyl-3-(X)-hydroxy-4-hydroxy-4-alkyl-5-t-butyldiphenylsilyloxypentanal 3-O,4-O-acetonides (X=R or S) can be prepared. A representative but nonlimiting sampling of the compounds that can be produced in this manner include those in the following table:

TABLE 4-1

| Starting Material | Product |
| --- | --- |

TABLE 4-2

| Starting Materials | Protected End Products |
| --- | --- |

EXAMPLE 9

Preparation of 2-(R)-hexyl-3-(R)-hydroxy-4-hydroxy-4-methyl-5-t-butyldiphenylsilyloxypentanal 3-O,4-O-carbonate Preparation of 1-Triphenylmethoxy-2-(S)-hexyl-3-(R)-hydroxy-4-hydroxy-4-methyl-5-t-butyldiphenylsilyloxypentane 1-Hydroxy-2-(S)-hexyl-3-(R)-hydroxy-4-hydroxy-4-methyl-5-t-butyldiphenylsilyloxypentane (prepared as described in example 7) in dimethylformamide is reacted with triphenylmethyl chloride in the presence of 4-N,N-dimethylaminopyridine according to Greene & Wuts, *Protecting Groups in Organic Synthesis*, 2nd ed., John Wiley & Sons, Inc. New York, 1991, p. 60 to afford 1-triphenylmethoxy-2-(S)-hexyl-3 -(R)-hydroxy-4-hydroxy-4-methyl-5-t-butyldiphenylsilyloxypentane.

Preparation of 1-Triphenylmethoxy-2-(S)-hexyl-3-(R)-hydroxy-4-hydroxy-4-methyl-5-t-butyldiphenylsilyloxypentane 3-O,4-O-carbonate 1-Triphenylmethoxy-2-(S)-hexyl-3-(R)-hydroxy-4-hydroxy-4-methyl-5-t-butyldiphenylsilyloxypentane in pyridine is reacted with phosgene according to Greene & Wuts, *Protecting Groups in Organic Synthesis*, 2nd ed., John Wiley & Sons, Inc. New York, 1991, p. 140 to afford 1-triphenylmethoxy-2-(S)-hexyl-3-(R)-hydroxy-4-hydroxy-4-methyl-5-t-butyldiphenylsilyloxypentane 3-O,4-O-carbonate.

Preparation of 1-Hydroxy-2-(S)-hexyl-3-(R)-hydroxy-4-hydroxy-4-methyl-5-t-butyldiphenylsilyloxypentane 3-O,4-O-carbonate Cleavage of the trityl group from 1-triphenylmethoxy-2-(S)-hexyl-3-(R)-hydroxy-4-hydroxy-4-methyl-5-t-butyldiphenylsilyloxy-pentane 3-O,4-O-carbonate according to Greene & Wuts, *Protecting Groups in Organic Synthesis*, 2nd ed., John Wiley & Sons, Inc. New York, 1991, p. 61 to afford 1-hydroxy-2-(S)-hexyl-3-(R)-hydroxy-4-hydroxy-4-methyl-5-t-butyldiphenylsilyloxypentane 3-O,4-O-carbonate.

Preparation of 2-(S)-Hexyl-3-(R)-hydroxy-4-hydroxy-4-methyl-5-t-butyldiphenylsilyloxypentanal 3-O,4-O-carbonate 1-Hydroxy-2-(S)-hexyl-3-(R)-hydroxy-4-hydroxy-4-methyl-5-t-butyldiphenylsilyloxypentane 3-O,4-O-carbonate is oxidized to 2-(S)-hexyl-3-(R)-hydroxy-4-hydroxy-4-methyl-5-t-butyldiphenylsilyloxy-pentanal 3-O,4-O-carbonate using DMSO and phenyldichlorophosphate with triethylamine in methylene chloride as described in example 7.

EXAMPLE 10

General Preparation of 2-(X)-alkyl-3-(X)-hydroxy-4-hydroxy-4-alkyl-5-t-butyldiphenylsilyloxypentanal 3-O,4-O-carbonate (X=R or S)

Following the procedure given in example 9, a variety of 2-(X)-alkyl-3-(X)-hydroxy-4-hydroxy-4-alkyl-5-t-butyldiphenylsilyloxy-pentanal 3-O,4-O-carbonates (X=R or S) can be prepared. A representative but nonlimiting sampling of the compounds that can be produced in this manner include those in the following table:

TABLE 5-1

| Starting Material | Product |
|---|---|
| 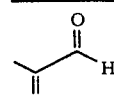 | 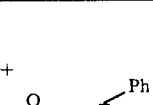 |

TABLE 5-1-continued

| Starting Material | Product |
|---|---|
| 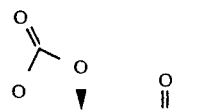 | 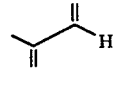 |
| 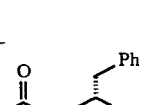 | 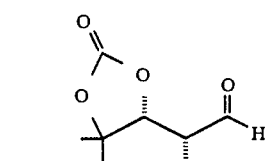 |
| 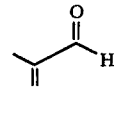 | 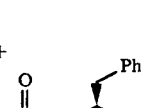 |

TABLE 5-2

| Starting Materials | Products |
|---|---|
| 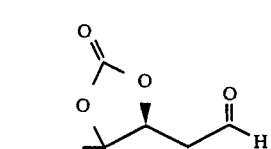 | 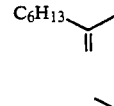 |
| 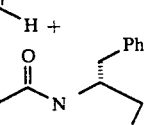 | 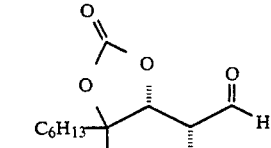 |
| 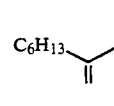 | 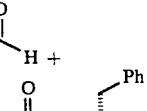 |

EXAMPLE 11

Preparation of 2-(R)-Methyl-3-(S)-alkoxy-4-(S)-methyl-5-t-butyldimethylsilyloxypentanal

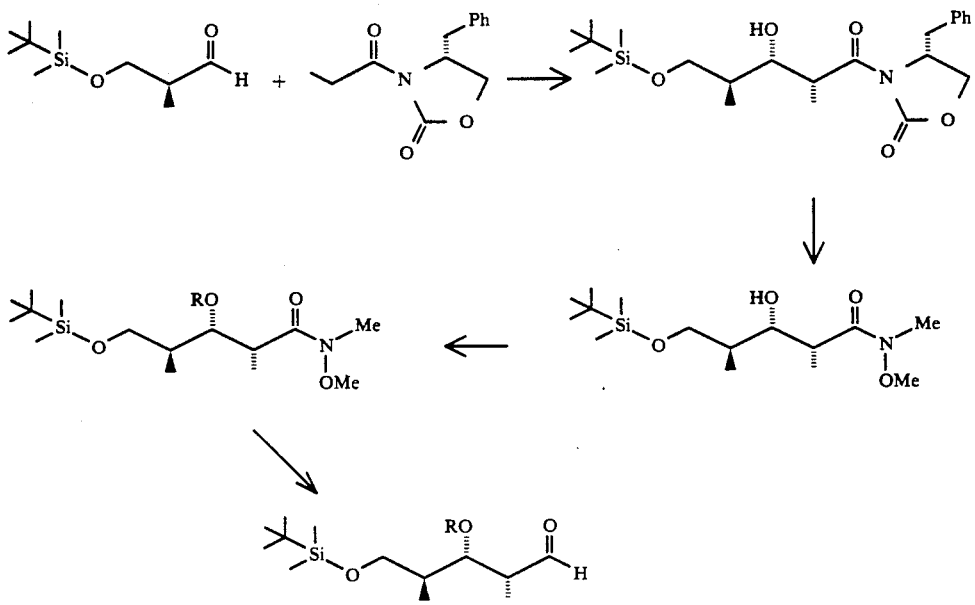

Preparation of 3-(1-Oxo-2-(R)-methyl-3-(R)-hydroxy-4-(S)-methyl-5-t-butyldimethylsiloxypentyl)-4-(R)-(phenylmethyl)-2-oxazolidinone This material is prepared from (R)-3-(1-oxopropyl)-4-(phenylmethyl)-2-oxazolidinone and 2-(S)-methyl-3-t-butyldimethylsiloxypropanal following the method of Evans and Gage, as described in *Org. Syn.*, Vol. 68, 19xx, p. 83.

Preparation of N-Methoxy-N-methyl-2-(R)-methyl-3-(R)-hydroxy-4-(S)-methyl-5-t-butyldimethylsiloxypentanamide This material is prepared from 3-(1-oxo-2-(R)-methyl-3-(R)-hydroxy-4-(S)-methyl-5-t-butyldimethylsiloxypentyl)-4-(R)-(phenyl-methyl)-2-oxazolidinone following the procedure described by Weinreb et al. in *Tetrahedron Lett.* 1977, 4171 and *Synth. Commun.* 1982, 12, 989.

Preparation of N-Methoxy-N-methyl-2-(R)-methyl-3-(R)-benzyloxy-4-(S)-methyl-5-t-butyldimethylsiloxypentanamide This material is prepared from N-methoxy-N-methyl-2-(R)-methyl-3-(R)-hydroxy-4-(S)-methyl-5-t-butyldimethylsiloxypentanamide using the reagent benzyltrichloroacetimidate and following the procedure described by Bundle et al. in *J. C. S. Chem. Comm.* 1981, 1240.

Preparation of 2-(R)-Methyl-3-(R)-benzyloxy-4-(S)-methyl-5-t-butyldimethylsiloxypentanal This material is prepared from N-methoxy-N-methyl-2-(R)-methyl-3-(R)-benzyloxy-4-(S)-methyl-5-t-butyldimethylsiloxypentanamide following the procedure described by Weinreb et al. in *Tetrahedron Lett.* 1977, 417 1.

EXAMPLE 12

General Preparation of 2-(X)-alkyl-3-(X)-alkoxy-4-substituted-5-t-butyldimethylsilyloxypentanals (X=R or S)

Following the procedure given in example 11, a variety of 2-(X)-alkyl-3-(X)-alkoxy-4-substituted-5-t-butyldimethylsilyloxypentanals (X=R or S) can be prepared. A representative but nonlimiting sampling of the compounds that can be produced in this manner include those in the following table:

TABLE 6-1

| Starting Materials | Products |
|---|---|

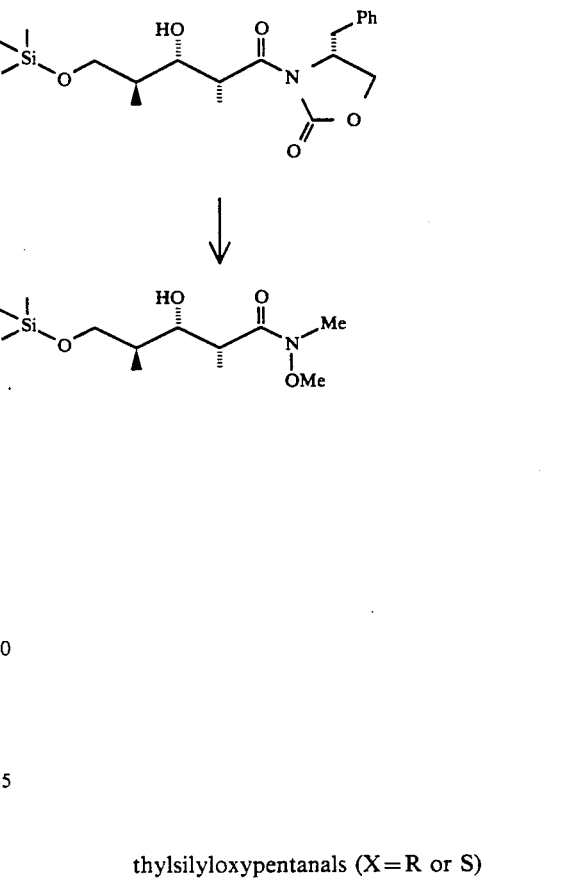

TABLE 6-1-continued
| Starting Materials | Products |
|---|---|
| 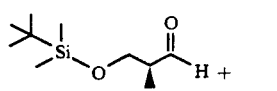 | 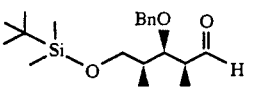 |
| 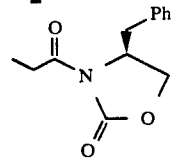 |  |
| 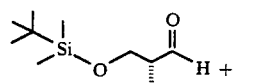 | 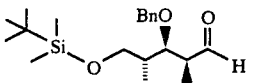 |
| 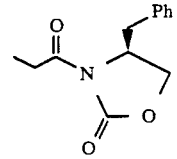 |  |
| 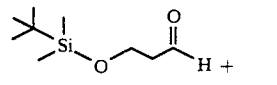 | 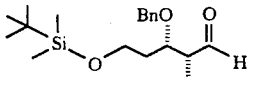 |
TABLE 6-2
| Starting Materials | Products (R = Me, Bn) |
|---|---|
| 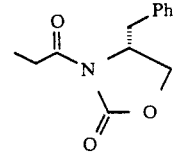 |  |
TABLE 6-2-continued
| Starting Materials | Products (R = Me, Bn) |
|---|---|
| 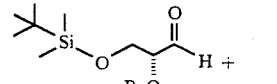 | 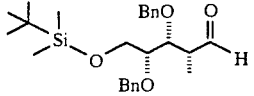 |
| 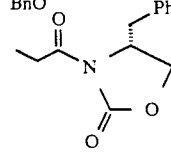 |  |
| 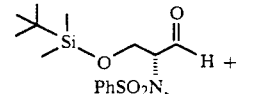 | 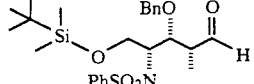 |
| 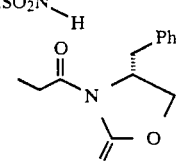 | 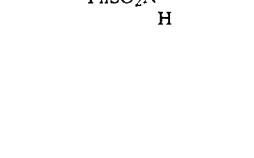 |
| 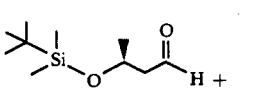 | 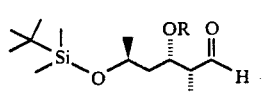 |

TABLE 6-2-continued
| Starting Materials | Products (R = Me, Bn) |
|---|---|
| 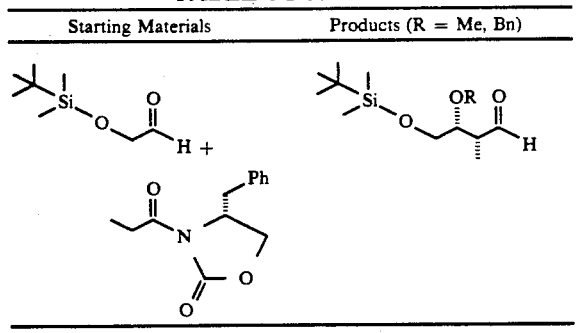 | |
EXAMPLE 13
Preparation of 8a-methyl-8a-aza-9-deoxo-10-demethyl-11-deoxy-12,13,14,15-tetrakisnor-8a-homoerythromycin A
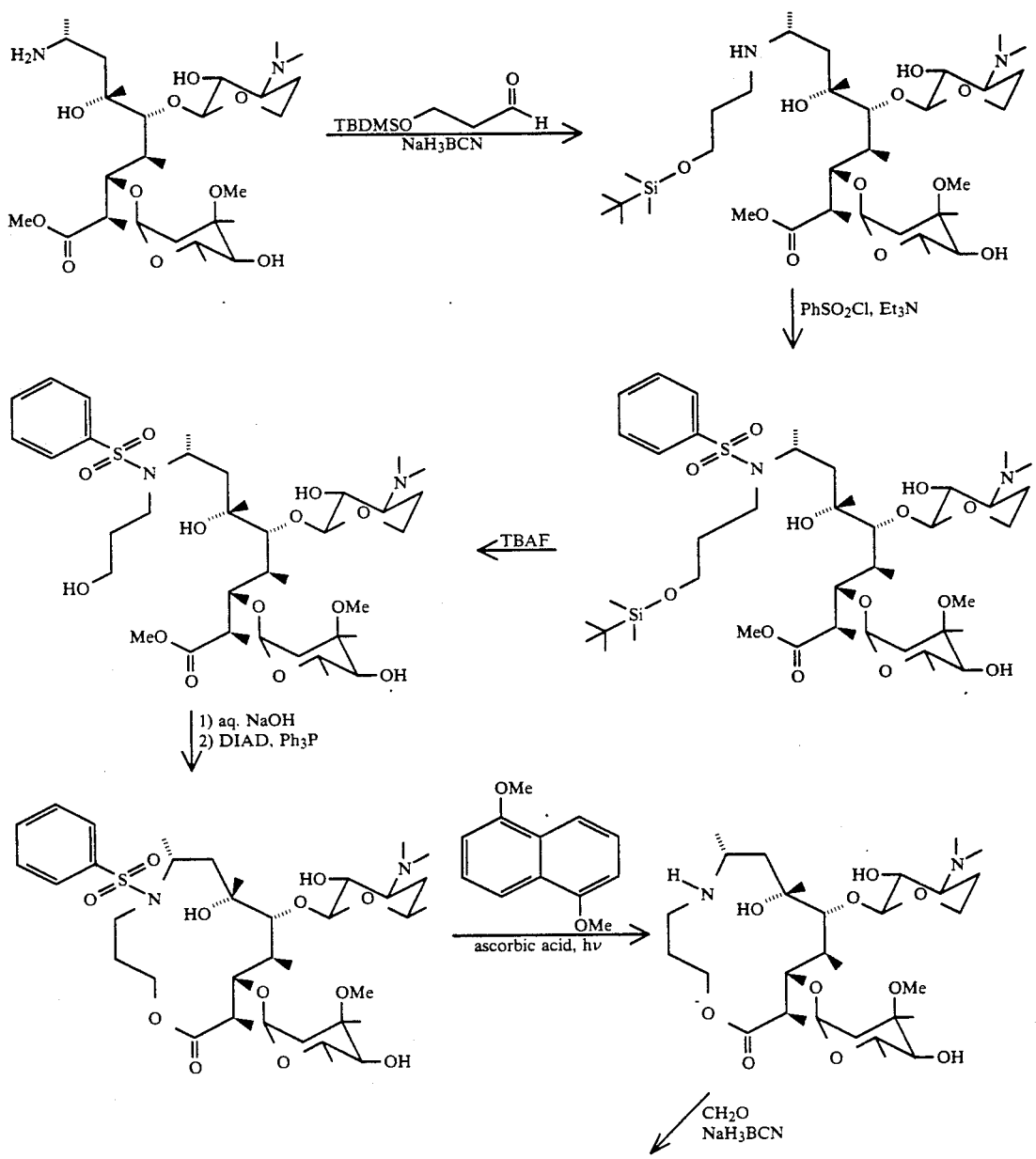

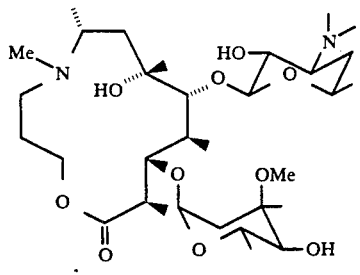

15

Preparation of 8a-(3-t-butyldimethylsilyloxypropyl)-8a-aza-9,10,11,12,13,14,15-heptanor-8a-homoerythromycin To a 100 ml round bottom flask was introduced 370 mg (0.625 mmol) of 8a-aza-9,10,11,12,13,14,15-heptanor-8a-homoerythromycin A, to which was added 15 ml MeOH, 135 mg (0.720 mmol, 1.15 eq.) of the aldehyde starting material, 3-(t-butyldimethylsilyloxy)-propanaldehyde 65 mg $NaH_3BCN$ (0.97 mmol, 1.55 eq.), and 0.400 ml of AcOH. The reaction was stirred at room temperature and monitored by TLC (93:7:1 $CH_2Cl_2$/MeOH/aq. $NH_3$, product is higher $R_f$ than starting material). After 24 hours, the reaction was not complete as judged by TLC, and 65 mg more $NaH_3BCN$ (0.97 mmol, 1.55 eq.) was added. After stirring an additional 10 hours, only a small amount of starting material remained as judged by TLC. The solvent was removed under vacuum and the residue was taken up in 95:5:1 $CH_2Cl_2$/MeOH/aq. $NH_3$ and chromatographed on silica gel using the same solvent mixture. This afforded 282 mg (59%) of the desired product.

Selected spectral data for 8a-(3-t-butyldimethylsilyloxypropyl)-8a-aza-9,10,11,12,13,14,15-heptanor-8a-homoerythromycin A:

$^1H$ NMR (400 MHz, $CDCl_3$) δ 4.62 (d, H-1″), 4.32 (d, H-1′), 4.06 (dd, H-3), 3.96 (m, H-5″), 3.64 (s; $COOCH_3$), 3.68 (t, H-11), 3.49 (H-5), 3.30 (H-2′), 3.24 (s, $OCH_3$), 2.96 (d, H-4″), 2.78 (dq, H-2), 2.51 (m, H-3′), 2.27 (s, $N(CH_3)_2$), 1.28 & 1.18 (singlets, 6-Me and 3″-Me), 1.36, 1.21, 1.20, 1.13 & 1.04 (methyl doublets), 0.85 & 0.02 (singlets, TBDMS).

FAB MS: 766 ($M+H^+$)

Preparation of 8a-(3-t-butyldimethylsilyloxypropyl)-8a-benzenesulfonyl-8a-aza-9,10,11,12,13,14,15-heptanor-8a-homoerythromycin A To a 100 ml round bottom flask was introduced 282 mg (0.369 mmol) of 8a-(3-t-butyldimethylsilyloxypropyl)-8a-aza-9,10,11,12,13,14,15-heptanor-8a-homoerythromycin A, to which was added 5 ml $CH_2Cl_2$, 0.85 ml triethylamine and 0.280 ml of benzenesulfonyl chloride (2.20 mmol, 6.0 eq.). The reaction was stirred at room temperature and monitored by TLC (93:7:1 $CH_2Cl_2$/MeOH/aq. $NH_3$, product is higher $R_f$ than starting material). After 2 hours, the reaction was judged to be complete by TLC. The solvent was removed under vacuum and the residue was taken up in 94:6:1 $CH_2Cl_2$/MeOH/aq. $NH_3$ and chromatographed on silica gel using the same solvent mixture. This afforded 235 mg of the desired product (70%).

Selected spectral data for 8a-(3-t-butyldimethylsilyloxypropyl)-8a-benzenesulfonyl-8a-aza-9,10,11,12,13,14,15-heptanor-8a-homoerythromycin A:

$^1H$ NMR (400 MHz, $CDCl_3$) δ 7.87 (d, $C_6H_5SO_2$—), 7.45 (m, $C_6H_5SO_2$—), 4.57 (d, H-1″), 4.33 (d, H-1′), 4.33 (m, H-9), 4.08 (dd, H-3), 3.99 (m, H-5″), 3.67 (s, $COOCH_3$), 3.59 (t, H-11), 3.31 (dd, H-2′), 3.23 (s, $OCH_3$), 2.95 (br t, H-4″), 2.55 (dq, H-2), 2.54 (m, H-3′), 2.28 (s, $N(CH_3)_2$), 2.24 (d, H-2″), 1.21 & 1.17 (singlets, 6-Me and 3″-Me), 1.27, 1.19, 1.09, 1.03 & 1.02 (methyl doublets), 0.80 & 0.01 (singlets, TBDMS).

$^{13}C$ NMR (100 MHz, $CDCl_3$) δ 176.0, 140.9, 132.0, 128.7, 127.4, 105.3, 96.2, 87.3, 79.8, 77.8, 73.2, 72.7, 70.4, 69.9, 65.5, 65.0, 60.7, 51.8, 50.0, 49.4, 44.5, 41.5, 41.4, 40.3, 37.6, 35.2, 34.5, 28.9, 25.9, 24.4, 21.6, 21.2, 17.8, 10.7, 9.7, −5.4.

FAB MS: 905 ($M+H^+$)

Preparation of 8a-(3-hydroxypropyl)-8a-benzenesulfonyl-8a-aza-9,10,11,12,13,14,15-heptanor-8a-homoerythromycin A To a 100 ml round bottom flask was introduced 235 mg (0.260 mmol) of 8a-(3-t-butyldimethylsilyloxypropyl)-8a-benzenesulfonyl-8a-aza-9,10,11,12,13,14,15-heptanor-8a-homoerythromycin A, to which was added 10 ml THF dried over 3 A molecular sieves, and 0.470 ml 1M tetrabutylammonium fluoride in THF (0.470 mmol, 1.8 eq.). The reaction was stirred at room temperature and monitored by TLC (93:7:1 $CH_2Cl_2$/MeOH/aq. $NH_3$, product is lower $R_f$ than starting material). After 24 hours, the reaction was judged to be complete by TLC. After the solvent was removed under vacuum, the residue was taken up in 95:5:1 $CH_2Cl_2$/MeOH/aq. $NH_3$ and chromatographed on silica gel using the same solvent mixture. NMR revealed that the chromatographed material was contaminated with tetrabutylammonium salts. This afforded 174 mg (85% yield) of the desired product.

Selected spectral data for 8a-(3-hydroxypropyl)-8a-benzenesulfonyl-8a-aza-9,10,11,12,13,14,15-heptanor-8a-homoerythromycin A:

$^1H$ NMR (400 MHz, $CDCl_3$) δ 7.85 (d, $C_6H_5SO_2$—), 7.45 (m, $C_6H_5SO_2$—), 4.60 (d, H-1″), 4.32 (d, H-1′), 4.30 (m, H-9), 4.04 (m, H-3), 3.98 (m, H-5″), 3.64 (s, $COOCH_3$), 3.55 (m, H-11), 3.32 (H-5), 3.28 (d, H-2′), 3.23 (s, $OCH_3$), 2.95 (br t, H-4″), 2.60 (dq, H-2), 2.48 (m, H-3′), 2.26 (s, $N(CH_3)_2$), 2.23 (d, H-2″), 1.18 & 1.15 (singlets, 6-Me and 3″-Me), 1.23, 1.17, 1.09, 1.05 & 1.01 (methyl doublets).

FAB MS: 792 ($M+H^+$)

Preparation of
8a-benzenesulfonyl-8a-aza-9-deoxo-10-demethyl-11-deoxy-12,13,14,15-tetrakisnor-8a-homoerythromycin A To a 100 ml round bottom flask was introduced 174 mg (0.220 mmol) of 8a-(3-hydroxypropyl)-8a-benzenesulfonyl-8a-aza-9,10,11,12,13,14,15-heptanor-8a-homoerythromycin A, to which was added 8.5 ml THF, 4.5 ml MeOH and 1.6 ml 1N NaOH (1.6 mmol, 7.3 eq.). The reaction was stirred at room temperature and monitored by TLC (93:7:1 $CH_2Cl_2$/MeOH/aq. $NH_3$, product is baseline). After 36 hours, the reaction was judged to be complete by TLC. The reaction mixture was diluted with 25 ml water and brought to pH=7 with aq. HCl. The solvent was removed under vacuum and the residue was dried for 12 hours under high vacuum. To the residue was added 150 ml of dry THF and the flask was sonicated for 5 minutes to insure proper mixing. To this cloudy mixture was added 370 mg (1.42 mmol, 6.4 eq.) of triphenylphosphine followed by 0.260 ml (267 mg, 1.32 mmol, 6.0 eq.) diisopropyl azodicarboxylate. The reaction was stirred at room temperature and monitored by TLC (93:7:1 $CH_2Cl_2$/MeOH/aq. $NH_3$, product is mid $R_f$.) After 1 hour the reaction was judged to be complete by TLC (no material remained at the baseline). The solvent was removed under vacuum and the residue was taken up in 94:6:1 $CH_2Cl_2$/MeOH/aq. $NH_3$ and chromatographed on silica gel using the same solvent mixture. This afforded 125 mg (75%) of the desired product.

Selected spectral data for 8a-benzenesulfonyl-8a-aza-9-deoxo-10-demethyl-11-deoxy-12,13,14,15-tetrakisnor-8a-homoerythromycin A:

$^1$H NMR (400 MHz, $CDCl_3$) δ 7.87 (d, $C_6H_5SO_2$—), 7.45 (m, $C_6H_5SO_2$—), 4.63 (d, H-1''), 4.40, 4.35 & 3.83 (multiplets, H-9 and H13), 4.36 (d, H-1'), 4.18 (m, H-3), 3.93 (m, H-5''), 3.50 (m, H-5'), 3.49 (m, H-5), 3.26 (s, $OCH_3$), 2.98 (t, H-4''), 2.57 (dq, H-2), 2.46 (m, H-3''), 2.30 (d, H-2''), 2.27 (s, N($CH_3$)$_2$), 1.64 (br d, H-4'), 1.19 & 1.15 (singlets, 6-Me and 3''-Me), 1.21, 1.15, 1.11, 1.09 & 1.05 (methyl doublets).

$^{13}$C NMR (100 MHz, $CDCl_3$) δ 175.8, 141.1, 132.2, 128.8, 127.2, 103.9, 96.1, 87.1, 78.6, 77.7, 73.9, 72.7, 70.5, 69.6, 65.6, 65.2, 62.6, 51.3, 49.3, 44.9, 43.4, 42.9, 40.4, 34.7, 30.2, 28.9, 23.0, 21.5, 21.1, 17.8, 12.9, 9.6.

FAB MS: 760 (M+H+)

Preparation of
8a-aza-9-deoxo-10-demethyl-11-deoxy-12,13,14,15-tetrakisnor-8a-homoerythromycin A To a 4 ml screw cap borosilicate glass vial was introduced 33 mg (0.046 mmol) of 8a-benzenesulfonyl-8a-aza-9-deoxo-10-demethyl-11 -deoxy-12,13,14,15-tetrakisnor-8a-homoerythromycin A, 35 mg of 1,5-dimethoxynaphthalene, 25 mg of ascorbic acid and 3.5 ml of 95% ethanol. The solution was stirred magnetically, cooled under a vigorous stream of air, and irradiated with a high pressure Hanovia lamp. After 1 hour, the reaction was judged to be complete by thin layer chromatography (94:6:1 $CH_2Cl_2$/MeOH/aq. $NH_3$, product is lower $R_f$ than starting material). The reaction was added to 150 ml of methylene chloride and extracted with 0.1N aq. NaOH. The organic layer was dried over $MgSO_4$ and concentrated under vacuum. The residue was taken up in 94:6:1 $CH_2Cl_2$/MeOH/aq. $NH_3$ and chromatographed on silica gel using the same solvent mixture. This afforded 16 mg (59%) of the desired product.

Selected spectral data for 8a-aza-9-deoxo-10-demethyl-11-deoxy-12,13,14,15-tetrakisnor-8a-homoerythromycin A:

$^1$H NMR (400 MHz, $CDCl_3$) δ 4.77 (d, H-1''), 4.35 (d, H-1'), 4.21 (d, H-3), 4.15 & 4.0 (m, H-9 and/or 11), 4.00 (m, H-5''), 3.48 (d, H-5), 3.45 (m, H-5'), 3.28 (s, $OCH_3$), 3.19 (dd, H-2'), 3.00 (t, H-4''), 2.70 (dq, H-2), 2.43 (m, H-3'), 2.33 (d, H-2''), 2.25 (s, N($CH_3$)$_2$), 1.37 & 1.20 (singlets, 6-Me and 3''-Me), 1.28, 1.19, 1.11, 1.10 & 1.07 (methyl doublets).

High resolution FAB MS: MH+=619.4194 (error=2.5 mmu)

Elemental analysis: Calcd for $C_{31}H_{58}N_2O_{10}·H_2O$: C, 58.47; H, 9.50; N, 4.40. Found: C, 58.32; H, 9.13; N, 4.41.

Preparation of
8a-methyl-8a-aza-9-deoxo-10-demethyl-11-deoxy-12,13,14,15-tetrakisnor-8a-homoerythromycin A:

To a 50 ml round bottom flask was introduced 11 mg (0.018 mmol) of 8a-aza-9-deoxo-10-demethyl-11-deoxy-12,13,14,15-tetrakisnor-8a-homoerythromycin A, to which was added 2 ml MeOH, 0.050 ml 37% aq. formaldehyde (ca. 0.6 mmol, 34 eq.), and 15 mg sodium cyanoborohydride (0.238 mmol, 13 eq.). The reaction was stirred at room temperature and monitored by TLC (93:7:1 $CH_2Cl_2$/MeOH/aq. $NH_3$). After 1 hour, TLC showed complete converstion to a higher $R_f$ spot. The reaction was added to 50 ml of $CH_2Cl_2$ and extracted with 0.1N NaOH. The organic layer was dried over $MgSO_4$ and concentrated under vacuum. The residue was taken up in 94:6:1 $CH_2Cl_2$/MeOH/aq. $NH_3$ and chromatographed on silica gel using the same solvent mixture. This afforded 8 mg (72%) of the desired product.

Selected spectral data for 8a-methyl-8a-aza-9-deoxo-10-demethyl-11-deoxy- 12,13,14,15-tetrakisnor-8a-homoerythromycin $^1$H NMR (400 MHz, $CDCl_3$) δ 4.78 (d, H-1''), 4.36 (d, H-1'), 4.18 (d, H-3), 3.9 (m, H-11), 3.9 (m, H-5''), 3.49 (d, H-5), 3.44 (m, H-5'), 3.29 (s, $OCH_3$), 3.19 (dd, H-2'), 3.01 (br t, H-4''), 2.71 (dq, H-2), 2.46 (m, H-3'), 2.34 (d, H-2''), 2.28 (s, N($CH_3$)$_2$), 2.21 (s, ring N-$CH_3$), 1.40 & 1.20 (singlets, 6-Me and 3''-Me), 1.28, 1.20, 1.10, 1.08 & 0.91 (methyl doublets).

High resolution FAB MS: MH+=633.4312 (error=-1.5 mmu)

Elemental analysis: Calcd for $C_{31}H_{58}N_2O_{10}·\frac{1}{2}H_2O$: C, 59.88; H, 9.58; N, 4.36. Found: C, 59.64; H, 9.35; N, 4.37.

EXAMPLE 14

General Preparation of 13-Membered Azalides

Following the procedure given in example 13, 8a-aza-8a-homo-9,10,11,12,13,14,15-heptanorerythromycin A and various trialkylsiloxyaldehydes (which may be prepared as taught in examples 1 through 4) are used as starting materials for 13-membered azalides, as diagrammed below:

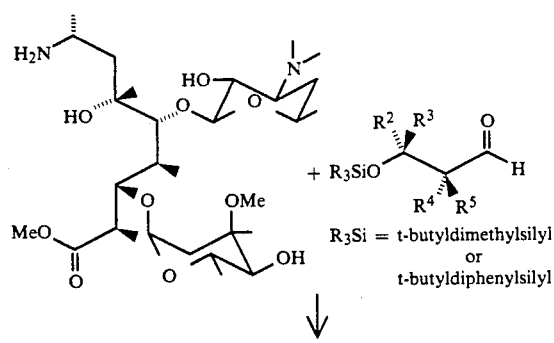
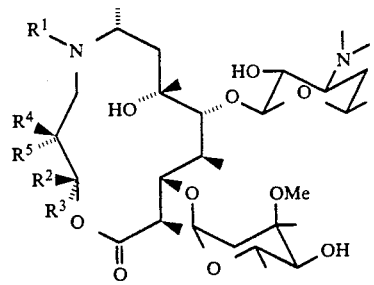
Examples of the compounds of the invention that can be produced in this manner include those in the following table:
| TABLE 7-1 | |
|---|---|
| aldehyde | macrocycle (R' = PhSO$_2$—, H or Me) |
| 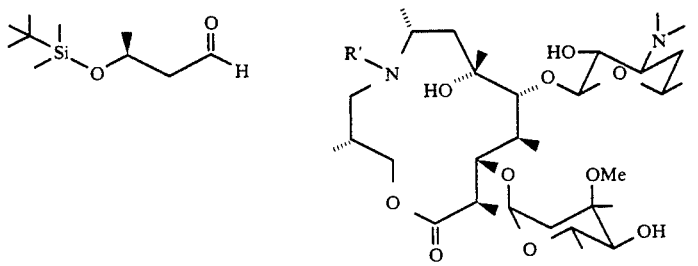 | |
| 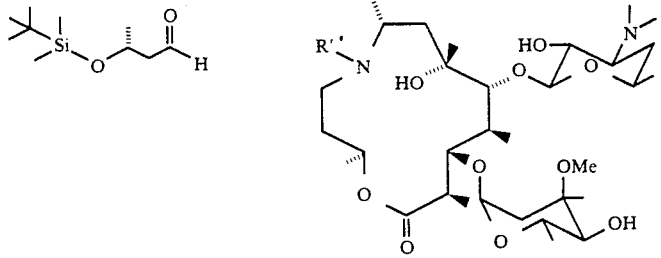 | |
| Bn = benzyl 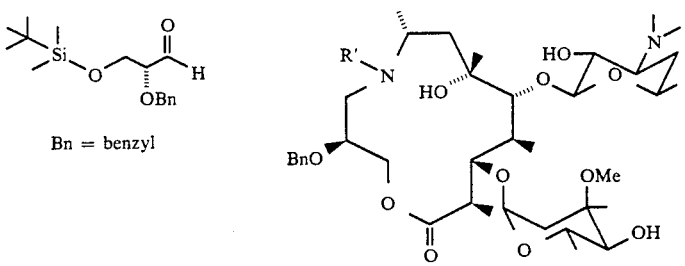 | |
| 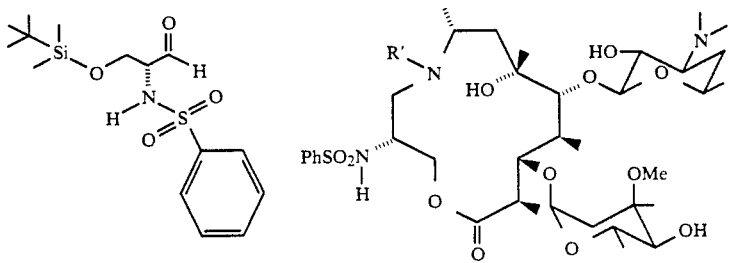 | |

TABLE 7-1-continued
| aldehyde | macrocycle (R' = PhSO$_2$—, H or Me) |
|---|---|
| 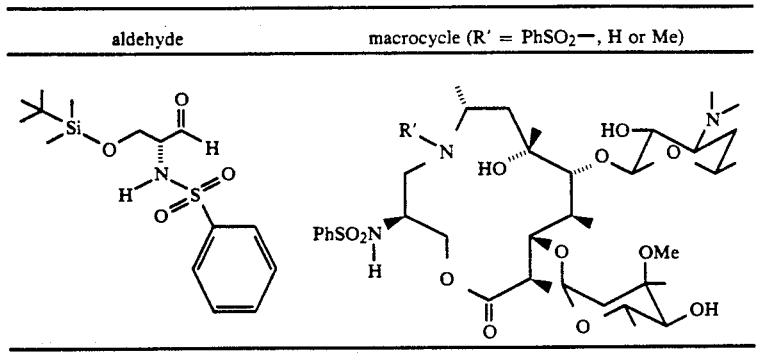 | |
TABLE 7-2
| aldehyde | macrocycle (R' = PhSO$_2$—, H or Me) |
|---|---|
| 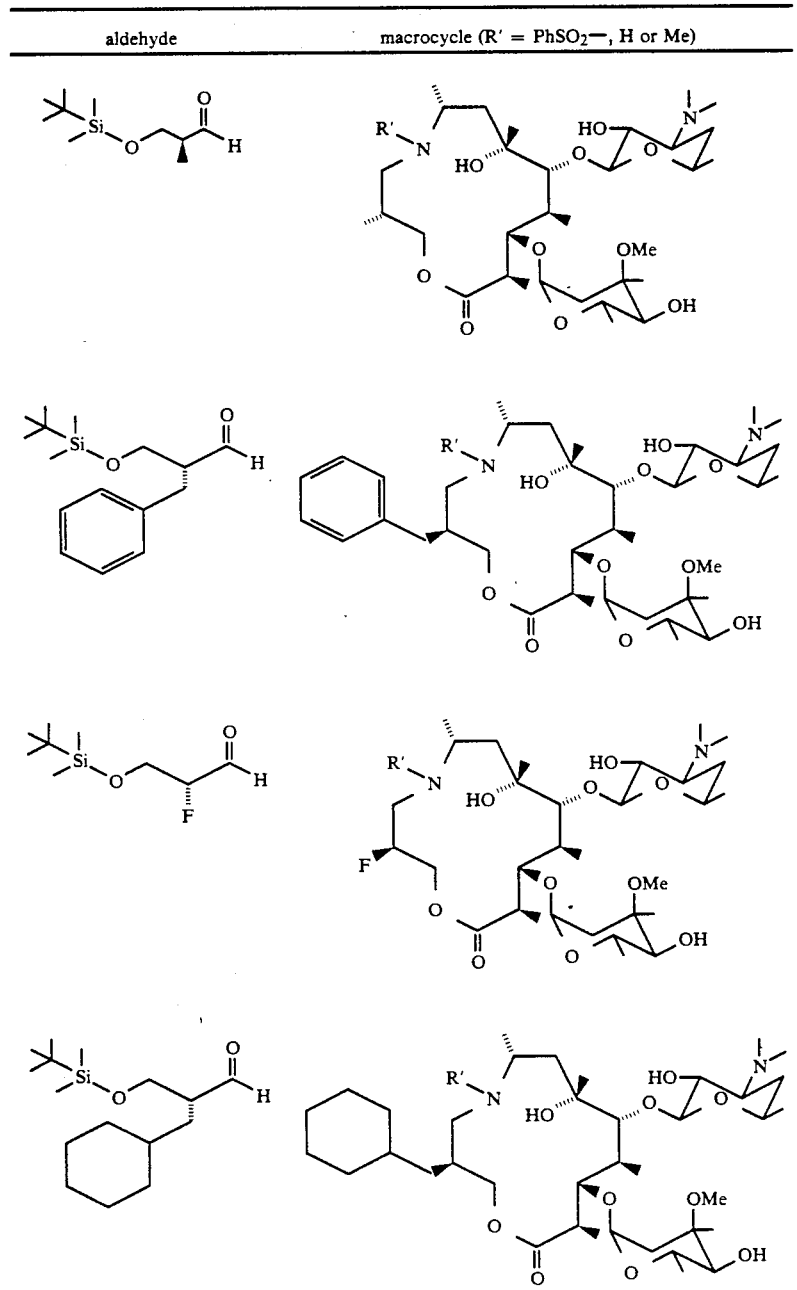 | |

TABLE 7-2-continued

| aldehyde | macrocycle (R' = PhSO$_2$—, H or Me) |
|---|---|
| 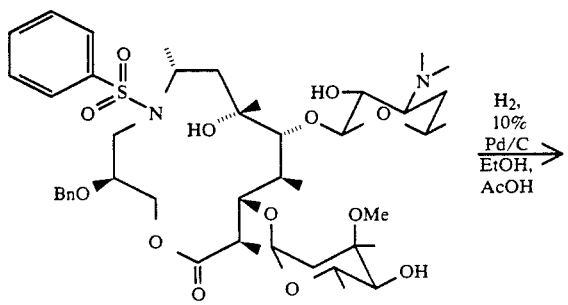 | |

EXAMPLE 15

Preparation of 8a-benzenesulfonyl-8a-aza-9-deoxo-10-demethyl-10-(S)-hydroxy-11-deoxy-12,13,14,15-tetrakisnor-8a-homoerythromycin A

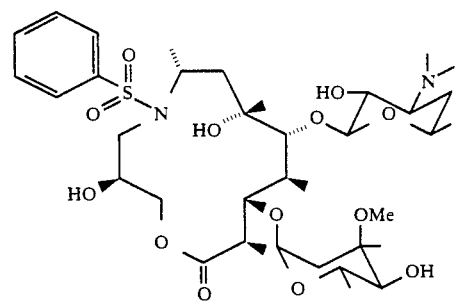

To a 100 ml round bottom flask was introduced 15 mg (0.019 mmol) of 8a-benzenesulfonyl-8a-aza-9-deoxo-10-demethyl-10-(S)-benzyloxy-11-deoxy-12,13,14,15-tetrakisnor-8a-homoerythromycin A, to which was added 4 ml 95% EtOH, 0.250 ml of AcOH and 50 mg of 10% Pd/C. The reaction was evacuated and filled with H$_2$, then stirred vigorously at room temperature. After 24 hours, TLC (93:7:1 CH$_2$Cl$_2$/MeOH/aq. NH$_3$) showed complete conversion to lower R$_f$ product. The reaction mixture was centrifuged and decanted away from the catalyst, added to 100 ml of CH$_2$Cl$_2$, and extracted twice with 0.1N aq. NaOH. The organic phase was dried with MgSO$_4$, and the solvent was removed under vacuum. The residue was taken up in 94:6:1 CH$_2$Cl$_2$/MeOH/aq. NH$_3$ and chromatographed on silica gel using the same solvent mixture. This afforded 5 mg (38%) of the desired product.

Selected spectral data for 8a-benzenesulfonyl-8a-aza-9-deoxo-10-demethyl-10-(S)-hydroxy-11-deoxy-12,13,14,15-tetrakisnor-8a-homo-erythromycin A:

$^1$H NMR (400 MHz, CDCl$_3$) δ 7.89 (d, 8.6 Hz, 2H), 7.5 (m, 3H), 4.71 (dd, J=6.1 Hz, 11 Hz), 4.66 (d, J=4.4 Hz, H-1″), 4.56 (br s, 1H), 4.35 (d, J=7.3 Hz, H-1′), 4.33 (br m, 1H), 4.16 (br m, 1H), 3.94 (m, H-5″), 3.82 (br s, 1H), 3.75 (d, J=11.4 Hz, H-1′), 3.50 (m, H-5′), 3.40 (dd, J=6.5 Hz, 9.44 Hz, 1H), 3.30 (d, J=8.0 Hz, 1H), 3.27 (s, OCH$_3$), 2.97 (br t, H-4″), 2.33 (s, N(CH$_3$)$_2$), 1.20 & 1.12 (singlets, 6-Me and 3″-Me), 1.21 (J=6.1), 1.16, 1.15, 1.13 & 1.09 (J=7.0) (methyl doublets).

High Res FAB MS: MH$^+$=775.4055 (error=0.4 mmu)

Elemental analysis: Calcd for C$_{37}$H$_{62}$N$_2$O$_{13}$S.H$_2$O: C, 56.04; H, 8.14; N, 3.53. Found: C, 56.30; H, 8.10; N, 3.74.

EXAMPLE 16

Preparation of 8a-methyl-8a-aza-9-deoxo-10-demethyl-11-deoxy-12-demethyl-12-deoxy-13,14,15-trisnor-8a-homoerythromycin A

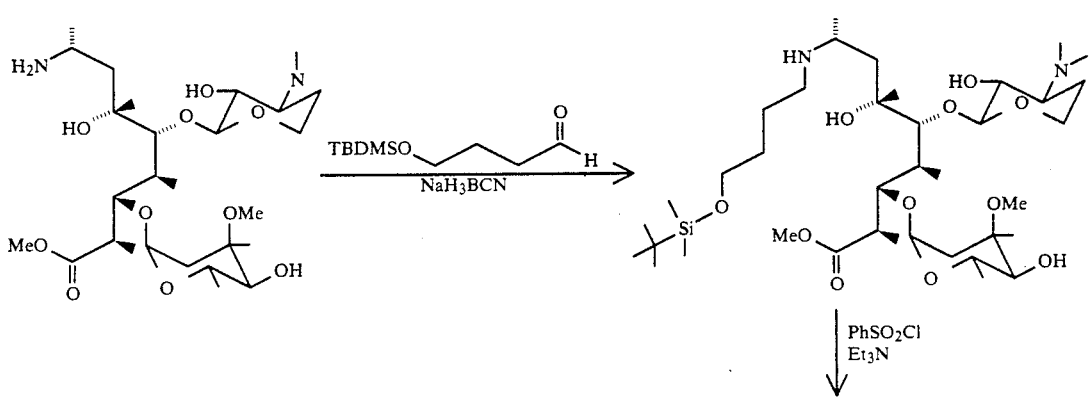

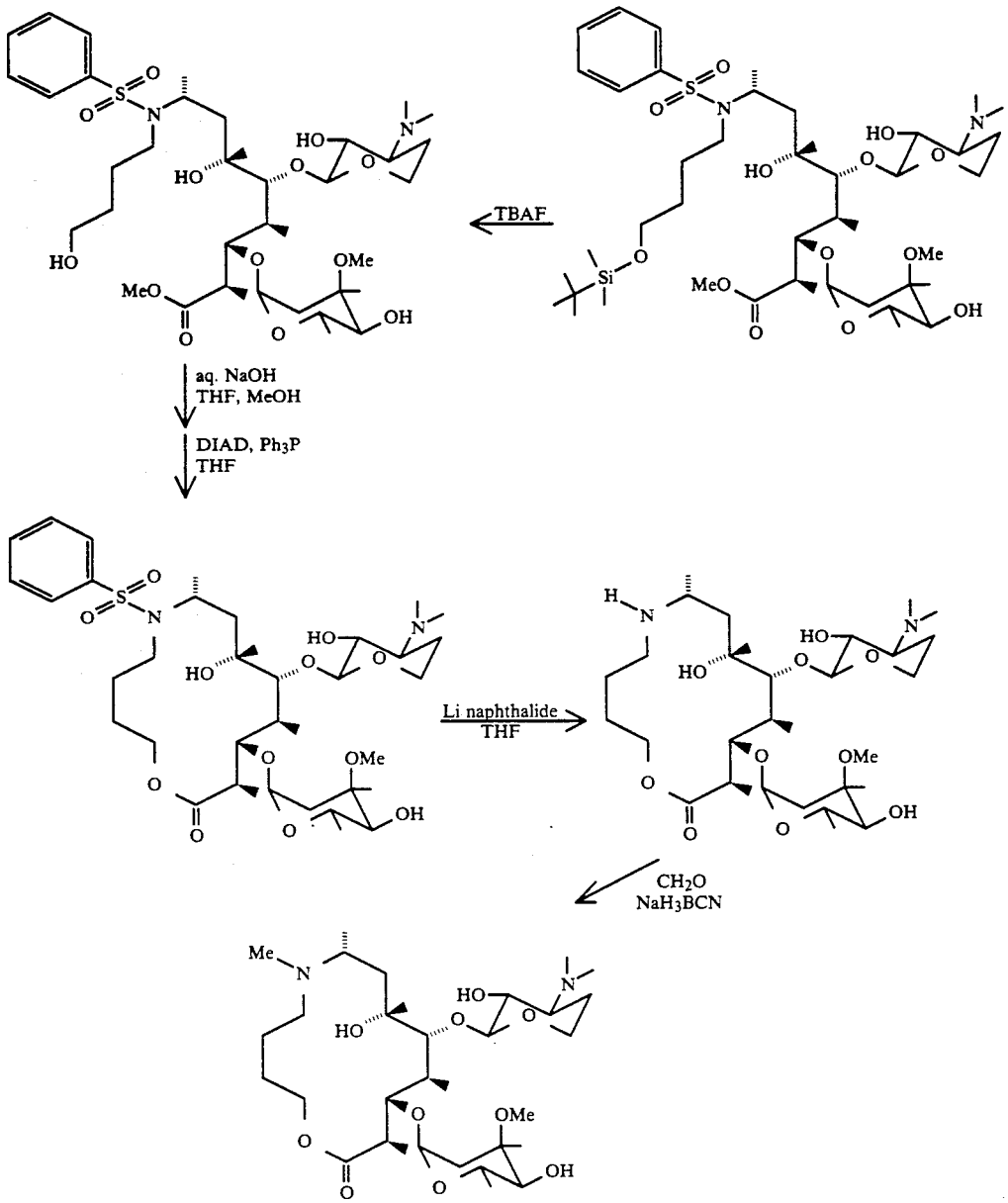

Preparation of 8a-(4-t-butyldimethylsilyloxybutyl)-8a-aza-9,10,11,12,13,14,15-heptanor-8a-homoerythromycin A To a 100 ml round bottom flask was introduced 370 mg (0,625 mmol) of 8a-aza-9,10,11,12,13,14,15-heptanor-8a-homoerythromycin A to which was added 15 ml MeOH, 145 mg (0.718 mmol, 1.15 eq.) of the aldehyde starting material, 65 mg NaH₃BCN, and 0.400 ml of AcOH. The reaction was stirred at room temperature and monitored by TLC (93:7:1 CH₂Cl₂/MeOH/aq. NH₃, product is higher R_f than starting material). After 24 hours, the reaction was not quite complete as judged by TLC, and 40 mg more NaH₃BCN was added. After stirring an additional 10 hours, no starting material remained as judged by TLC. The solvent was removed under vacuum and the residue was taken up in 95:5:1 CH₂Cl₂/MeOH/aq. NH₃ and chromatographed on silica gel using the same solvent mixture. This afforded 3 17 mg (65%) of the desired adduct, as well as a small amount of the bis-reductive amination adduct (faster eluting.)

Selected spectral data for 8a-(4-t-butyldimethylsilyloxybutyl)-8a-aza-9,10,11,12,13,14,15-heptanor-8a-homoerythromycin A:

$^1$H NMR (400 MHz, CDCl₃) δ 4.59 (d, H-1″), 4.32 (d, H-1′), 4.07 (dd, H-3), 3.98 (m, H-5″), 3.63 (s, COOCH₃), 3.57 (t, H-12), 3.49 (H-5), 3.26 (dd, H-2′), 3.24 (s, OCH₃), 2.95 (br d, H-4″), 2.79 (dq, H-2), 2.50 (m, H-3′), 2.26 (s, N(CH₃)₂), 1.28 & 1.17 (singlets, 6-Me and 3″-Me), 1.21, 1.20, 1.10 & 1.04 (methyl doublets), 0.84 & −0.01 (singlets, TBDMS).

FAB MS: 780 (M+H⁺)

Preparation of 8a-(4-t-butyldimethylsilyloxybutyl)-8a-benzenesulfonyl-8a-aza-9,10,11,12,13,14,15-heptanor-8a-homoerythromycin A To a 100 ml round bottom flask was introduced 317 mg (0.406 mmol) of 8a-(4-t-butyldimethylsilyloxybutyl)-8a-aza-9,10,11,12,13,14,15-heptanor-8a-homoerythromycin A, to which was added 25 ml $CH_2Cl_2$, ml triethylamine & 0.317 ml of benzenesulfonyl chloride (2.49 mmol, 6.1 eq.). The reaction was stirred at room temperature and monitored by TLC (93:7:1 $CH_2Cl_2$/MeOH/aq. $NH_3$, product is higher $R_f$ than starting material). After 14 hours, the reaction was judged to be complete by TLC. The solvent was removed under vacuum and the residue was taken up in 95:5:1 $CH_2Cl_2$/MeOH/aq. $NH_3$ and chromatographed on silica gel using the same solvent mixture. This afforded 284 mg (76%) of the desired product.

Selected spectral data for 8a-(4-t-butyldimethylsilyloxybutyl)-8a-benzenesulfonyl-8a-aza-9,10,11,12,13,14,15-heptanor-8a-homoerythromycin A:

$^1$H NMR (400 MHz, $CDCl_3$) δ 7.85 (d, $C_6H_5SO_2$—), 7.45 (m, $C_6H_5SO_2$—), 4.59 (d, H-1″), 4.33 (d, H-1′), 4.30 (m, H-9), 4.08 (dd, H-3), 3.98 (m, H-5″), 3.66 (s, $COOCH_3$), 3.56 (t, H-12), 3.36 (H-5), 3.30 (dd, H-2′), 3.24 (s, $OCH_3$), 2.95 (br t, H-4″), 2.59 (dq, H-2), 2.53 (m, H-3′), 2.28 (s, $N(CH_3)_2$), 2.26 (d, H-2″), 1.20 & 1.16 (singlets, 6-Me and 3″-Me), 1.26, 1.19, 1.11, 1.04 & 1.03 (methyl doublets), 0.85 & 0.00 (singlets, TBDMS).

FAB MS: 925 (M+Li$^+$)

Preparation of 8a-(4-hydroxybutyl)-8a-benzenesulfonyl-8a-aza-9,10,11,12,13,14,15-heptanor-8a-homoerythromycin A To a 100 ml round bottom flask was introduced 284 mg (0.309 mmol) of 8a-(4-t-butyldimethylsilyloxybutyl)-8a-benzenesulfonyl-8a-aza-9,10,11,12,13,14,15-heptanor-8a-homoerythromycin A, to which was added 10 ml THF dried over 3 A molecular sieves, and 0.570 ml 1M tetrabutylammonium fluoride in THF (0.570 mmol, 1.84 eq.). The reaction was stirred at room temperature and monitored by TLC (93:7:1 $CH_2Cl_2$/MeOH/aq. $NH_3$, product is lower $R_f$ than starting material). After 5 hours, the reaction was judged to be complete by TLC. The reaction mixture was diluted with 25 ml methylene chloride and extracted with water and then brine. The organic layer was dried over magnesium sulfate and the solvent was removed under vacuum. The residue was taken up in 95:5:1 $CH_2Cl_2$/MeOH/aq. $NH_3$ and chromatographed on silica gel using the same solvent mixture. NMR revealed that the chromatographed material was contaminated with tetrabutylammonium salts. The material was dissolved in 50 ml methylene chloride and extracted twice with 0.5N NaOH, followed by drying with magnesium sulfate and removal of solvent under vacuum. This afforded 223 mg (90%) of the desired product.

Selected spectral data for 8a-(4-hydroxybutyl)-8a-benzenesulfonyl-8a-aza-9,10,11,12,13,14,15-heptanor-8a-homoerythromycin A:

$^1$H NMR (400 MHz, $CDCl_3$) δ 7.86 (d, $C_6H_5SO_2$—), 7.45 (m, $C_6H_5SO_2$—), 4.60 (d, H-1″), 4.34 (d, H-1′), 4.26 (m, H-9), 4.05 (dd, H-3), 3.98 (m, H-5″), 3.64 (s, $COOCH_3$), 3.60 (m, H-12), 3.37 (H-5), 3.24 (s, $OCH_3$), 2.95 (br t, H-4″), 2.65 (dq, H-2), 2.50 (m, H-3′), 2.27 (s, $N(CH_3)_2$), 2.26 (d, H-2″), 1.19 & 1.17 (singlets, 6-Me and 3″-Me), 1.24, 1.18, 1.10, 1.07 & 1.03 (methyl doublets).

FAB MS: 812 (M+Li$^+$), 806 (M+H$^+$)

Preparation of 8a-benzenesulfonyl-8a-aza-9-deoxo-10-demethyl-11-dehydroxy-12-demethyl-12-dehydroxy-13,14,15-trisnor-8a-homoerythromycin A To a 100 ml round bottom flask was introduced 223 mg (0.275 mmol) of 8a-(4-hydroxybutyl)-8a-benzenesulfonyl-8a-aza-9,10,11,12,13,14,15-heptanor-8a-homoerythromycin A, to which was added 11 ml THF, 5.5 ml MeOH and 2 ml 1N NaOH (2 mmol, 7.3 eq.). The reaction was stirred at room temperature and monitored by TLC (93:7:1 $CH_2Cl_2$/MeOH/aq. $NH_3$, product is baseline). After 36 hours, the reaction was judged to be complete by TLC. The reaction mixture was diluted with 25 ml water and brought to pH=7 with aq. HCl. The solvent was removed under vacuum and the residue was dried for 12 hours under high vacuum. To the residue was added 200 ml of dry THF and the flask was sonicated for 5 minutes to insure proper mixing. To this cloudy mixture was added 200 mg (0.764 mmol, 2.8 eq.) of triphenylphosphine ($Ph_3P$) followed by 0.140 ml (144 mg, 0.711 mmol, 2.6 eq.) diisopropyl azodicarboxylate (DIAD). The reaction was stirred at room temperature and monitored by TLC (93:7:1 $CH_2Cl_2$/MeOH/aq. $NH_3$, product is mid $R_f$.) After 1 hour the reaction was judged to be only about 25% complete by TLC. Another 220 mg (0.840 mmol, 3.1 eq.) of triphenylphosphine and 0.150 ml of diisopropyl azodicarboxylate (154 mg, 0.762 mmol, 2.8 eq.) was added. After 1 hour the reaction was judged to be complete by TLC (no material remained at the baseline). The solvent was removed under vacuum and the residue was taken up in 94:6:1 $CH_2Cl_2$/MeOH/aq. $NH_3$ and chromatographed on silica gel using the same solvent mixture. This afforded 125 mg (58%) of the desired product.

Selected spectral data for 8a-benzenesulfonyl-8a-aza-9-deoxo-10-demethyl-11-dehydroxy-12-demethyl-12-dehydroxy-13,14,15-trisnor-8a-homoerythromycin A:

$^1$H NMR (400 MHz, $CDCl_3$) δ 7.85 (d, $C_6H_5SO_2$—), 7.45 (m, $C_6H_5SO_2$—), 4.62 (d, H-1″), 4.42, 4.34 & 3.94 (multiplets, H-9 and H12), 4.46 (d, H-1′), 4.25 (m, H-3), 3.93 (m, H-5″), 3.51 (m, H-5′), 3.44 (m, H-5), 3.29 (s, $OCH_3$), 3.24 (dd, H-2′), 2.63 (dq, H-2), 2.44 (m, H-3′), 2.31 (d, H-2″), 2.26 (s, $N(CH_3)_2$), 1.64 (br d, H-4′), 1.21 & 1.19 (singlets, 6-Me and 3″-Me), 1.23, 1.20, 1.13, 1.06 & 0.95 (methyl doublets).

$^{13}$C NMR (100 MHz, $CDCl_3$) δ 175.6, 141.2, 132.1, 128.9, 127.1, 102.6, 95.6, 85.2, 78.2, 77.8, 73.8, 72.9, 70.6, 69.5, 65.7, 65.4, 62.8, 50.4, 49.3, 44.2, 44.1, 42.4, 42.0, 40.4, 34.8, 28.7, 26.8, 25.4, 22.5, 21.6, 21.2, 20.0, 17.8, 12.8, 9.4.

FAB MS: 775 (M+H$^+$)

Preparation of 8a-aza-9-deoxo-10-demethyl-11-dehydroxy-12-demethyl-12-dehydroxy-13,14,15-trisnor-8a-homoerythromycin A:

To a 50 ml round bottom flask was introduced 120 mg (0.155 mmol) of 8a-benzenesulfonyl-8a-aza-9-deoxo-10-demethyl-11-dehydroxy-12-demethyl-12-dehydroxy-13,14,15-trisnor-8a-homoerythromycin A and 5 ml sieve dried THF and the mixture was cooled in an acetone/dry ice bath. Lithium naphthalide solution (prepared by adding 69 mg (10 mmol, 2 eq.) of finely chopped lithium to 5 ml of a 1M solution of naphthalene in THF, sonicating until it turned green, and then stirring for 30 minutes at room temperature) was added dropwise until the green color persisted, and the the reaction was allowed to stir for 10 minutes, with an additional drop of naphthalide solution added periodically as the green color faded. The reaction was then quenched with 0.5 ml of saturated aqueous $NaHCO_3$ and allowed to warm to room temperature. The reaction was added to 150 ml of $CH_2Cl_2$ and extracted with 0.1N NaOH. The organic layer was dried over $MgSO_4$ and concentrated under vacuum. The residue was taken up in 94:6:1 $CH_2Cl_2$/MeOH/aq. $NH_3$ and chromatographed on silica gel using the same solvent mixture. This afforded 80 mg (80%) of the desired product.

Selected spectral data for 8a-aza-9-deoxo-10-demethyl-11-dehydroxy-12-demethyl-12-dehydroxy-13,14,15-trisnor-8a-homoerythromycin A:

$^1$H NMR (400 MHz, $CDCl_3$) δ 4.66 (d, H-1″), 4.45 (d, H-3), 4.41 (d, H-1′), 4.14 (m, H-12), 3.99 (m, H-5″), 3.93 (d, H-12), 3.64 (d, H-5), 3.47 (m, H-5′), 3.29 (s, $OCH_3$), 3.18 (dd, H-2′), 2.99 (d, H-4″), 2.64 (dq, H-2), 2.42 (m, H-3′), 2.32 (d, H-2″), 2.24 (s, N($CH_3$)$_2$), 2.00 (m, H-4), 1.29 & 1.20 (singlets, 6-Me and 3″-Me), 1.28, 1.19, 1.14, 1.12 & 1.09 (methyl doublets).

$^{13}$C NMR (100 MHz, $CDCl_3$) δ 176.0, 102.9, 96.1, 82.5, 78.8, 78.0, 75.3, 72.8, 70.8, 69.1, 65.6, 65.4, 65.0, 49.4, 49.3, 44.8, 42.4, 41.8, 40.3, 40.2, 35.1, 28.7, 27.1, 26.9, 24.7, 21.6, 21.3, 21.1, 18.1, 13.3, 9.6.

FAB MS: 634 (M+H$^+$)

Preparation of 8a-methyl-8a-aza-9-deoxo-10-demethyl-11-dehydroxy-12-demethyl-12-dehydroxy-13,14,15-trisnor-8a-homoerythromycin A:

To a 50 ml round bottom flask was introduced 43 mg (0.068 mmol) of 8a-aza-9-deoxo-10-demethyl-11-dehydroxy-12-demethyl-12-dehydroxy-13,14,15-trisnor-8a-homoerythromycin A, to which was added 5 ml MeOH, 0.050 ml 37% aq. formaldehyde (ca. 0.6 mmol, 9 eq.), and 15 mg sodium cyanoborohydride (0.238 mmol, 3.5 eq.). The reaction was stirred at room temperature and monitored by TLC (93:7:1 $CH_2Cl_2$/MeOH/aq. $NH_3$). After 1 hour, TLC showed no starting material and two higher R$_f$ spots. The reaction was added to 50 ml of $CH_2Cl_2$ and extracted with 0.1N NaOH. The organic layer was dried over $MgSO_4$ and concentrated under vacuum. The residue was taken up in 94:6:1 $CH_2Cl_2$/MeOH/aq. $NH_3$ and chromatographed on silica gel using the same solvent mixture. This afforded 16 mg (37%) of the higher Rf spot, which proved to be the desired product and 22 mg (51%) of the lower spot, which proved to be acyclic methyl ester resulting from opening of the lactone with methanol.

Selected spectral data for 8a-methyl-8a-aza-9-deoxo-10-demethyl-11-dehydroxy-12-demethyl-12-dehydroxy-13,14,15-trisnor-8a-homoerythromycin A:

$^1$H NMR (400 MHz, $CDCl_3$) δ 4.85 (d, H-1″), 4.70 (d, H-3), 4.32 (d, H-1′), 4.11 (m, H-12), 4.01 (m, H-5″), 3.95 (d, H-12), 3.63 (d, H-5), 3.42 (m, H-5′), 3.27 (s, $OCH_3$), 3.17 (dd, H-2′), 2.98 (br t, H-4″), 2.75 (dq, H-2), 2.45 (m, H-3′), 2.32 (d, H-2″), 2.27 (s, ring N-$CH_3$), 2.24 (s, N($CH_3$)$_2$), 2.09 (m, H-4), 1.42 & 1.20 (singlets, 6-Me and 3″-Me), 1.32, 1.20, 1.17, 1.16 & 0.85 (methyl doublets).

FAB MS: 647 (M+H$^+$)

Elemental analysis: Calcd for $C_{33}H_{62}N_2O_{10} \cdot \frac{1}{2}H_2O$: C, 60.43; H, 9.68; N, 4.27. Found: C, 59.87, 60.07; H, 9.61, 9.85; N, 4.59, 4.36.

EXAMPLE 17

General Preparation of 14-Membered Azalides

Following the procedure given in Example 13, 8a-aza-8a-homo-9,10,11,12,13,14,15-heptanorerythromycin A and various trialkylsiloxyaldehydes (which may be prepared as taught in examples 4, 6 and 12) are used as starting materials for 14-membered azalides, as diagrammed below:

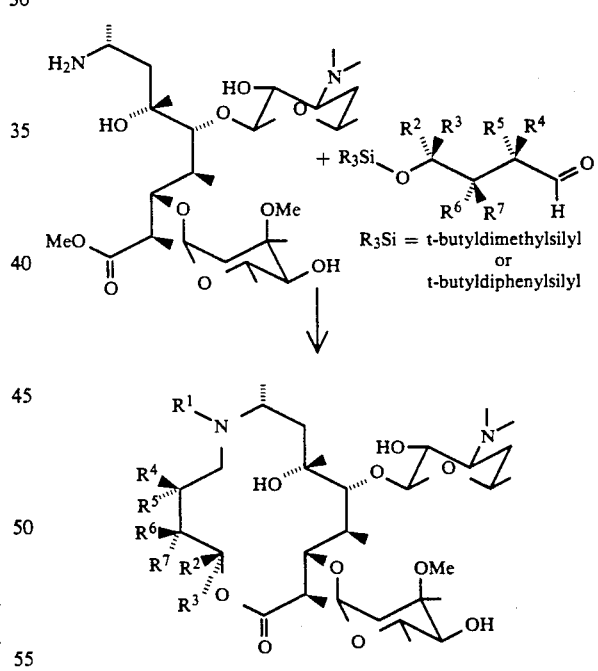

where R$^1$ is benzenesulfonyl, hydrogen or methyl; one of R$^2$ and R$^3$ is hydrogen and the other is hydrogen or C$_1$ to C$_7$ alkyl, cycloalkyl or aryl, which may be substituted with R$^{10}$, C$_6$H$_5$SO$_2$HN or F; R$^4$, R$^5$, R$^6$ and R$^7$ are hydrogen, C$_1$ to C$_7$ alkyl, fluoroalkyl, cycloalkyl or aryl, R$^{10}$, C$_6$H$_5$SO$_2$HN or F; R$^{10}$ is benzyl, C$_1$ to C$_7$ alkyl, fluoroalkyl, cycloalkyl or aryl.

Examples of the compounds that can be produced in this manner include those in the following table:

TABLE 8-1

| aldehyde (R' = Me, Bn) | macrocycle (R = PhSO$_2$—, H or Me) |
|---|---|
| [structure: TBS-O-CH$_2$-CH(OR')-CH(C$_6$H$_{13}$)-CHO] | [macrocycle structure with C$_6$H$_{13}$ substituent] |
| [structure: TBS-O-CH$_2$-C$_6$H$_4$-CHO (ortho)] | [macrocycle structure with benzyl linker] |
| [structure: TBS-O-CH(Me)-CH(OR')-CH(OR')-CHO] | [macrocycle structure with two R'O groups] |
| [structure: TBS-O-CH$_2$-CH(OR')-CH(Me)-CHO] | [macrocycle structure] |

Following the procedure given in example 13, 8a-aza-8a-homo-9,10,11,12,13,14,15-heptanorerythromycin A and various trialkylsiloxyaldehydes (which may be prepared as taught in examples 4, 6 and 12) are used as starting materials for 14-membered azalides, as diagrammed below:

TABLE 8-3

| aldehyde (R' = Me, Bn) | macrocycle (R = PhSO$_2$—, H or Me) |
|---|---|
| [structure: TBS-O-CH$_2$-CHF-CH$_2$-CHO] | [macrocycle structure with F substituent] |

TABLE 8-3-continued
| aldehyde (R' = Me, Bn) | macrocycle (R = PhSO$_2$—, H or Me) |
|---|---|
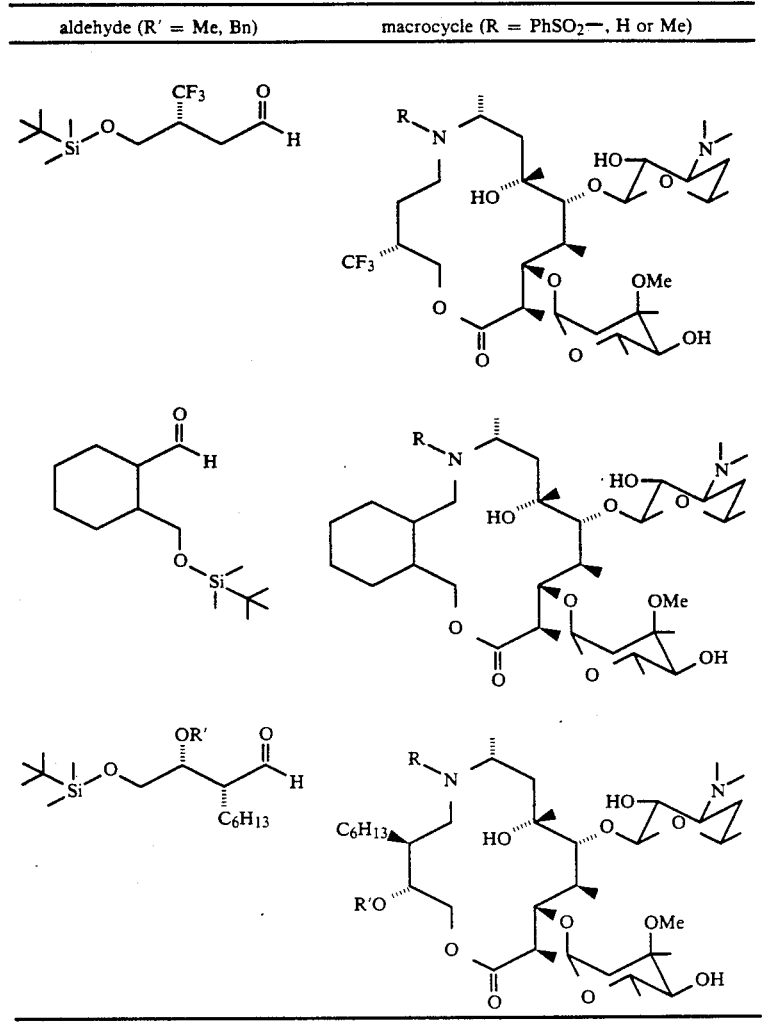
EXAMPLE 18
Preparation of 8a-methyl-8a-aza-9-deoxo-10-demethyl-11-deoxy-12-demethyl-12-deoxy-14,15-bisnor-8a-homoerythromycin A
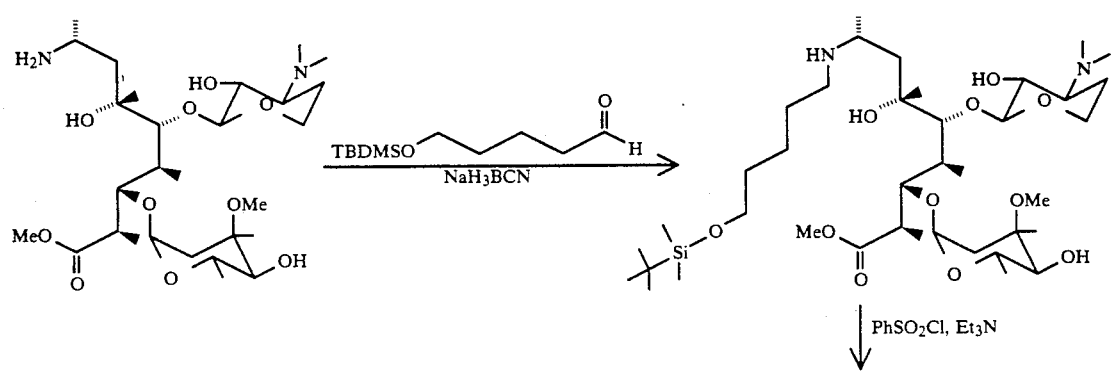

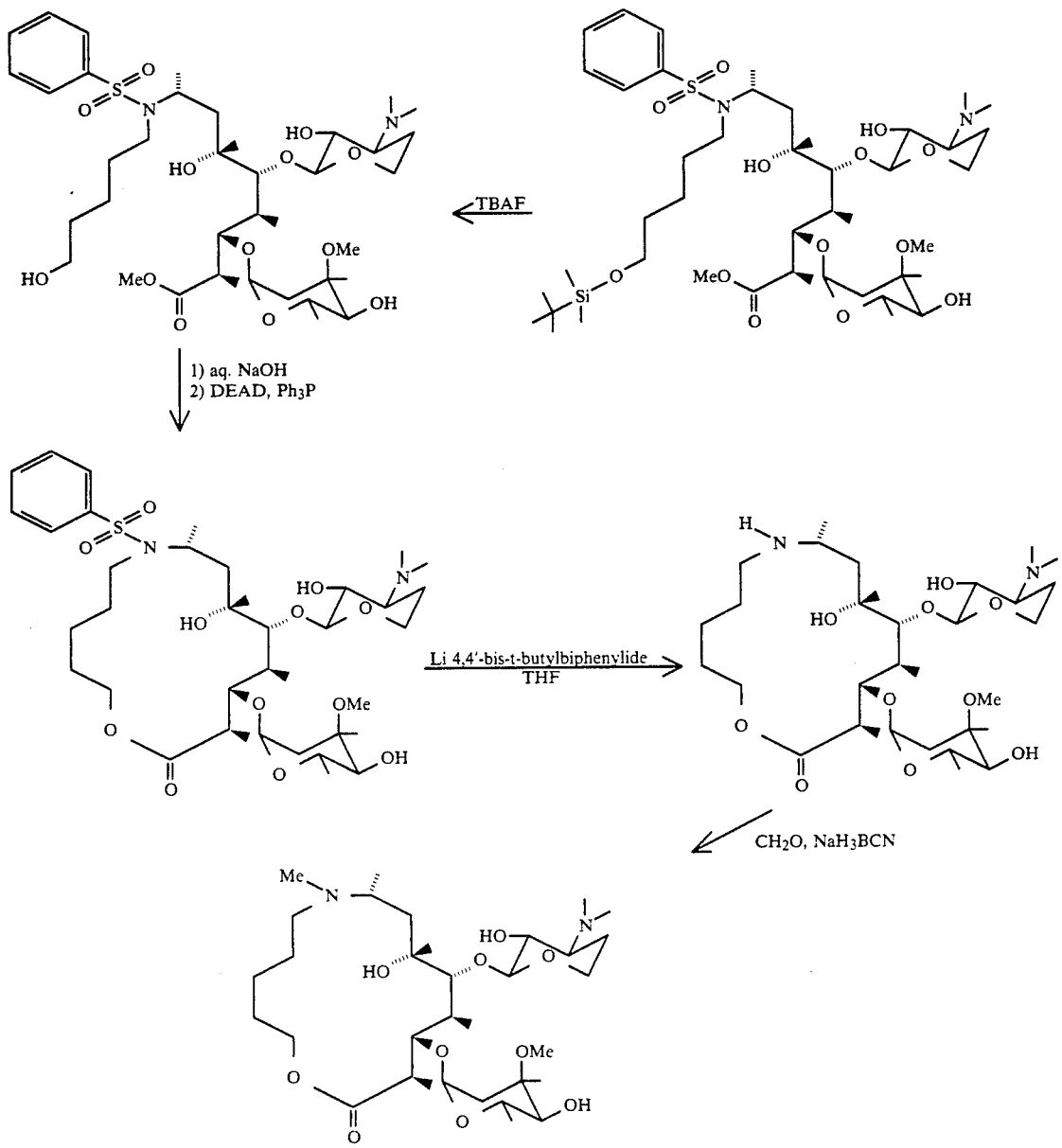

Preparation of
8a-(5-t-butyldimethylsilyloxypentyl)-8a-aza-9,10,11,12,13,14,15-heptanor-8a-homoerythromycin A To a 100 ml round bottom flask was introduced 332 mg (0.625 mmol) of 8a-aza-9,10,11,12,13,14,15-heptanor-8a-homoerythromycin A, to which was added 15 ml MeOH, 150 mg (0.694 mmol, 1.11 eq.) of the aldehyde starting material, 65 mg NaH$_3$BCN (0.97 mmol, 1.55 eq.), and 0.400 ml of AcOH. The reaction was stirred at room temperature and monitored by TLC (93:7:1 CH$_2$Cl$_2$/MeOH/aq. NH$_3$, product is higher R$_f$ than starting material). After 24 hours, the reaction was not complete as judged by TLC, and 130 mg (0.601 mmol, 0.96 eq.) of the aldehyde and 65 mg more NaH$_3$BCN (0.97 mmol, 1.55 eq.) was added. After stirring an additional 10 hours, only a small amount of starting material remained as judged by TLC. The solvent was removed under vacuum and the residue was taken up in 95:5:1 CH$_2$Cl$_2$/MeOH/aq. NH$_3$ and chromatographed on silica gel using the same solvent mixture. This afforded 271 mg (72% corrected for recovered starting material) of the desired adduct, and 40 mg recovered starting material.

Selected spectral data for 8a-(5-t-butyldimethylsilyloxypentyl)-8a-aza-9,10,11,12,13,14,15-heptanor-8a-homoerythromycin A:

$^1$H NMR (400 MHz, CDCl$_3$) δ 4.62 (d, H-1″), 4.37 (d, H-1′), 4.10 (dd, H-3), 4.00 (m, H-5″), 3.63 (s, COOCH$_3$), 3.57 (t, H-13), 3.51 (H-5), 3.26 (s, OCH$_3$), 2.97 (br d, H-4″), 2.82 (dq, H-2), 2.50 (m, H-3′), 2.26 (s, N(CH$_3$)$_2$), 1.29 & 1.19 (singlets, 6-Me and 3″-Me), 1.22, 1.21, 1.11 & 1.08 (methyl doublets), 0.85 & 0.02 (singlets, TBDMS).

FAB MS: 794 (M+H$^+$)

Preparation of 8a-benzenesulfonyl-8a-(5-t-butyldimethylsilyloxypentyl)-8a-aza-9,10,11,12,13,14,15-heptanor-8a-homoerythromycin A:

To a 100 ml round bottom flask was introduced 271 mg (0.342 mmol) of 8a-(5-t-butyldimethylsilyloxypentyl)-8a-aza-9,10,11,12,13,14,15-heptanor-8a-homoerythromycin A, to which was added 5 ml $CH_2Cl_2$, 0.8 ml triethylamine & 0.271 ml of benzenesulfonyl chloride (2.13 mmol, 6.2 eq.). The reaction was stirred at room temperature and monitored by TLC (93:7:1 $CH_2Cl_2$/MeOH/aq. $NH_3$, product is higher $R_f$ than starting material). After 36 hours, the reaction was judged to be complete by TLC. The solvent was removed under vacuum and the residue was taken up in 94:6:1 $CH_2Cl_2$/MeOH/aq. $NH_3$ and chromatographed on silica gel using the same solvent mixture. This afforded 342 mg of the desired product contaminated with triethylamine, but deemed sufficiently pure for use in the next reaction.

Selected spectral data for 8a-benzenesulfonyl-8a-(5-t-butyldimethylsilyloxypentyl)-8a-aza-9,10,11,12,13,14,15-heptanor-8a-homoerythromycin A:

$^1$H NMR (400 MHz, $CDCl_3$) δ 7.86 (d, $C_6H_5SO_2$—), 7.45 (m, $C_6H_5SO_2$—), 4.60 (d, H-1″), 4.34 (d, H-1′), 4.29 (m, H-9), 4.08 (dd, H-3), 3.98 (m, H-5″), 3.67 (s, $COOCH_3$), 3.55 (t, H-13), 3.30 (dd, H-2′), 3.25 (s, $OCH_3$), 2.95 (br t, H-4″), 2.61 (dq, H-2), 2.52 (m, H-3′), 2.28 (s, $N(CH_3)_2$), 2.26 (d, H-2″), 1.20 & 1.16 (singlets, 6-Me and 3″-Me), 1.26, 1.19, 1.11, 1.04 & 1.03 (methyl doublets), 0.85 & 0.00 (singlets, TBDMS).

$^{13}$C NMR (100 MHz, $CDCl_{13}$) δ 176.0, 141.2, 132.0, 128.7, 127.3, 126.3, 105.0, 96.2, 86.7, 79.9, 77.8, 73.4, 72.7, 70.5, 69.8, 65.5, 65.1, 63.0, 51.8, 50.8, 49.4, 44.6, 44.5, 41.5, 40.3, 37.6, 35.2, 32.4, 31.3, 28.9, 26.0, 24.2, 23.5, 21.6, 21.5, 21.2, 17.8, 10.7, 10.0, −5.3.

FAB MS: 934 (M+H$^+$)

Preparation of 8a-benzenesulfonyl-8a-(5-hydroxypentyl)-8a-aza-9,10,11,12,13,14,15-heptanor-8a-homoerythromycin A To a 100 ml round bottom flask was introduced 342 mg (0.367 mmol) of 8a-benzenesulfonyl-8a-(5-t-butyldimethylsilyloxypentyl)-8a-aza-9,10,11,12,13,14,15-heptanor-8a-homoerythromycin A, to which was added 10 ml THF dried over 3 A molecular sieves, and 0.540 ml 1M tetrabutylammonium fluoride in THF (0.540 mmol, 1.47 eq.). The reaction was stirred at room temperature and monitored by TLC (93:7:1 $CH_2Cl_2$/MeOH/aq. $NH_3$, product is lower $R_f$ than starting material). After 24 hours, the reaction was judged to be complete by TLC. After the solvent was removed under vacuum, the residue was taken up in 94:6:1 $CH_2Cl_2$/MeOH/aq. $NH_3$ and chromatographed on silica gel using the same solvent mixture. NMR revealed that the chromatographed material was contaminated with tetrabutylammonium salts. This afforded 210 mg (70% yield) of the desired product.

Selected spectral data for 8a-benzenesulfonyl-8a-(5-hydroxypentyl)-8a-aza-9,10,11,12,13,14,15-heptanor-8a-homoerythromycin A:

$^1$H NMR (400 MHz, $CDCl_3$) δ 7.85 (d, $C_6H_5SO_2$—), 7.45 (m, $C_6H_5SO_2$—), 4.59 (d, H-1″), 4.33 (d, H-1′), 4.26 (m, H-9), 4.05 (m, H-3), 3.98 (m, H-5″), 3.65 (s, $COOCH_3$), 3.58 (t, H-13), 3.37 (H-5), 3.24 (s, $OCH_3$), 2.62 (dq, H-2), 2.51 (m, H-3′), 2.27 (s, $N(CH_3)_2$), 2.23 (d, H-2″).

FAB MS: 820 (M+H$^+$)

Preparation of 8a-benzenesulfonyl-8a-aza-9-deoxo-10-demethyl-11-deoxy-12-demethyl-12-deoxy-14,15-bisnor-8a-homoerythromycin A To a 100 ml round bottom flask was introduced 210 mg (0.257 mmol) of 8a-benzenesulfonyl-8a-(5-hydroxypentyl)-8a-aza-9,10,11,12,13,14,15-heptanor-8a-homoerythromycin A, to which was added 5 ml THF, 5 ml MeOH and 2 ml 1N NaOH (2 mmol, 7.8 eq.). The reaction was stirred at room temperature and monitored by TLC (93:7:1 $CH_2Cl_2$/MeOH/aq. $NH_3$, product is baseline). After 36 hours, the reaction was judged to be complete by TLC. The reaction mixture was diluted with 25 ml water and brought to pH=7 with aq. HCl. The solvent was removed under vacuum and the residue was dried for 12 hours under high vacuum. To the residue was added 200 ml of dry THF and the flask was sonicated for 5 minutes to insure proper mixing. To this cloudy mixture was added 400 mg (1.53 mmol, 6.0 eq.) of triphenylphosphine followed by 0.280 ml (288 mg, 1.42 mmol, 5.5 eq.) diethyl azodicarboxylate. The reaction was stirred at room temperature and monitored by TLC (93:7:1 $CH_2Cl_2$/MeOH/aq. $NH_3$, product is mid $R_f$.) After 1 hour the reaction was judged to be incomplete by TLC. Another 200 mg (0.764 mmol, 3.0 eq.) of triphenylphosphine and 0.140 ml of diisopropyl azodicarboxylate (DEAD) (144 mg, 0.711 mmol, 2.8 eq.) was added. After 1 hour the reaction was judged to be complete by TLC (no material remained at the baseline). The solvent was removed under vacuum and the residue was taken up in 94:6:1 $CH_2C_2$/MeOH/aq. $NH_3$ and chromatographed on silica gel using the same solvent mixture. This afforded 116 mg (57%) of the desired product.

Selected spectral data for 8a-benzenesulfonyl-8a-aza-9-deoxo-10-demethyl-11-deoxy-12-demethyl-12-deoxy-14,15-bisnor-8a-homoerythromycin A:

$^1$H NMR (400 MHz, $CDCl_3$) δ 7.82 (d, $C_6H_5SO_2$—), 7.45 (m, $C_6H_5SO_2$—), 4.72 (d, H-1″), 4.43, 4.1 & 4.0 (multiplets, H-9 and H13), 4.46 (d, H-1′), 4.08 (m, H-3), 4.0 (m, H-5″), 3.55 (m, H-5′), 3.49 (m, H-5), 3.27 (s, $OCH_3$), 3.0 (br d, H-4″), 2.63 (dq, H-2), 2.49 (m, H-3′), 2.32 (d, H-2″), 2.26 (s, $N(CH_3)_2$), 1.64 (br d, H-4′), 1.16, 1.01 & 0.97 (methyl doublets).

FAB MS: 788 (M+H$^+$)

Preparation of 8a-aza-9-deoxo-10-demethyl-11-deoxy-12-demethyl-12-deoxy-14,15-bisnor-8a-homoerythromycin A Lithium 4,4′-bis-t-butylbiphenylide solution was prepared by adding 35 mg (5 mmol, 5 eq.) of finely chopped lithium to a solution of 273 mg 4,4′-bis-t-butylbiphenyl (1.03 mmol) in 5 ml of dry THF. The solution was sonicated until it turned green and then stirred for 1 hour in an ice bath.

To a 50 ml round bottom flask was introduced 89 mg (0.113 mmol) of 8a-benzenesulfonyl-8a-aza-9-deoxo-10-demethyl-11-deoxy-12-demethyl-12-deoxy-14,15-bisnor-8a-homoerythromycin A and 5 ml sieve dried THF and the mixture was cooled in an acetone/dry ice bath. The lithium 4,4′-bis-t-butylbiphenylide solution prepared as described above was added dropwise until the green color persisted, and the the reaction was allowed to stir for 10 minutes, with an additional drop of biphenylide solution added periodically as the green color faded. The reaction was then quenched with 0.5 ml of saturated aqueous NaHCO₃ and allowed to warm to room temperature. The reaction was added to 150 ml of CH₂Cl₂ and extracted with 0.1N NaOH. The organic layer was dried over MgSO₄ and concentrated under vacuum. The residue was taken up in 94:6:1 CH₂Cl₂/MeOH/aq. NH₃ and chromatographed on silica gel using the same solvent mixture. This afforded 29 mg (40%) of the desired product.

Selected spectral data for 8a-aza-9-deoxo-10-demethyl-11-deoxy-12-demethyl-12-deoxy-14,15-bisnor-8a-homoerythromycin A:

¹H NMR (400 MHz, CDCl₃) δ 4.76 (d, H-1″), 4.40 (d, H-3), 4.38 (d, H-1′), 4.12 (m, H-12), 4.02 (m, H-5″), 3.93 (d, H-13), 3.56 (d, H-5), 3.49 (m, H-5′), 3.31 (s, OCH₃), 3.19 (dd, H-2′), 3.00 (d, H-4″), 2.70 (dq, H-2), 2.43 (m, H-3′), 2.35 (d, H-2″), 2.25 (s, N(CH₃)₂), 2.05 (m, H-4), 1.36 & 1.20 (singlets, 6-Me and 3″-Me), 1.29, 1.19, 1.10, 1.08 & 1.06 (methyl doublets).

FAB MS: 647 (M+H⁺)

Preparation of
8a-methyl-8a-aza-9-deoxo-10-demethyl-11-deoxy-12-demethyl-12-deoxy-14,15-bisnor-8a-homoerythromycin A To a 50 ml round bottom flask was introduced 18 mg (0.028 mmol) of 8a-aza-9-deoxo-10-demethyl-11-deoxy-12-demethyl-12-deoxy-14,15-bisnor-8a-homoerythromycin A, to which was added 5 ml MeOH, 0.050 ml 37% aq. formaldehyde (ca. 0.6 mmol, 9 eq.), and 15 mg sodium cyanoborohydride (0.238 mmol, 3.5 eq.). The reaction was stirred at room temperature and monitored by TLC (93:7:1 CH₂Cl₂/MeOH/aq. NH₃). After 1 hour, TLC showed complete converstion to a higher R_f spot. The reaction was added to 50 ml of CH₂Cl₂ and extracted with 0.1N NaOH. The organic layer was dried over MgSO₄ and concentrated under vacuum. The residue was taken up in 94:6:1 CH₂Cl₂/MeOH/aq. NH₃ and chromatographed on silica gel using the same solvent mixture. This afforded 16 mg (90%) of the desired product.

Selected spectral data for 8a-methyl-8a-aza-9-deoxo-10-demethyl-11-deoxy-12-demethyl-12-deoxy-14,15-bisnor-8a-homoerythromycin A:

¹H NMR (400 MHz, CDCl₃) δ 4.90 (d, H-1″), 4.41 (d, H-1′), 4.29 (d, H-3), 4.06 (m, H-13), 4.04 (m, H-5″), 3.59 (d, H-5), 3.49 (m, H-5′), 3.32 (s, OCH₃), 3.01 (br t, H-4″), 2.74 (dq, H-2), 2.41 (m, H-3′), 2.35 (d, H-2″), 2.25 (s, N(CH₃)₂), 2.21 (s, ring N-CH₃), 2.09 (m, H-4), 1.39 & 1.21 (singlets, 6-Me and 3″-Me), 1.30, 1.22, 1.13, 1.07 & 0.87 (methyl doublets).

Elemental analysis: Calcd for C₃₄H₆₄N₂O₁₀: C, 61.79; H, 9.76; N, 4.24. Found: C, 61.62, 61.70; H, 9.79, 9.84; N, 4.47, 4.33.

FAB MS: 662 (M+H⁺)

EXAMPLE 19

General Preparation of 15-Membered Azalides

Following the procedure given in example 13, 8a-aza-8a-homo-9,10,11,12,13,14,15-heptanorerythromycin A and various trialkylsiloxyaldehydes (which may be prepared as taught in examples 4 through 12) are used as starting materials for 15-membered azalides, as diagrammed below:

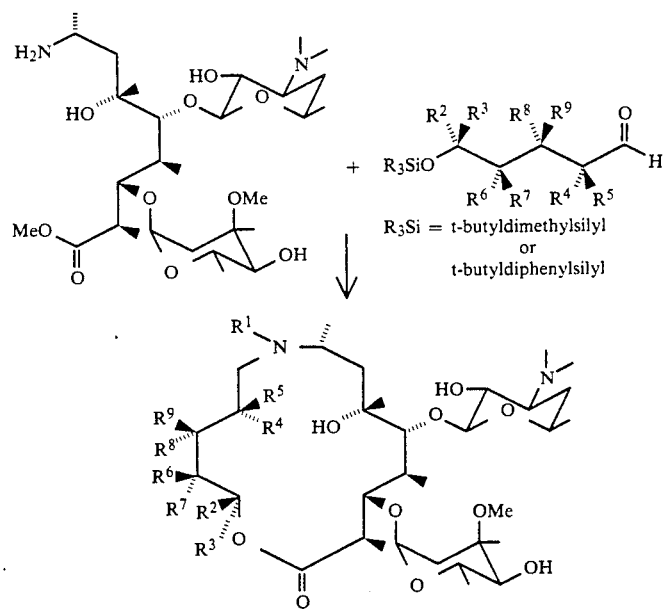

A representative but nonlimiting sampling of the compounds that can be produced in this manner include those in the following table:

TABLE 9-1
| aldehyde (R' = Me, Bn) | macrocycle (R = PhSO₂—, H or Me) |
|---|---|
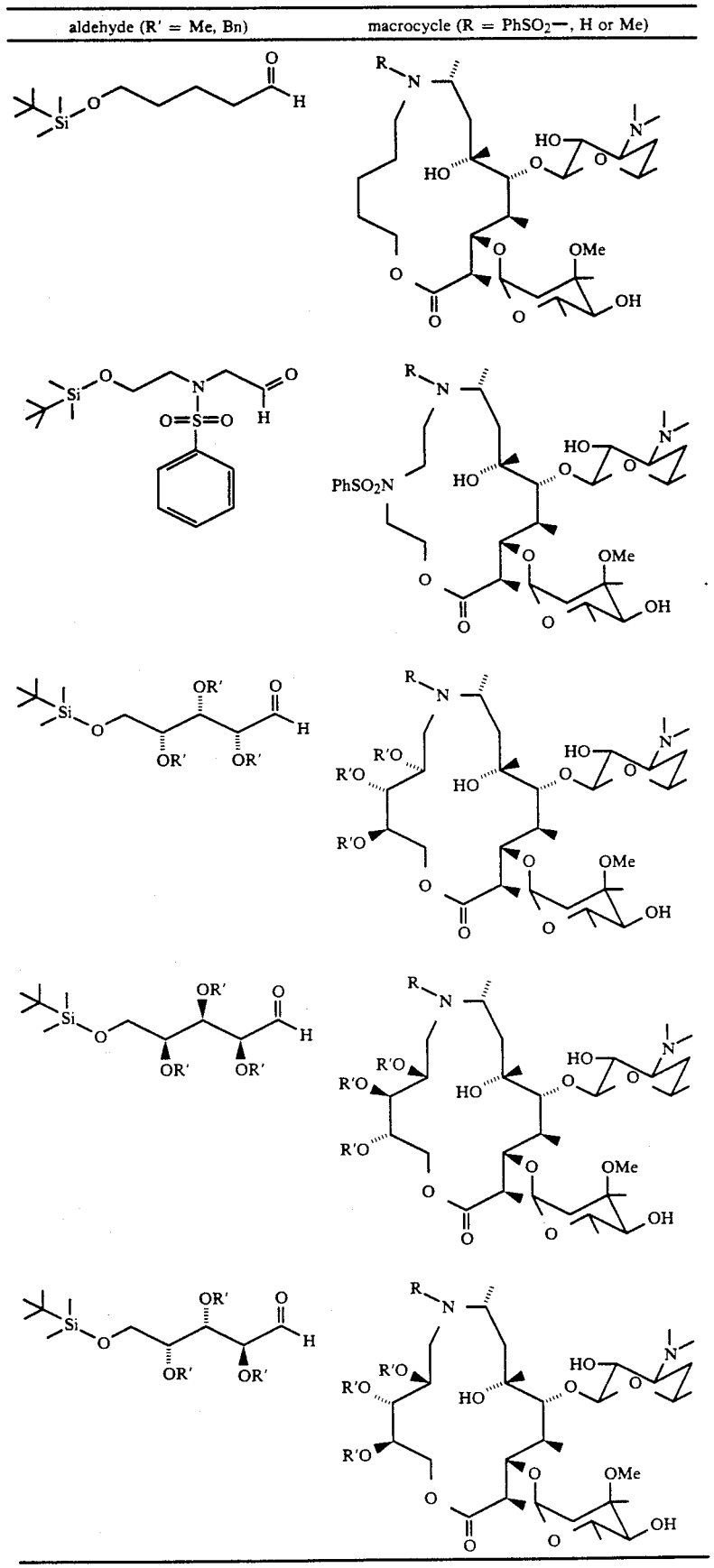

TABLE 9-2

| aldehyde (R' = Me, Bn) | macrocycle (R = PhSO$_2$—, H or Me) |
|---|---|

TABLE 9-3
| aldehyde (R' = Me, Bn) | macrocylce (R = PhSO$_2$—, H or Me) |
|---|---|
| 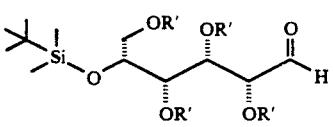 | 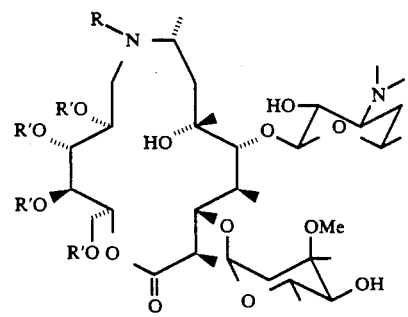 |
| 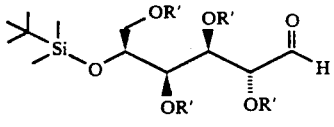 | 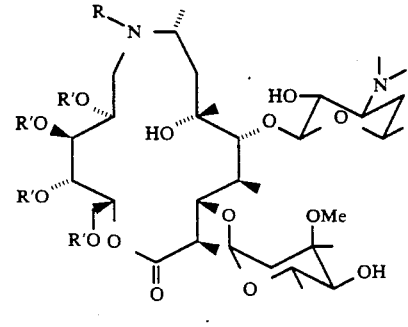 |
| 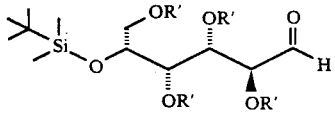 | 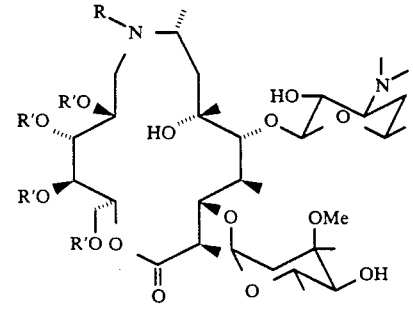 |
| 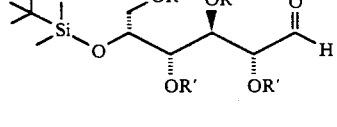 | 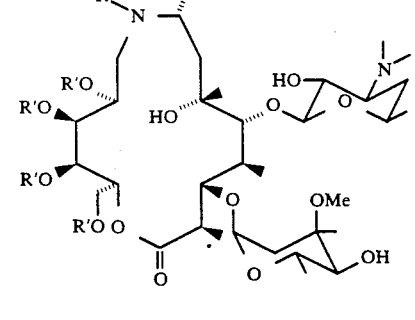 |
| 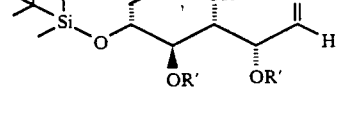 | 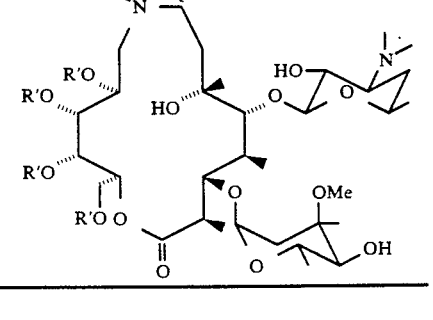 |

TABLE 9-4
| aldehyde (R' = Me, Bn) | macrocycle (R = PhSO₂—, H or Me) |
|---|---|
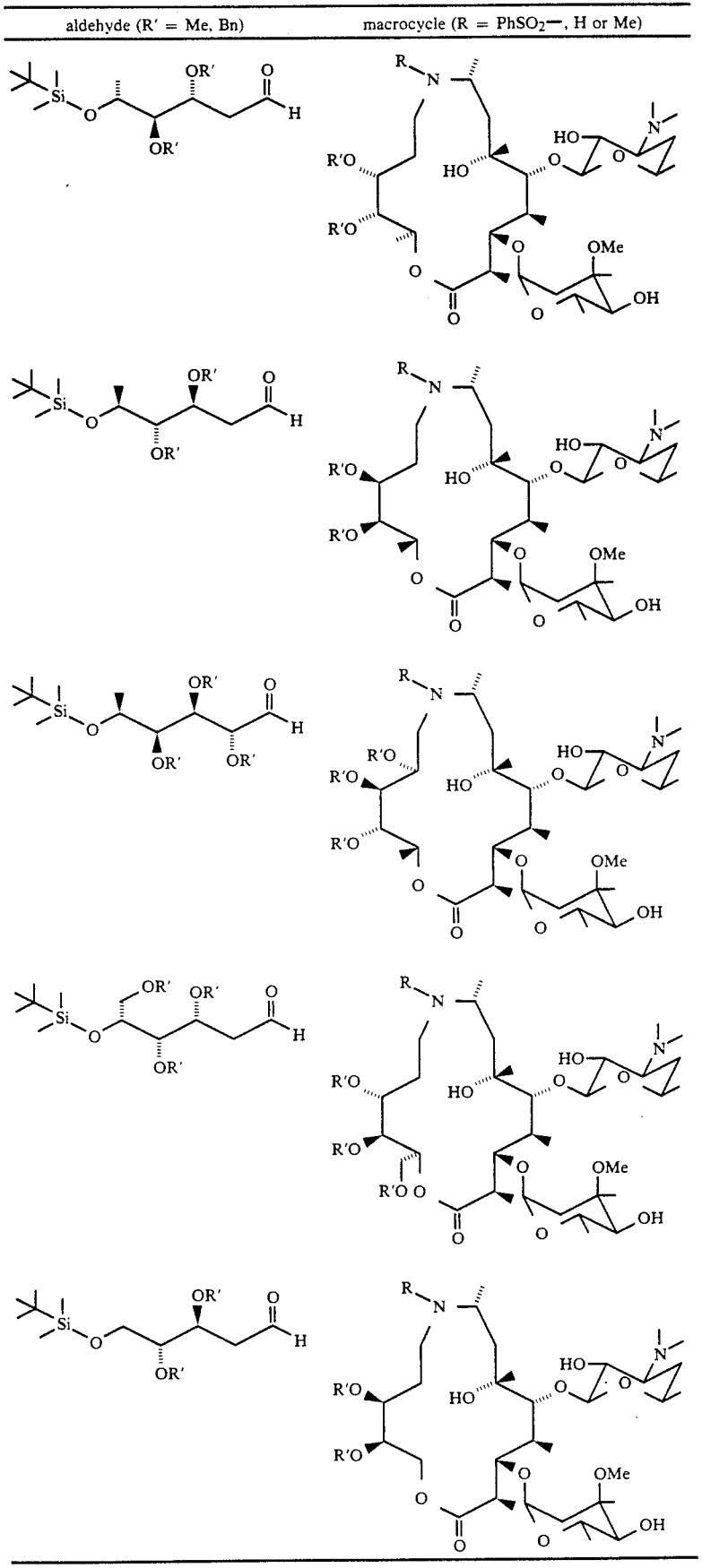

TABLE 9-5

| aldehyde (R' = Me, Bn) | macrocycle (R = PhSO₂—, H or Me) |
|---|---|

TABLE 9-6

| aldehyde | macrocycle (R = PhSO₂—, H or Me) |
|---|---|

TABLE 9-7

| aldehyde | macrocycle (R = PhSO₂—, H or Me) |
|---|---|

TABLE 9-8

| aldehyde | macrocycle (R = PhSO$_2$—, H or Me) |
|---|---|

TABLE 9-9

| aldehyde | macrocycle (R = PhSO$_2$—, H or Me) |
|---|---|

TABLE 9-10
| aldehyde | macrocycle (R = PhSO$_2$—, H or Me) |
|---|---|
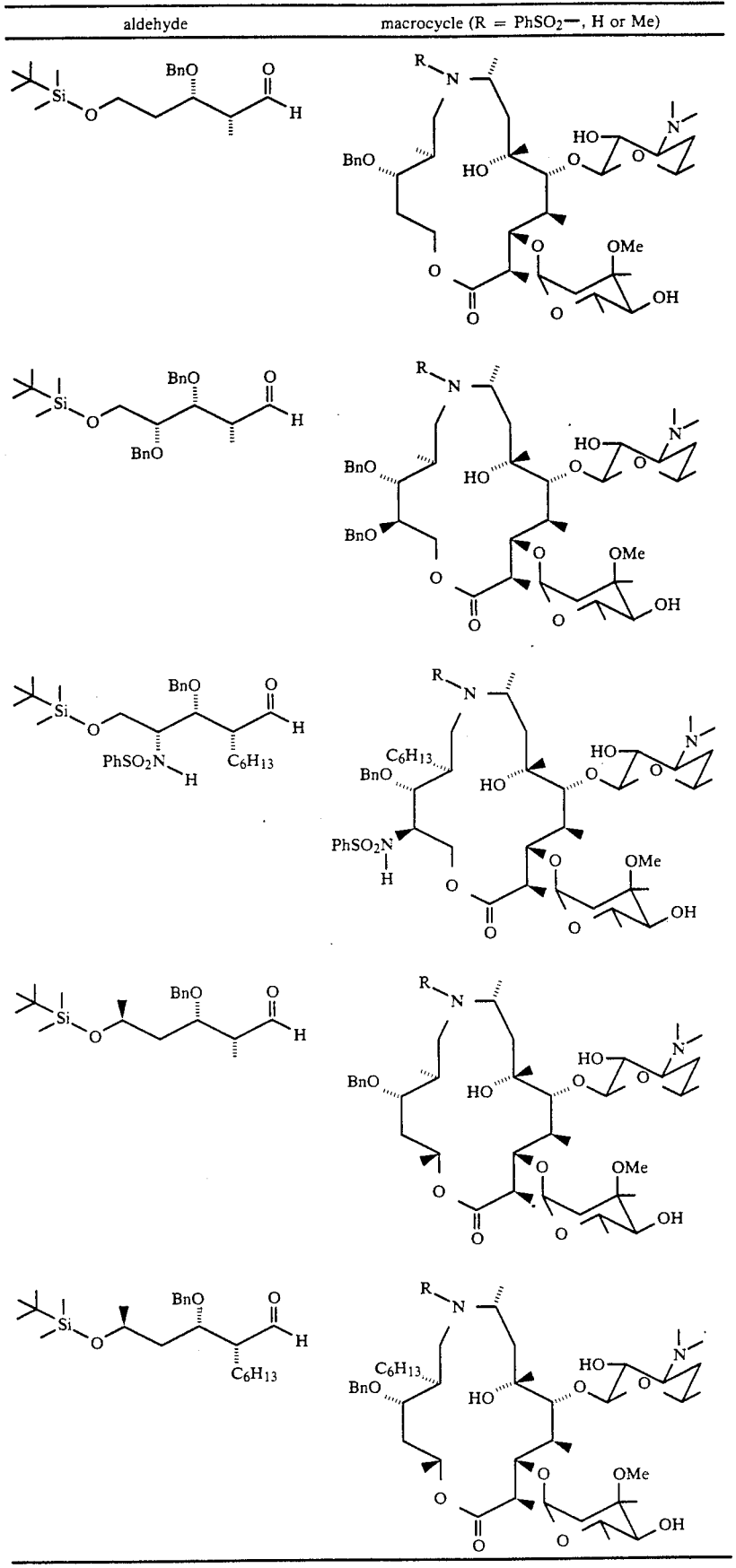

TABLE 9-11
| aldehyde | macrocycle (R = PhSO$_2$—, H or Me) |
|---|---|
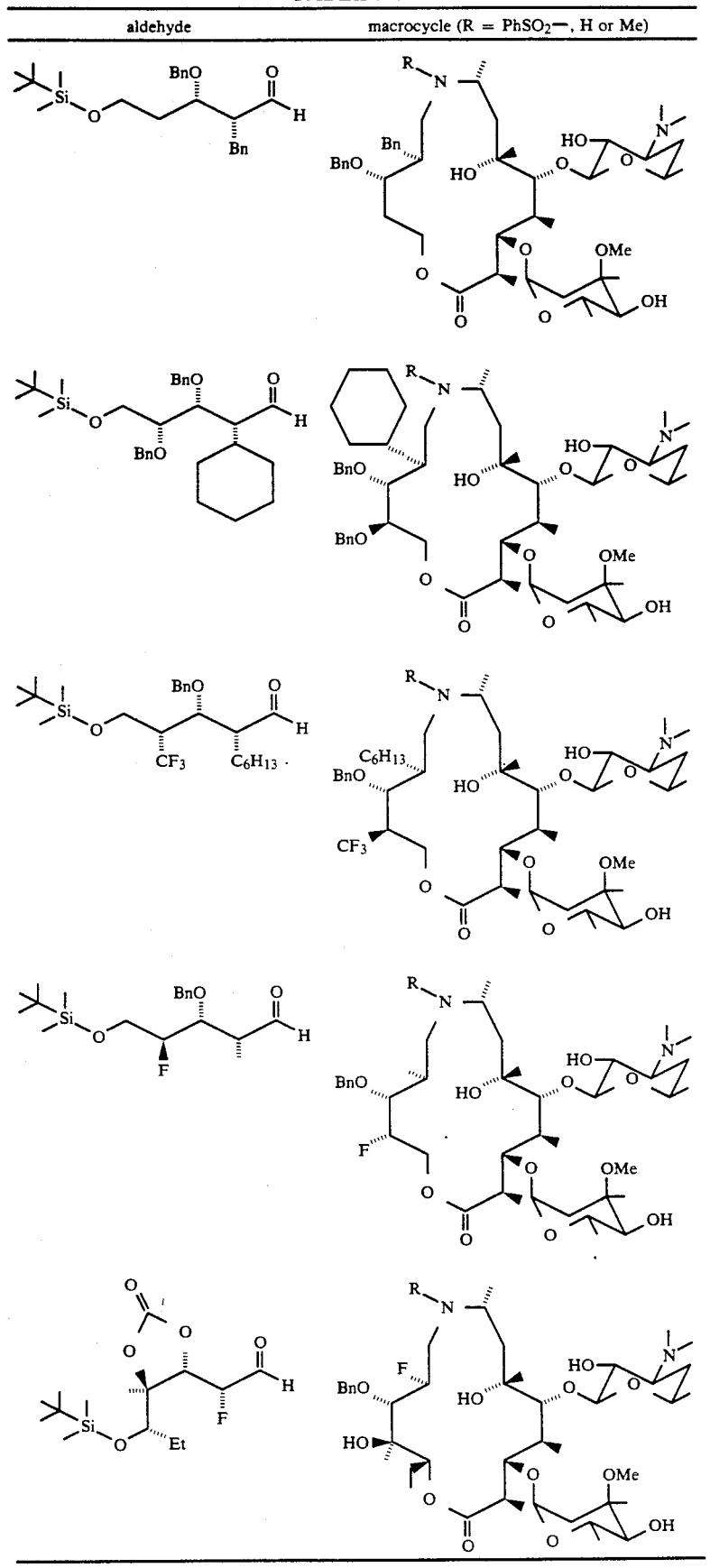

EXAMPLE 20

Preparation of
8a-methyl-8a-aza-9-deoxo-14,15-bisnor-8a-homoerythromycin A

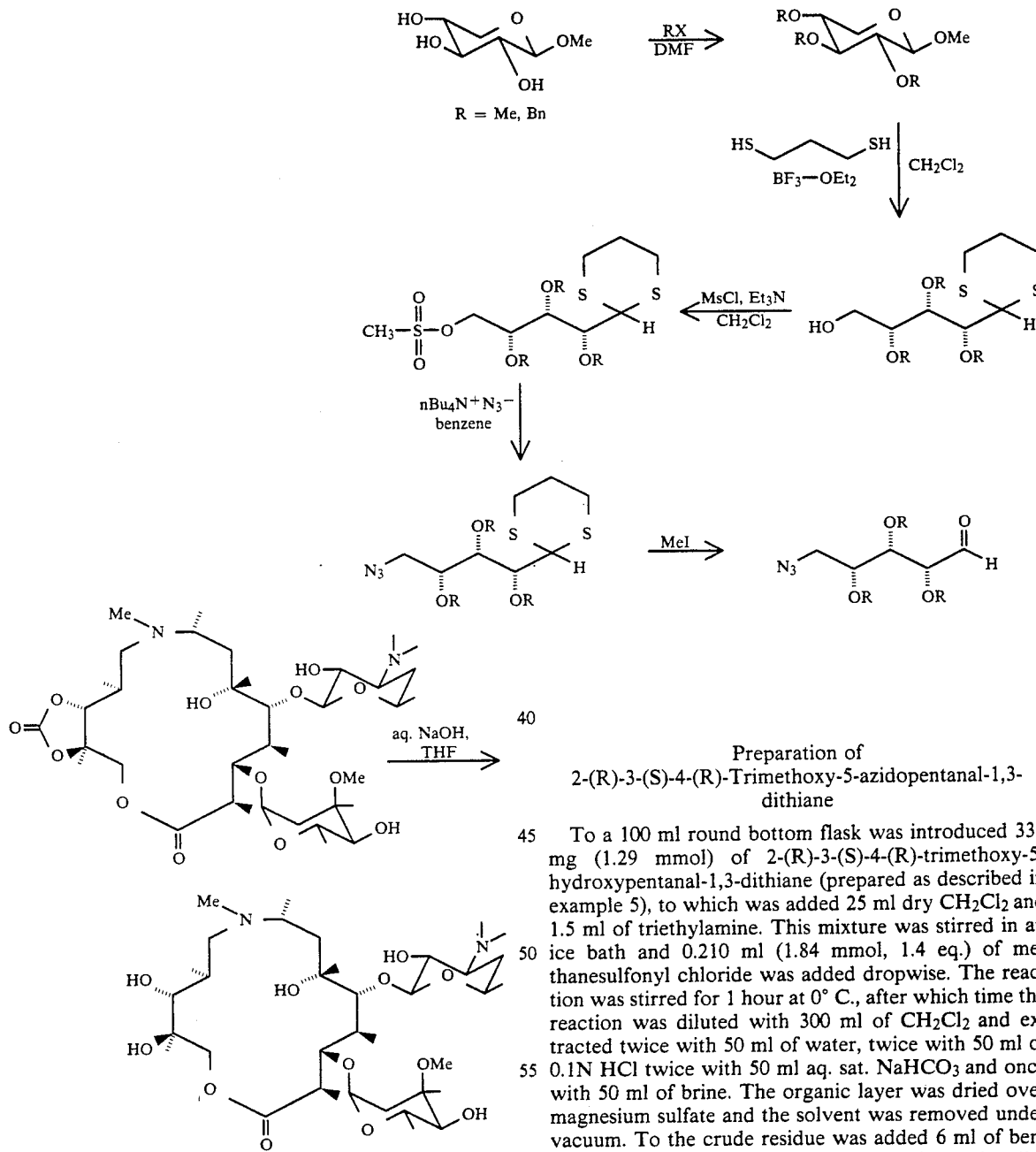

Following the procedure of Hunt and Tyler in *J. Chem. Soc. Perkin Trans.* 2, 1990 2157, a 50 ml round bottom flask is charged with 50 mg of 8a-methyl-8a-aza-9-deoxo-4,15-bisnor-8a-homoerythromycin A 11-O,12-O-carbonate, to which is added 4 ml THF and 1 ml of 0.1N aq. NaOH. After 41 hours, the reaction is added to ethyl acetate and extracted with water. The organic phase is dried with MgSO₄, and the solvent is removed under vacuum. The residue is taken up in 94:6:1 CH₂Cl₂/MeOH/aq. NH₃ and chromatographed on silica gel using the same solvent mixture. This affords the desired product 8a-methyl-8a-aza-9-deoxo-14,15-bisnor-8a-homoerythromycin A.

EXAMPLE 21

Preparation of
2-(R)-3-(S)-4-(R)-trialkoxy-5-azidopentanal

Preparation of
2-(R)-3-(S)-4-(R)-Trimethoxy-5-azidopentanal-1,3-dithiane

To a 100 ml round bottom flask was introduced 337 mg (1.29 mmol) of 2-(R)-3-(S)-4-(R)-trimethoxy-5-hydroxypentanal-1,3-dithiane (prepared as described in example 5), to which was added 25 ml dry CH₂Cl₂ and 1.5 ml of triethylamine. This mixture was stirred in an ice bath and 0.210 ml (1.84 mmol, 1.4 eq.) of methanesulfonyl chloride was added dropwise. The reaction was stirred for 1 hour at 0° C., after which time the reaction was diluted with 300 ml of CH₂Cl₂ and extracted twice with 50 ml of water, twice with 50 ml of 0.1N HCl twice with 50 ml aq. sat. NaHCO₃ and once with 50 ml of brine. The organic layer was dried over magnesium sulfate and the solvent was removed under vacuum. To the crude residue was added 6 ml of benzene and 800 mg of tetra-n-butylammonium azide (2.8 mmol, 2.2 eq.). The reaction was heated at 65° C. for 18 hours, after which time the reaction was diluted with 300 ml of CH₂Cl₂ and extracted twice with 50 ml of water and once with 50 ml of brine. The organic layer was dried over MgSO₄ and the solvent was removed under vacuum. The residue was chromatographed on silica, eluting with 11% ethyl acetate/hexane. This afforded 290 mg (85% for two steps) of 2-(R)-3-(S)-4-(R)-trimethoxy-5-azidopentanal-1,3-dithiane.

Preparation of 2-(R)-3-(S)-4-(R)-Trimethoxy-5-azidopentanal

To a 100 ml round bottom flask was introduced 69 mg (0.22 mmol) of 2-(R)-3-(S)-4-(R)-trimethoxy-5-azidopentanal-1,3-dithiane, to which was added 1.5 ml acetone, 1.5 ml acetonitrile, and 0.5 ml of water. To this mixture was added 0.25 ml of 2,4,6-collidine and 0.115 ml of MeI (1.85 mmol, 8.4 eq.). The reaction was heated at 55° C. for 7 hours, after which time the reaction was diluted with 300 ml of $CH_2Cl_2$ and extracted twice with 50 ml of water and once with 50 ml of brine. The organic layer was dried over $MgSO_4$ and the solvent was removed under vacuum. The residue was chromatographed on silica, eluting with 20% ethyl acetate/hexane. This afforded 26 mg (52%) of 2-(R)-3-(S)-4-(R)-trimethoxy-5-azidopentanal.

Selected spectral data for 2-(R)-3-(S)-4-(R)-trimethoxy-5-azidopentanal.:

$^1$H NMR (400 MHz, $CDCl_3$) δ 9.72 (d, J=0.7 Hz, 1H), 3.79 (d, J=4.4 Hz, 1H), 3.66 (dd, J=3.5 Hz, 4.5 Hz, 2H), 3.50 (s, 3H), 3.49 (s, 3H), 3.49 (m, 1H), 3.43 (m, 1H), 3.35 (s, 3H).

Preparation of 2-(R)-3-(S)-4-(R)-Tribenzyloxy-5-azidopentanal

Starting with 2-(R)-3-(S)-4-(R)-tribenzyloxy-5-hydroxypentanal-1,3-dithiane (prepared as described in example 5), the procedures given above are followed to prepare 2-(R)-3-(S)-4-(R)-tribenzyloxy-5-azidopentanal.

EXAMPLE 22

General Preparation of Carbohydrate Derived Azidoalkanals

Using the procedure of example 21, other monosaccharides can be converted into an azidoalkanal. A representative but nonlimiting sampling of the compounds that can be produced in this manner include those in the following table.

TABLE 10-1

| Starting Carbohydrate | Azido Aldehyde R = Me or Bn |
|---|---|

TABLE 10-1-continued

| Starting Carbohydrate | Azido Aldehyde R = Me or Bn |
|---|---| table:

TABLE 10-2

| Starting Carbohydrate | Azido Aldehyde R = Me or Bn |
|---|---|

TABLE 10-3
| Starting Carbohydrate | Azido Aldehyde R = Me or Bn |
|---|---|
| (structure) | (structure) |
| (structure) | (structure) |
| (structure) | (structure) |
| (structure) | (structure) |
TABLE 10-4
| Starting Carbohydrate | Azido Aldehyde R = Me or Bn |
|---|---|
| (structure) | (structure) |
| (structure) | (structure) |
| (structure) | (structure) |
EXAMPLE 23
Preparation of 2-(R)-hexyl-3-(R)-hydroxy-4-hydroxy-4-methyl-5-azidopentanal 3-O,4O-acetonide
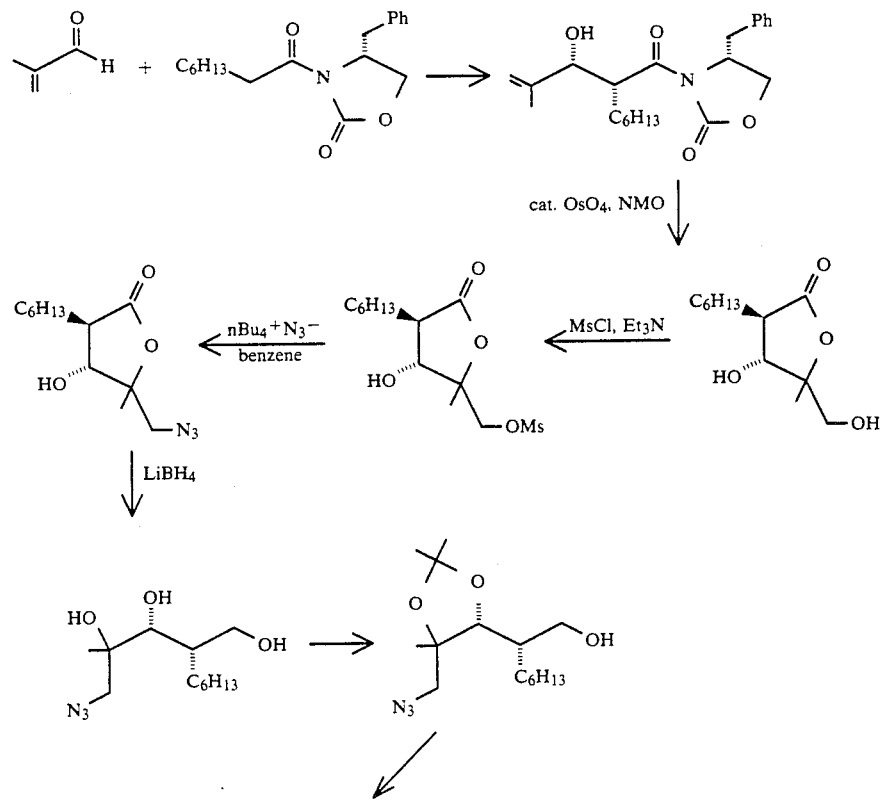

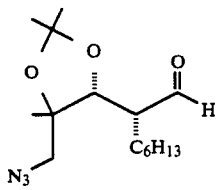

Preparation of
2-(R)-hexyl-3-(R)-hydroxy-4-methyl-4-methanesulfonyloxymethylbutyrolactone 2-(R)-Hexyl-3-(R)-hydroxy-4-methyl-4-hydroxymethylbutyrolactone (prepared as described in example 7) is reacted with 1 eq. of methanesulfonylchloride and 3 eq. of triethylamine in dry methylene chloride at 0° C. to afford 2-(R)-hexyl-3-(R)-hydroxy-4-methyl-4-methanesulfonyloxymethylbutyrolactone.

Preparation of
2-(R)-hexyl-3-(R)-hydroxy-4-methyl-4-azidomethylbutyrolactone 2-(R)-hexyl-3-(R)-hydroxy-4-methyl-4-methanesulfonyloxymethylbutyrolactone is reacted with 3 eq. of tetra-n-butylammonium azide in benzene at 65° C. to afford 2-(R)-hexyl-3-(R)-hydroxy-4-methyl-4-azidomethylbutyrolactone.

Preparation of
2-(S)-hexyl-3-(R)-hydroxy-4-hydroxy-4-methyl-5-azidopentanal 3-(O),4-(O)-acetonide 2-(R)-Hexyl-3-(R)-hydroxy-4-methyl-4-azidomethylbutyrolactone is converted to 2-(S)-hexyl-3-(R)-hydroxy-4-hydroxy-4-methyl-5-azidopentanal 3-(O),4-(O)-acetonide in exactly the same fashion that 2-(R)-Hexyl-3-(R)-hydroxy-4-methyl-4-t-butyldiphenylsilyloxymethylbutyrolactone is converted to 2-(S)-hexyl-3-(R)-hydroxy-4-hydroxy-4-methyl-5-t-butyldiphenylsilyloxypentanal 3-(O),4-(O)-acetonide as described in example 7.

EXAMPLE 24

General Preparation of
2-(X)-alkyl-3-(X)-hydroxy-4-hydroxy-4-alkyl-5-azidopentanal 3-O,4-O-acetonide (X=R or S)

Following the procedure given in example 23, a variety of 2-(X)-alkyl-3-(X)-hydroxy-4-hydroxy-4-alkyl-5-azidopentanal 3-O,4-O-acetonides (X=R or S) can be prepared. A representative but nonlimiting sampling of the compounds that can be produced in this manner include those in the following table:

TABLE 11-1

TABLE 11-1-continued

TABLE 11-2

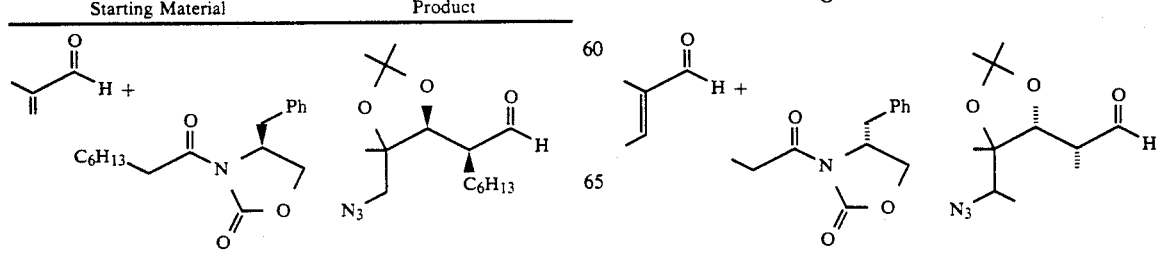

EXAMPLE 25

Preparation of
2-(R)-hexyl-3-(R)-hydroxy-4-hydroxy-4-methyl-5-azidopentanal 3-O,4-O-carbonate

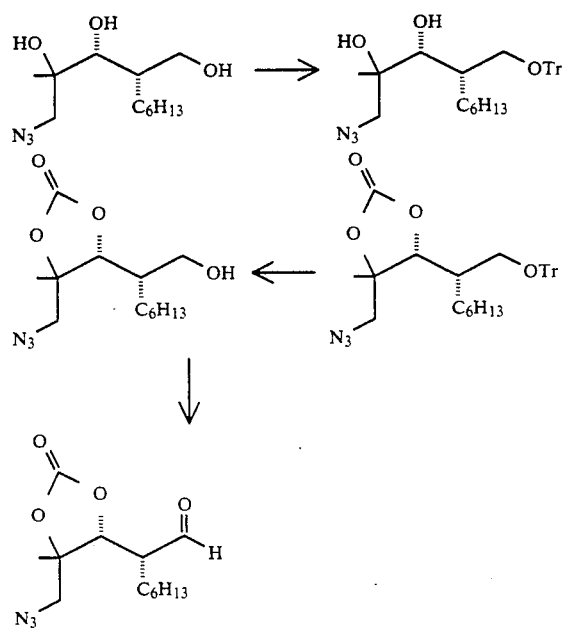

Preparation of
2-(S)-Hexyl-3-(R)-hydroxy-4-hydroxy-4-methyl-5-azidopentanal 3-O,4-O-carbonate 2-(S)-Hexyl-3-(R)-hydroxy-4-hydroxy-4-methyl-5-azidopentanal 3-O,4-O-carbonate is prepared from 1-hydroxy-2-(S)-hexyl-3-(R)-hydroxy-4-hydroxy-4-methyl-5-azidopentane (prepared as described in example 23) in exactly the same fashion that 2-(S)-hexyl-3-(R)-hydroxy-4-hydroxy-4-methyl-5-t-butyldiphenylsiloxypentanal 3-O,4-O-carbonate is prepared from 1-hydroxy-2-(S)-hexyl-3-(R)-hydroxy-4-hydroxy-4-methyl-5-t-butyldiphenylsiloxypentane as described in example 9.

EXAMPLE 26

General Preparation of
2-(X)-alkyl-3-(X)-hydroxy-4-hydroxy-4-alkyl-5-azidopentanal 3-O,4-O-carbonate (X=R or S)

Following the procedure given in example 25, a variety of 2-(X)-alkyl-3-(X)-hydroxy-4-hydroxy-4-alkyl-5-azidopentanal 3-O,4-O-carbonates (X=R or S) can be prepared. A representative but nonlimiting sampling of the compounds that can be produced in this manner include those in the following table:

TABLE 12-2-continued

| Starting Materials | End Products |
|---|---|
| 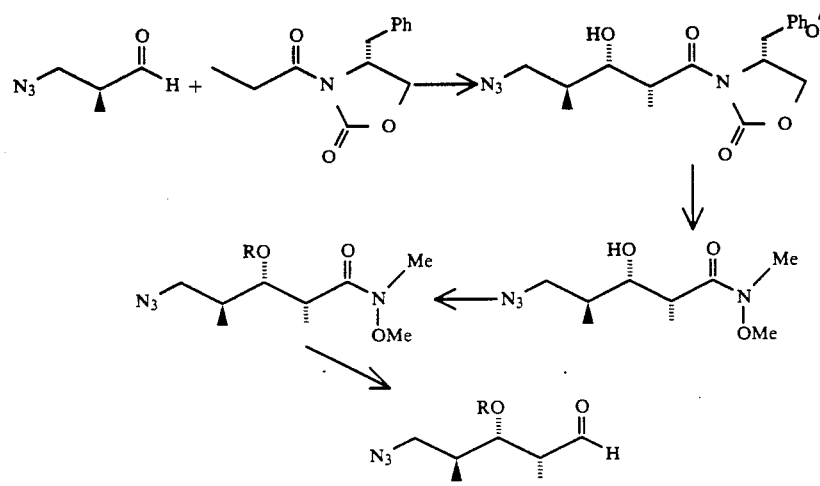 | |

EXAMPLE 27

Preparation of 2-(R)-methyl-3-(S)-alkoxy-4-(S)-methyl-5-azidopentanal

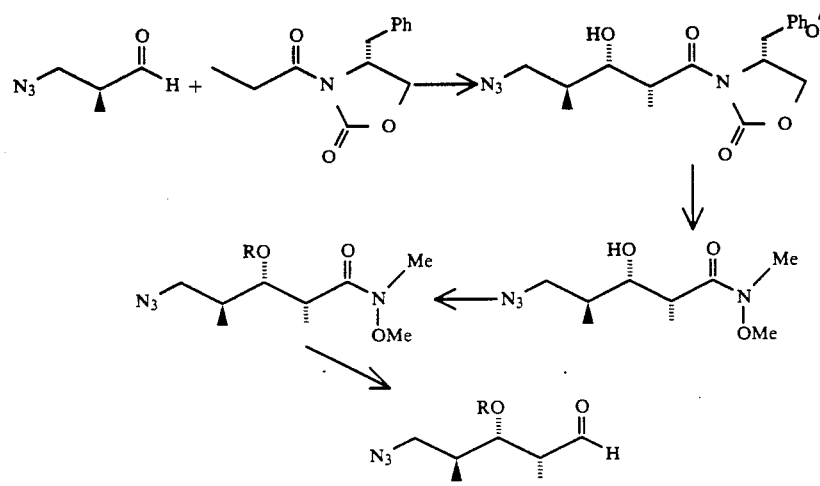

This material is prepared starting from (R)-3-(1-oxopropyl)-4-(phenylmethyl)-2-oxazolidinone and 2-(S)-methyl-3-azidopropanal following the method given in example 9.

EXAMPLE 28

General Preparation of 2-(X)-alkyl-3-(X)-alkoxy-4-substituted-5-azidoalkanals (X=R or S)

Following the procedure given in example 27, a variety of 2-(X)-alkyl-3-(X)-alkoxy-4-substituted-5-azidoalkanals (X=R or S) can be prepared. A representative but nonlimiting sampling of the compounds that can be produced in this manner include those in the following table:

TABLE 13-1

| Starting Materials | Products (R = Me, Bn) |
|---|---|

TABLE 13-1-continued

| Starting Materials | Products (R = Me, Bn) |
|---|---|

TABLE 13-2

| Starting Materials | Product |
|---|---|

TABLE 13-2-continued

| Starting Materials | Product |
|---|---|
| (structures) | (structures) |
| (structures) | (structures) |
| (structures) | (structures) |
| (structures) | (structures) |

TABLE 13-3

| Starting Materials | Products (R = Me, Bn) |
|---|---|
| (structures) | (structures) |
| (structures) | (structures) |
| (structures) | (structures) |

TABLE 13-3-continued

| Starting Materials | Products (R = Me, Bn) |
|---|---|
| (structures) | (structures) |

EXAMPLE 29

Preparation of (S)-3-Azidobutanal

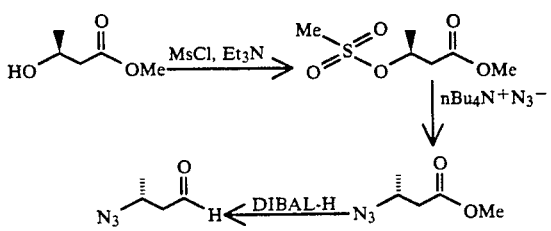

Preparation of Methyl (S)-3-Azidobutanoate

To methyl (S)-3-hydroxybutanoate (1 mmol) is added 25 ml dry $CH_2Cl_2$ and 1.5 ml of triethylamine. This mixture is stirred in an ice bath and 1.4 eq. of methanesulfonyl chloride is added dropwise. The reaction is stirred for 1 hour at 0° C., after which time the reaction is diluted with 300 ml of $CH_2Cl_2$ and extracted twice with 50 ml of water, twice with 50 ml of 0.1N HCl twice with 50 ml aq. sat. $NaHCO_3$ and once with 50 ml of brine. The organic layer is dried over magnesium sulfate and the solvent is removed under vacuum. To the crude residue is added 6 ml of benzene and 2.2 eq. of $nBu_4N^+N_3^-$. The reaction is heated at 65° C. for 18 hours, after which time the reaction is diluted with 300 ml of $CH_2Cl_2$ and extracted twice with 50 ml of water and once with 50 ml of brine. The organic layer is dried over $MgSO_4$ and the solvent is removed under vacuum. The residue is chromatographed on silica, affording methyl (S)-3-azidobutanoate.

Preparation of (S)-3-Azidobutanal

Methyl (S)-3-hydroxybutanoate is reduced with diisobutylaluminum hydride following the procedure given in example 1 to afford (S)-azidobutanal.

EXAMPLE 30

General Preparation of Azido Aldehydes from Hydroxyesters

Following the procedure given in example 29, a variety of hydroxyesters can be converted to azidoaldehydes. A representative but nonlimiting sampling of the compounds that can be produced in this manner include those in the following table:

TABLE 14

| hydroxyester | azidoaldehyde |
|---|---|
| (structure) | (structure) |

TABLE 14-continued

| hydroxyester | azidoaldehyde |
|---|---|

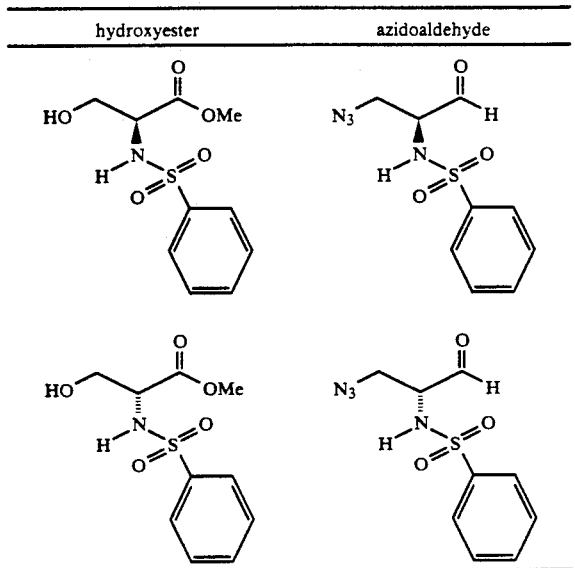

EXAMPLE 31

Preparation of 3-azidopropanal

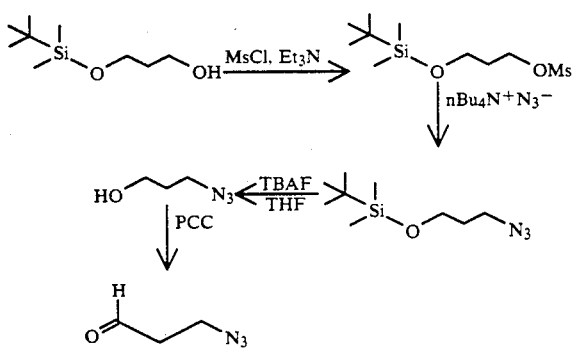

1-Azido-3-t-butyldimethylsiloxypropane

Following the procedure given in example 29, t-butyldimethylsiloxypropanol (prepared according to the method of McDougal et al, *J. Org. Chem.* 1986, 51, 3388) is first reacted with methanesulfonyl chloride in methylene chloride in the presence of triethylamine, and then the crude mesylate is reacted with tetra-n-butylammonium azide in benzene to afford 1-azido-3-t-butylsiloxypropane.

1-Azido-3-hydroxypropane

1-Azido-3-t-butylsiloxypropane is reacted with tetra-n-butylammonium fluoride in anhydrous THF to afford 1-azido-3-hydroxypropane.

3-Azidopropanal

Following the procedure given in example 3, 1-azido-3-hydroxypropane is oxidized with pyridinium chlorochromate in methylene chloride to afford 3-azidopropanal.

EXAMPLE 32

General Preparation of Azido Aldehydes from Symmetric Diols

Beginning with t-butyldimethylsilylation according to the method of McDougal et al, *J. Org. Chem.* 1986, 51, 3388, and then following the procedure given in example 31, a variety of symmetric diols can be converted to azido aldehydes. A representative but nonlimiting sampling of the compounds that can be produced in this manner include those in the following table:

TABLE 15

| Starting Diol | t-Butyldimethylsilyl Aldehyde |
|---|---|

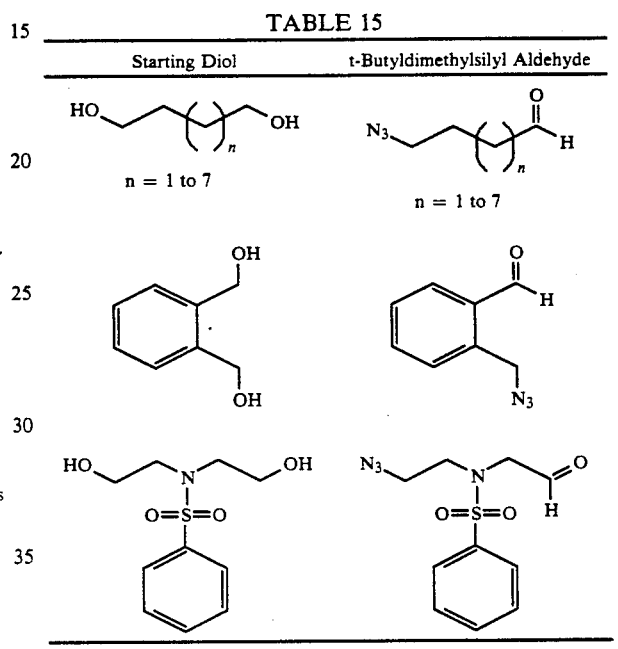

EXAMPLE 33

Preparation of (S)-2-hydroxy-2-methyl-3-azidopropanal (R)-2-Methylglycidol is reacted with lithium azide in 2-methoxyethanol at high temperature to afford (S)-2-hydroxy-2-methyl-3-azidopropanol, which is purified and oxidized using the Dess-Martin periodinane reagent (described in Dess D. B.; Martin, *J. C. J. Am, Chem. Soc.*, 1991, 113, 7277) to afford (S)-2-hydroxy-2-methyl-3-azidopropanal.

EXAMPLE 34

General Preparation of Azido Aldehydes from Epoxides

Following the procedure given in Example 33, a variety of epoxides can be convened to azido aldehydes. A representative but nonlimiting sampling of the compounds that can be produced in this manner include those in the following table:

TABLE 16

| Starting Epoxide | Azido Aldehyde |
|---|---|
|  | |
| 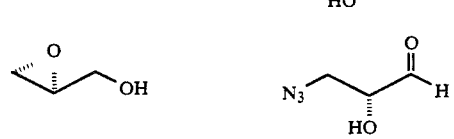 | |

TABLE 16-continued

| Starting Epoxide | Azido Aldehyde |
|---|---|
|  | |

EXAMPLE 35

Preparation of 8a-methyl-8a-aza-9-deoxo-10-demethyl-11-dehydroxy-12,13,14,15-tetrakisnor-8a-homoerythromycin A lactam

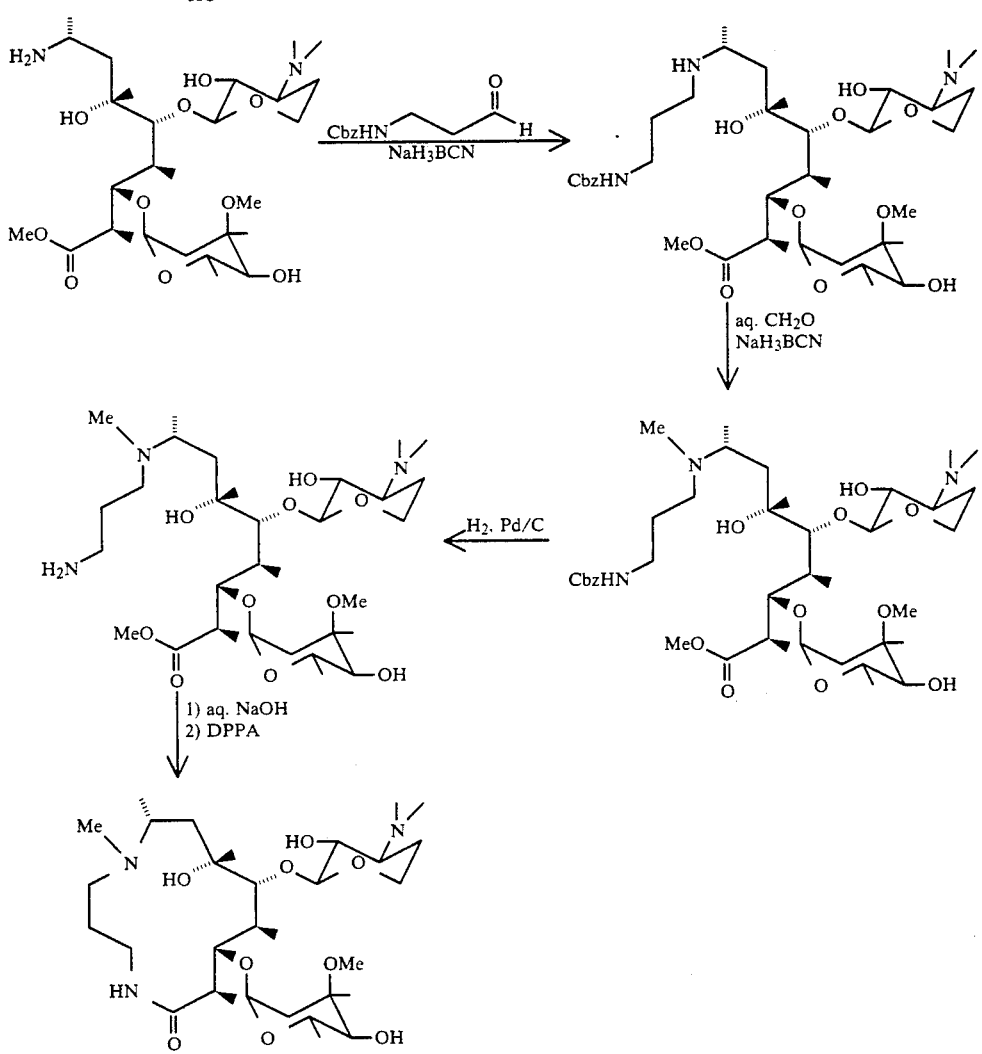

Preparation of 8a-(3-benzyloxycarbonylaminopropyl)-8a-aza-9,10,11,12,13,14,15-heptanor-8a-homoerythromycin A To a 100 ml round bottom flask was introduced 300 mg (0.507 mmol) of 8a-aza-9,10,11,12,13,14,15-heptan-

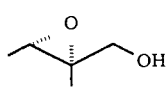 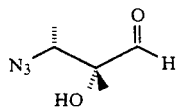

or-8a-homoerythromycin A to which was added 10 ml MeOH, 120 mg (0.61 mmol, 1.2 eq.) of the aldehyde starting material, 55 mg NaH₃BCN (0.82 mmol, 1.6 eq.), and 400 μl of AcOH. The reaction was stirred at room temperature and monitored by TLC (93:7:1 $CH_2Cl_2$/MeOH/aq. $NH_3$, product is higher $R_f$ than starting material). After 24 hours, the reaction was not complete as judged by TLC, and 30 mg (0.15 mmol, 0.3 eq.) of the aldehyde and 30 mg more NaH₃BCN (0.97 mmol, 1.55 eq.) was added. After stirring an additional 24 hours, only a small amount of starting material remained as judged by TLC. The solvent was removed under vacuum and the residue was taken up in 94:6:1 $CH_2Cl_2$/MeOH/aq. $NH_3$ and chromatographed on silica gel using the same solvent mixture. This afforded 333 mg (83%) of the desired adduct.

Selected spectral data for 8a-(3-benzyloxycarbonylaminopropyl)-8a-aza-9,10,11,12,13,14,15-heptanor-8a-homoerythromycin A: ¹H NMR (400 MHz, CDCl₃) δ 7.32 (m, 5H), 5.45 (br t, CbzNH), 5.05 (s, $PhCH_2O$—), 4.65 (d, H-1", J=4.4 Hz), 4.32 (d, H-1', J=7.3 Hz), 4.07 (dd, H-3, J=4.5, 6.1), 3.96 (m, H-5"), 3.64 (s, COOCH₃), 3.52 (d, H-5, J=3.3), 3.30 (dd, H-2'), 3.24 (s, OCH₃), 2.97 (d, J=9.4, H-4"), 2.78 (dq, H-2), 2.51 (m, H-3'), 2.27 (s, N(CH₃)₂), (1.68, br d, H-4'), 1.28 & 1.17 (singlets, 6-Me and 3"-Me), 1.26, 1.22 (J=6.2), 1.20 (J=5.9), 1.13 (J=7.0) & 1.04 (J=7.1) (methyl doublets).

FAB MS: 784 (M+H⁺)

Preparation of 8a-methyl-8a-(3-benzyloxycarbonylaminopropyl)-8a-aza-9,10,11,12,13,14,15-heptanor-8a-homoerythromycin A To a 50 ml round bottom flask was introduced 330 mg (0.42 mmol) of 8a-(3-benzyloxycarbonylaminopropyl)-8a-aza-9,10,11,12,13,14,15-heptanor-8a-homoerythromycin A, to which was added 5 ml MeOH, 0.2 ml 37% aq. formaldehyde and 30 mg NaH₃BCN (0.97 mmol, 2.3 eq.) The reaction was stirred at room temperature and monitored by TLC (93:7:1 $CH_2Cl_2$/MeOH/aq. $NH_3$, product is higher $R_f$ than starting material). After 2 hours, the reaction was judged to be complete by TLC. The solvent was removed under vacuum and the residue was taken up in 94:6:1 $CH_2Cl_2$/MeOH/aq. $NH_3$ and chromatographed on silica gel using the same solvent mixture. This afforded 273 mg of the desired product (81%).

Selected spectral data for 8a-methyl-8a-(3-benzyloxycarbonyl aminopropyl)-8a-aza-9,10,11,12,13,14,15-heptanor-8a-homoerythromycin A:

¹H NMR (400 MHz, CDCl₃) δ 7.32 (m, 5H), 5.3 (br t, CbzNH), 5.03 (s, PhCH₂O—), 4.61 (d, H-1", J=4.5 Hz), 4.36 (d, H-1', J=1'7.3 Hz), 4.11 (dd, H-3, J=3.0, 6.7), 3.96 (m, H-5"), 3.59 (s, COOCH₃), 3.48 (d, H-5'), 3.23 (s, OCH₃), 2.94 (d, J=9.5, H-4"), 2.80 (m, H-2), 2.46 (m, H-3'), 2.23 (s, N(CH₃)₂), 2.18 (s, 8a-N—CH₃), 1.28 & 1.15 (singlets, 6-Me and 3"-Me), 1.20 (J=6.3), 1.18 (J=6.1 ), 1.06 (J=6.8), 1.06 (J=6.8) & 0.90 (J=6.3) (methyl doublets).

FAB MS: 798 (M+H⁺)

Preparation of 8a-methyl-8a-(3-aminopropyl)-8a-aza-9,10,11,12,13,14,15-heptanor-8a-homoerythromycin A To a 100 ml round bottom flask was introduced 200 mg (0.260 mmol) of 8a-methyl-8a-(3-benzyloxycarbonyl-aminopropyl)-8a-aza-9,10,11,12,13,14,15-heptanor-8a-homoerythromycin A, to which was added 10 ml 95% EtOH and 0.35 ml AcOH, 480 mg of NaOAc, and 1.5 ml water. The catalyst 10% Pd/C (400 mg) was added and the reaction was stirred at room temperature under a hydrogen atmosphere and monitored by TLC (93:7:1 $CH_2Cl_2$/MeOH/aq. $NH_3$, product is lower $R_f$ than starting material). After 5 hours, the reaction was judged to be complete by TLC. Most of the solvent was removed under vacuum, and the residue was diluted with 300 ml of methylene chloride and extracted 4 times with 50 ml of water. The organic layer was dried over MgSO₄ and the solvent was removed under vacuum. NMR revealed that the compound was sufficiently pure to be used directly in the next step. This afforded 140 mg (84% yield) of the desired product.

Selected spectral data for 8a-methyl-8a-(3-aminopropyl)-8a-aza-9,10,11,12,13,14,15-heptanor-8a-homoerythromycin A:

¹H NMR (400 MHz, CDCl₃) δ 4.61 (d, H-1", J=4.4 Hz), 4.40 (d, H-1', J=7.3 Hz), 4.10 (dd, H-3, J=2.4, 7.8), 4.02 (m, H-5"), 3.62 (s, COOCH₃), 3.53 (d, J=3.0, H-5), 3.48 (m, H-5'), 3.26 (s, OCH₃), 2.95 (d, J=9.5, H-4"), 2.86 (m, H-2), 2.48 (m, H-3'), 2.26 (s, N(CH₃)₂), 2.16 (s, 8a—N-CH₃), 1.30 & 1.18 (singlets, 6-Me and 3"-Me), 1.22 (J=6.4), 1.20 (J=6.1), 1.09 (J=7.2), 1.08 (J=7.0) & 0.89 (J=6.6) (methyl doublets).

¹³C NMR (100 MHz, CDCl3) δ 176.6, 102.8, 95.1, 81.5, 80.8, 78.0, 75.3, 72.8, 70.6, 69.3, 65.4, 65.1, 55.9, 51.5, 50.3, 49.4, 40.6, 40.4, 39.9, 36.1, 36.0, 35.3, 35.2, 31.1, 29.0, 28.9, 27.0, 21.6, 21.2, 17.9, 12.4, 11.6, 9.9.

FAB MS: 665 (M+H⁺)

Preparation of 8a-methyl-8a-aza-9-deoxo-10-demethyl-11-dehydroxy-12,13,14,15-tetrakisnor-8a-homoerythromycin A lactam To a 50 ml round bottom flask was introduced 140 mg (0.210 mmol) of 8a-methyl-8a-(3-aminopropyl)-8a-aza-9,10,11,12,13,14,15-heptanor-8a-homoerythromycin A, to which was added 3 ml MeOH, 3 ml THF and 1.5 ml 1N aq. NaOH. The reaction was stirred at room temperature and monitored by TLC (93:7:1 $CH_2Cl_2$/MeOH/aq. $NH_3$, product is baseline). After 24 hours, the reaction was judged to be complete by TLC (only baseline material.) The reaction was added to 50 ml of water and the pH was adjusted to 7.7 with dilute HCl. All solvent was removed under high vacuum and the sample was dried under high vacuum for 24 hours. To the residue was added 20 ml of sieve dried DMF and the reaction was cooled in an ice/salt bath to about −10° C., at which time 300 mg NaHCO₃ and 0.15 ml of diphenylphosphorylazide (191 mg, 0.70 mmol, 3.3 eq.) was added. The reaction was stirred and allowed to warm to room temperature over several hours. After 24 hours, TLC (93:7:1 $CH_2Cl_2$/MeOH/aq. $NH_3$) of the crude reaction showed no material remaining on the baseline, and formation of a single mid $R_f$ spot. Most of the solvent was removed under high vacuum, and the residue was taken up in 200 ml of methylene chloride and washed three times with water. The organic layer was dried over MgSO₄ and the solvent was removed under high vacuum. The residue was taken up in 94:6:1 $CH_2Cl_2$/MeOH/aq. $NH_3$ and chromatographed on silica gel using the same solvent mixture. This afforded 106 mg (80% yield) of the desired product.

Selected spectral data for 8a-methyl-8a-aza-9-deoxo-10-demethyl-11-dehydroxy- 12,13,14,15-tetrakisnor-8a-homoerythromycin A lactam:

1H NMR (400 MHz, CDCl3) δ4.81 (d, H-1", J=4.8 Hz), 4.36 (d, H-1', J=7.1 Hz), 4.13 (br d, H-3, J=8 Hz), 4.00 (m, H-5"), 3.58 (d, J=8.5 Hz, H-5), 3.27 (s, OCH3), 2.99 (br t, H-4"), 2.74 (m, H-2), 2.40 (m, H-3'), 2.23 (s, N(CH3)2), 2.22 (s, 8a-N—CH3), 1.43 & 1.19 (singlets, 6-Me and 3"-Me), 1.30 (J=6.2 Hz), 1.20, 1.19, 1.08 (J=7.4) & 0.87 (J=6.6) (methyl doublets).

13C NMR (100 MHz, CDCl3) δ 175.5, 103.6, 96.5, 82.6, 78.7, 78.0, 72.5, 70.9, 68.9, 65.5, 57.0, 49.5, 47.2, 40.3, 39.3, 38.8, 35.0, 28.6, 21.5, 21.4, 18.6, 17.3, 12.2, 9.6.

FAB MS: 633 (M+H+)

Elemental analysis: Calcd for C31H58N2O10·H2O: C, 59.17; H, 9.70; N, 6.47. Found: C, 59.33, 59.35; H, 9.77, 9.78; N, 6.94, 6.90.

EXAMPLE 36

General Preparation of 13-Membered Azalactams

Following the procedures given in examples 35, 38 & 40, 8a-aza-8a-homo-9,10,10a,11,12,12a,13,14,15-nonanorerythromycin A and various azidoaldehydes (which may be prepared as taught in examples 29-34) are used as starting materials for 13-membered azalactams, as diagrammed below:

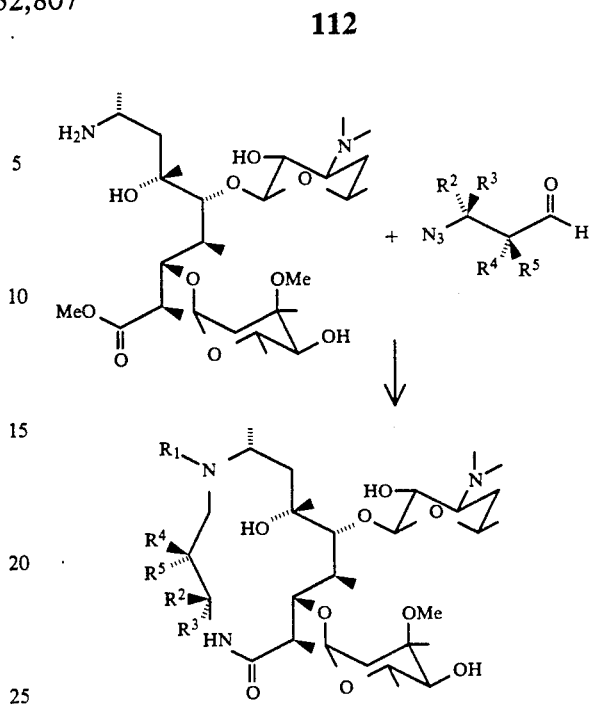

A representative but nonlimiting sampling of the compounds that can be produced in this manner include those in the following table:

TABLE 17-1

| aldehyde | macrocycle (R = C1 to C7 alkyl or aralkyl) |
|---|---|
| (azidoaldehyde structure) | (macrocycle structure) |
| (azidoaldehyde structure) | (macrocycle structure) |
| (azidoaldehyde structure with OBn) | (macrocycle structure with BnO) |

TABLE 17-1-continued
| aldehyde | macrocycle (R = C1 to C7 alkyl or aralkyl) |
|---|---|
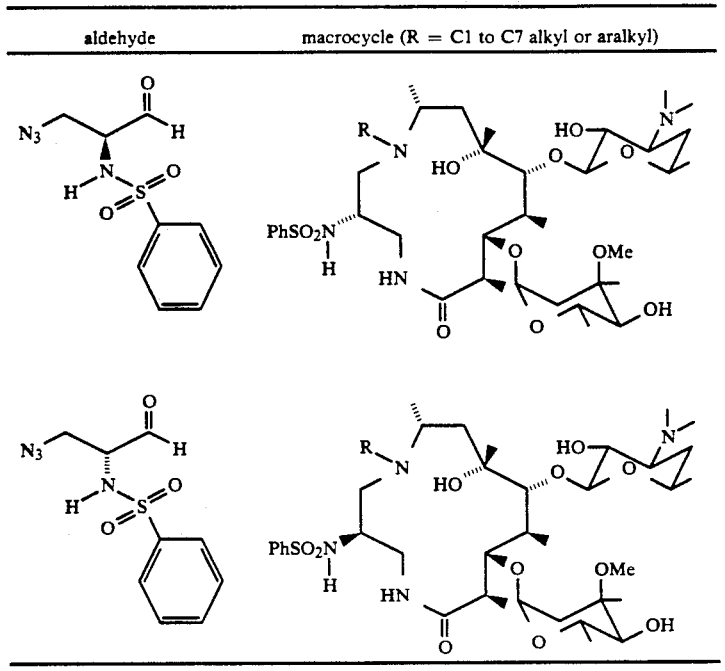
TABLE 17-2
| aldehyde | macrocycle (R = C1 to C7 alkyl or aralkyl) |
|---|---|
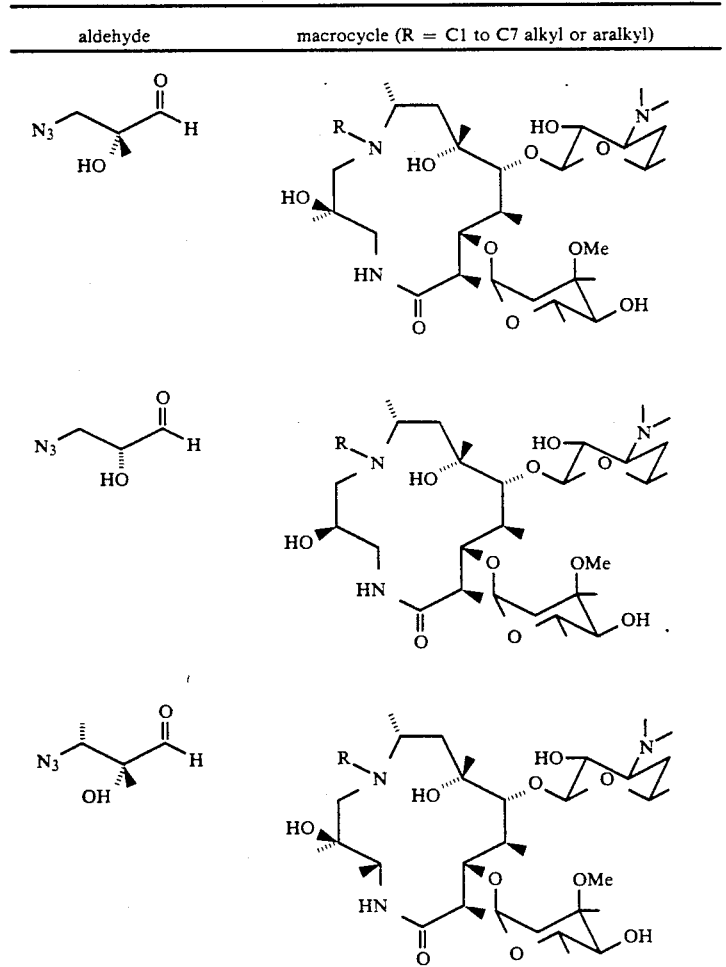

TABLE 17-2-continued

| aldehyde | macrocycle (R = C1 to C7 alkyl or aralkyl) |
|---|---|
| | 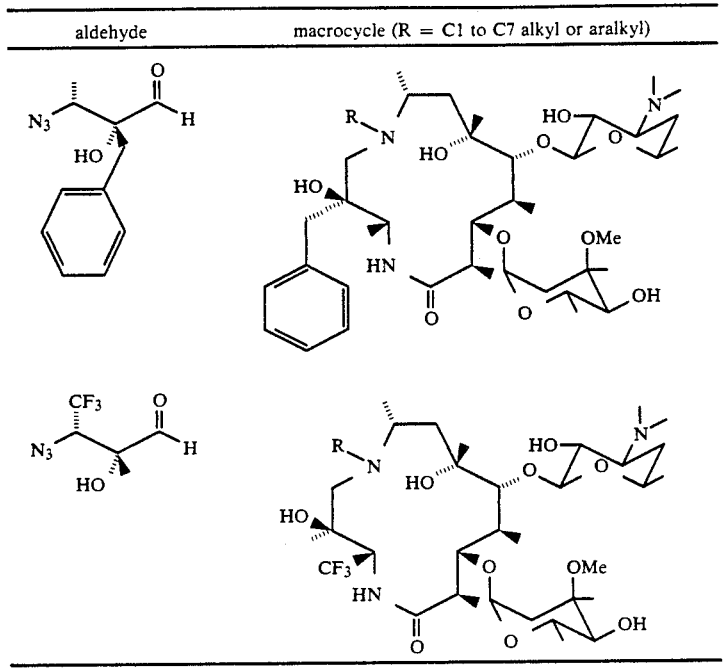 |

EXAMPLE 37

Preparation of
8a-Methyl-8a-aza-9-deoxo-10-demethyl-10-(S)-hydroxy-11-deoxy-12,13,14,15-tetrakisnor-8a-homoerythromycin A lactam

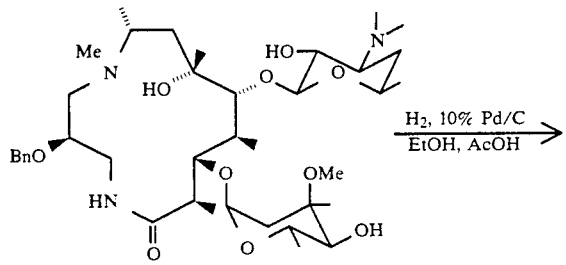

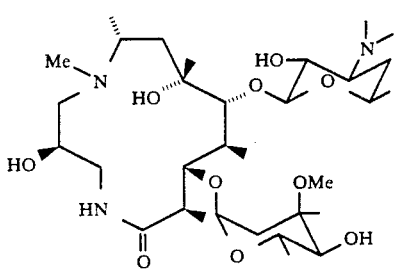

Following the procedure given in example 15, 8a-methyl-8a-aza-9-deoxo-10-demethyl-10-(S)-benzyloxy-11-deoxy-12,13,14,15-tetrakisnor-8a-homoerythromycin A lactam is reduced using $H_2$ and 10% Pd/C in 95% EtOH with AcOH to afford 8a-methyl-8a-aza-9-deoxo-10-demethyl-10-(S)-hydroxy-11-deoxy-12,13,14,15-tetrakisnor-8a-homoerythromycin A lactam.

EXAMPLE 38

Preparation of
8a-aza-9-deoxo-10-demethyl-11-deoxy-12-demethyl-12-deoxy-13,14,15-trisnor-8a-homoerythromycin A lactam Preparation of
8a-benzenesulfonyl-8a-(4-azidobutyl)-8a-aza-9,10,11,12,13,14,15-heptanor-8a-homoerythromycin A Following the procedure described in example 13, 8a-(4-azidobutyl)-8a-aza-9,10,11,12,13,14,15-heptanor-8a-homoerythromycin A is reacted with benzenesulfonyl chloride and triethylamine in methylene chloride to afford 8a-benzenesulfonyl-8a-(4-azidobutyl)-8a-aza-9,10,11,12,13,14,15-heptanor-8a-homoerythromycin A.

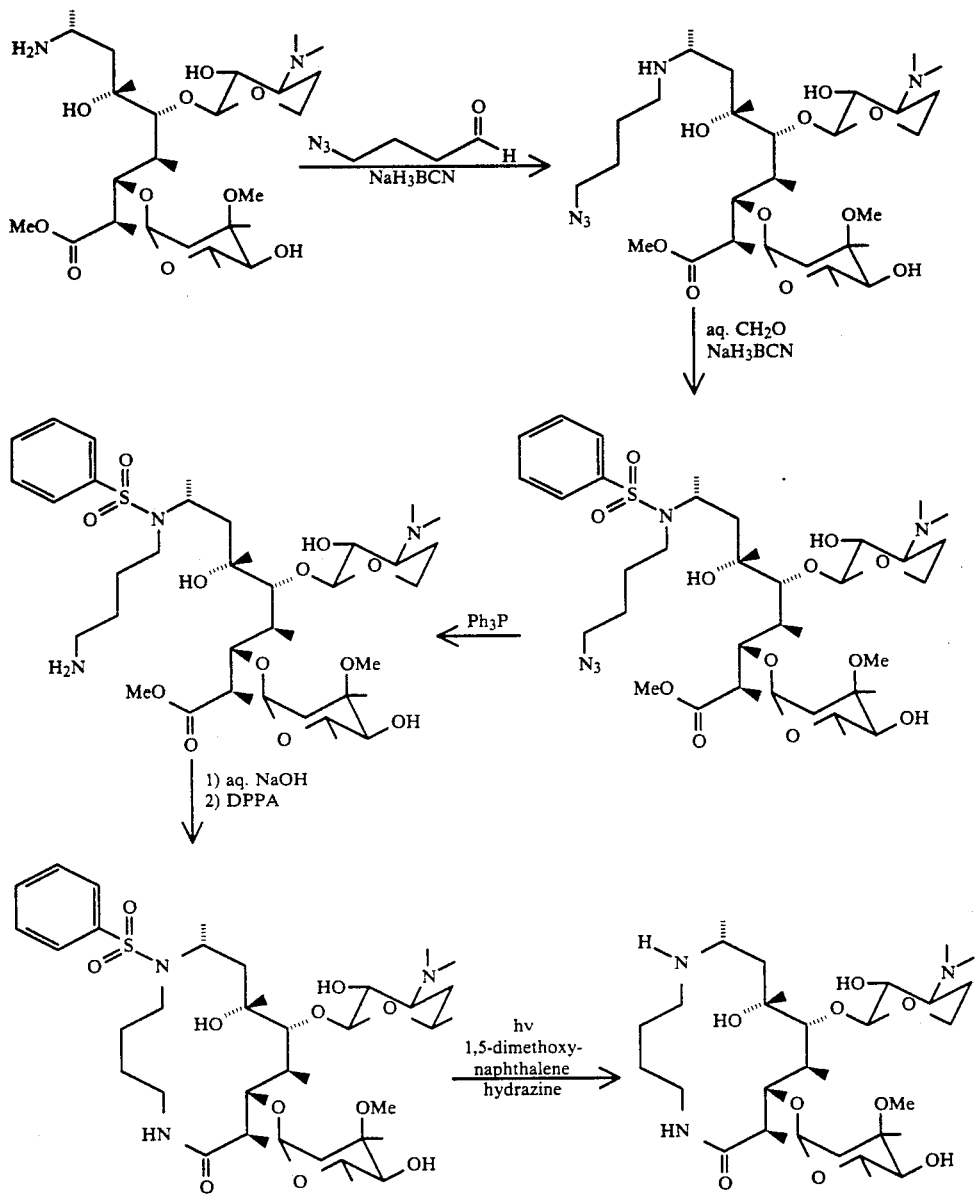

Preparation of 8a-(4-azidobutyl)-8a-aza-9,10,11,12,13,14,15-heptanor-8a-homoerythromycin A Following the procedure described in example 40, 8a-aza-9,10,11,12,13,14,15-heptanor-8a-homoerythromycin A is reacted with 4-azidobutanal using sodium cyanoborohydride in methanol to afford 8a-(4-azidobutyl)-8a-aza-9,10,11,12,13,14,15-heptanor-8a-homoerythromycin A.

Preparation of 8a-benzenesulfonyl-8a-(4-aminobutyl)-8a-aza-9,10,11,12,13,14,15-heptanor-8a-homoerythromycin A Following the procedure described in example 40, 8a-benzenesulfonyl-8a-(4-azidobutyl)-8a-aza-9,10,11,12,13,14,15-heptanor-8a-homoerythromycin A is reacted with triphenylphosphine in aq. THF to afford 8a-benzenesulfonyl-8a-(4-aminobutyl)-8a-aza-9,10,11,12,13,14,15-heptanor-8a-homoerythromycin A.

Preparation of
8a-benzenesulfonyl-8a-aza-9-deoxo-10-demethyl-11-deoxy-12-demethyl-12-deoxy-13,14,15-trisnor-8a-homoerythromycin A lactam Following the procedure described in example 40, 8a-benzenesulfonyl-8a-(4-aminobutyl)-8a-aza-9,10,11,12,13,14,15-heptanor-8a-homoerythromycin A is hydrolysed with aq. NaOH and then cyclized with diphenylphosphorylazide in DMF to afford 8a-benzenesulfonyl-8a-aza-9-deoxo-10-demethyl-11-deoxy-12-demethyl-12-deoxy-13,14,15-trisnor-8a-homoerythromycin A lactam.

Preparation of
8a-aza-9-deoxo-10-demethyl-11-deoxy-12-demethyl-12-deoxy-13,14,15-trisnor-8a-homoerythromycin A lactam Following the procedure described in example 13, 8a-benzenesulfonyl-8a-aza-9-deoxo-10-demethyl-11-deoxy-12-demethyl-12-deoxy-13,14,15-trisnor-8a-homoerythromycin A lactam is photolyzed in the presence of 1,5-dimethoxynaphthalene and hydrazine in 95% ethanol solvent to afford 8a-aza-9-deoxo-10-demethyl-11-deoxy-12-demethyl-12-deoxy-13,14,15-trisnor-8a-homoerythromycin A lactam.

EXAMPLE 39

General Preparation of 14-Membered Azalactams

Following the procedures given in examples 35, 38 & 40, 8a-aza-8a-homo-9,10,11,12,13,14,15-heptanorerythromycin A and various azidoaldehydes (which may be prepared as taught in examples 22, 28 and 32) are used as starting materials for 14-membered azalactams, as diagrammed below:

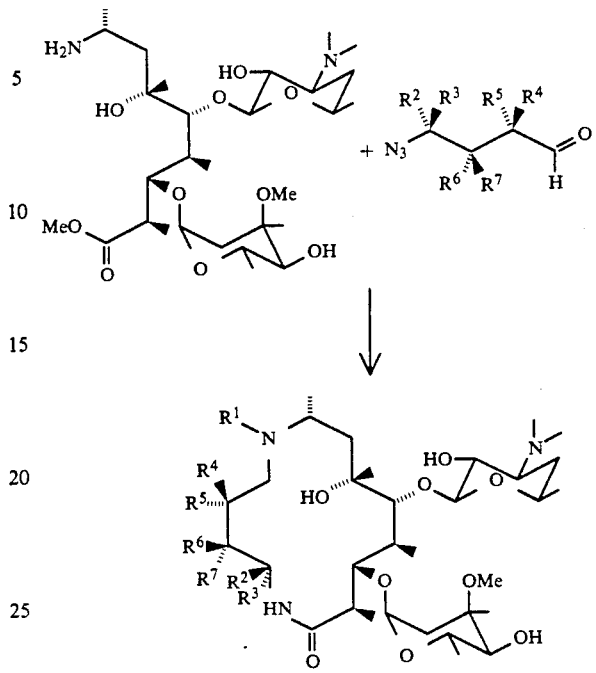

where $R^1$ hydrogen or $C_1$ to $C_7$ alkyl or aralkyl; one of $R^2$ and $R^3$ is hydrogen and the other is hydrogen or $C_1$ to $C_7$ alkyl, cycloalkyl or aryl, which may be substituted with $R^{10}O$, $C_6H_5SO_2HN$ or F; $R^4$, $R^5$, $R^6$ and $R^7$ are hydrogen, $C_1$ to $C_7$ alkyl, fluoroalkyl, cycloalkyl or aryl, $R^{10}O$, $C_6H_5SO_2HN$ or F; $R^{10}$ is methyl, benzyl, or other $C_1$ to $C_7$ alkyl, fluoroalkyl, cycloalkyl or aryl.

A representative but nonlimiting sampling of the compounds that can be produced in this manner include those in the following tables:

TABLE 18-1

| aldehyde (R' = Me, Bn) | macrocycle (R = H or C1 to C7 alkyl or aralkyl) |
|---|---|

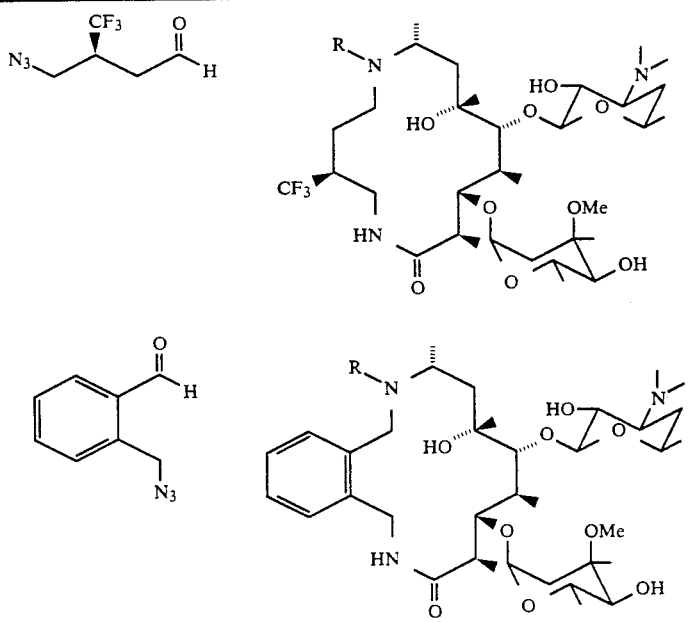

TABLE 18-1-continued
| aldehyde (R' = Me, Bn) | macrocycle (R = H or C1 to C7 alkyl or aralkyl) |
|---|---|
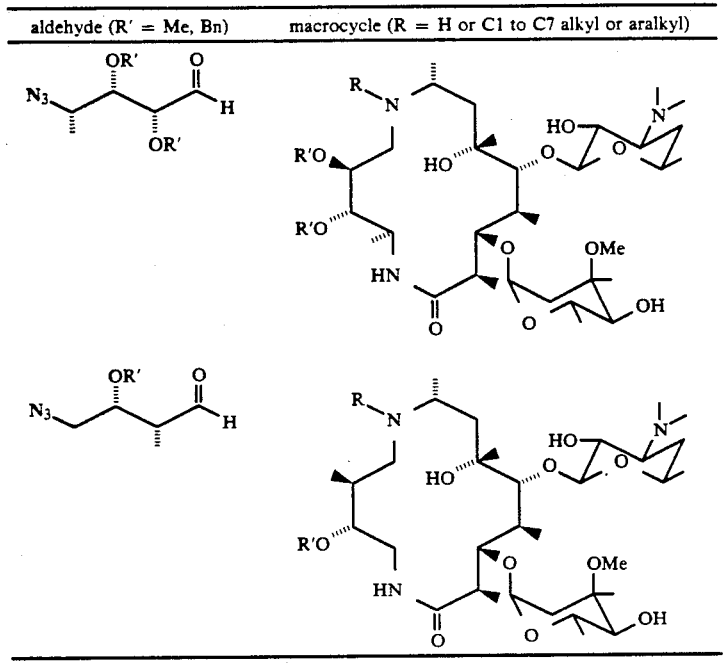
TABLE 18-2
| aldehyde (R' = Me, Bn) | macrocycle (R = H or C1 to C7 alkyl or aralkyl) |
|---|---|
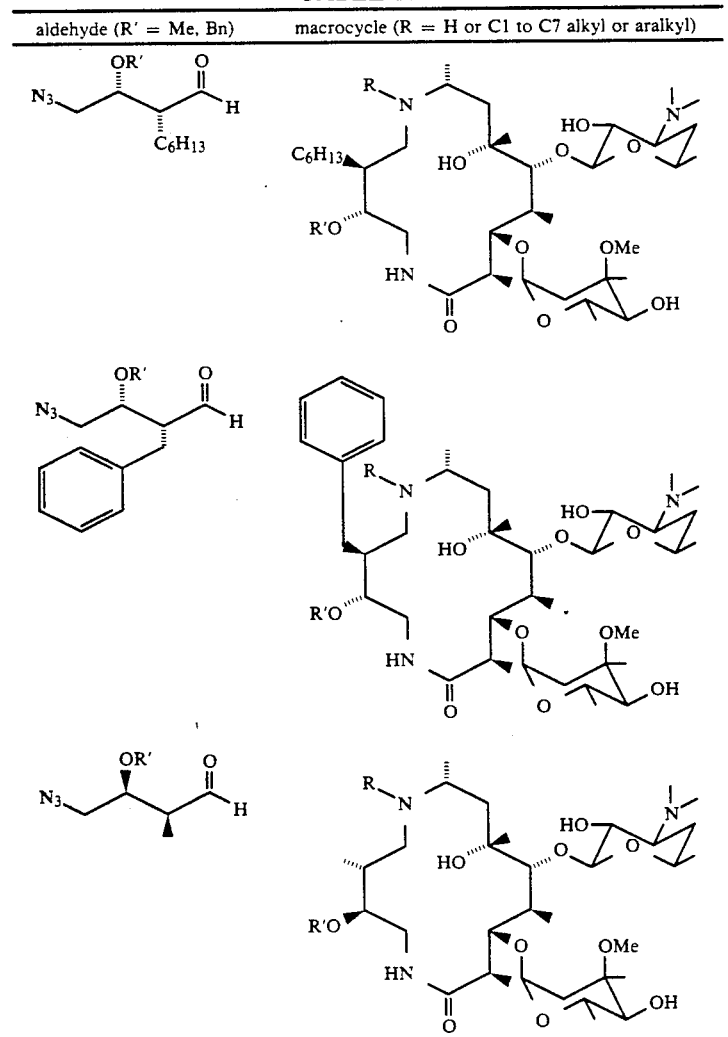

TABLE 18-2-continued
| aldehyde (R' = Me, Bn) | macrocycle (R = H or C1 to C7 alkyl or aralkyl) |
|---|---|
| 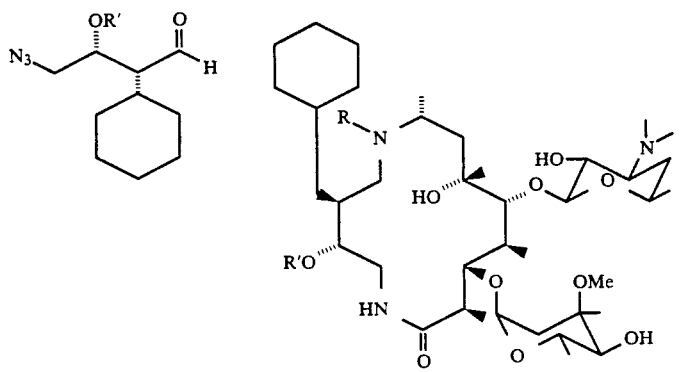 | |
EXAMPLE 40
Preparation of
8a-methyl-8a-aza-9-deoxo-10-demethyl-10-(S)-methoxy-11-O-methyl-12-O-methyl-12-demethyl-14,15-bisnor-8a-homoerythromycin A lactam
Preparation of
8a-(2-(S),3-(S),4-(S)-trimethoxy-5-azidopentyl)-8a-aza-9,10,11,12,13,14,15-heptanor-8a-homoerythromycin A
To a 10 ml round bottom flask was introduced 60 mg (0.101 mmol) of 8a-aza-9,10,11,12,13,14,15-heptanor-8a-
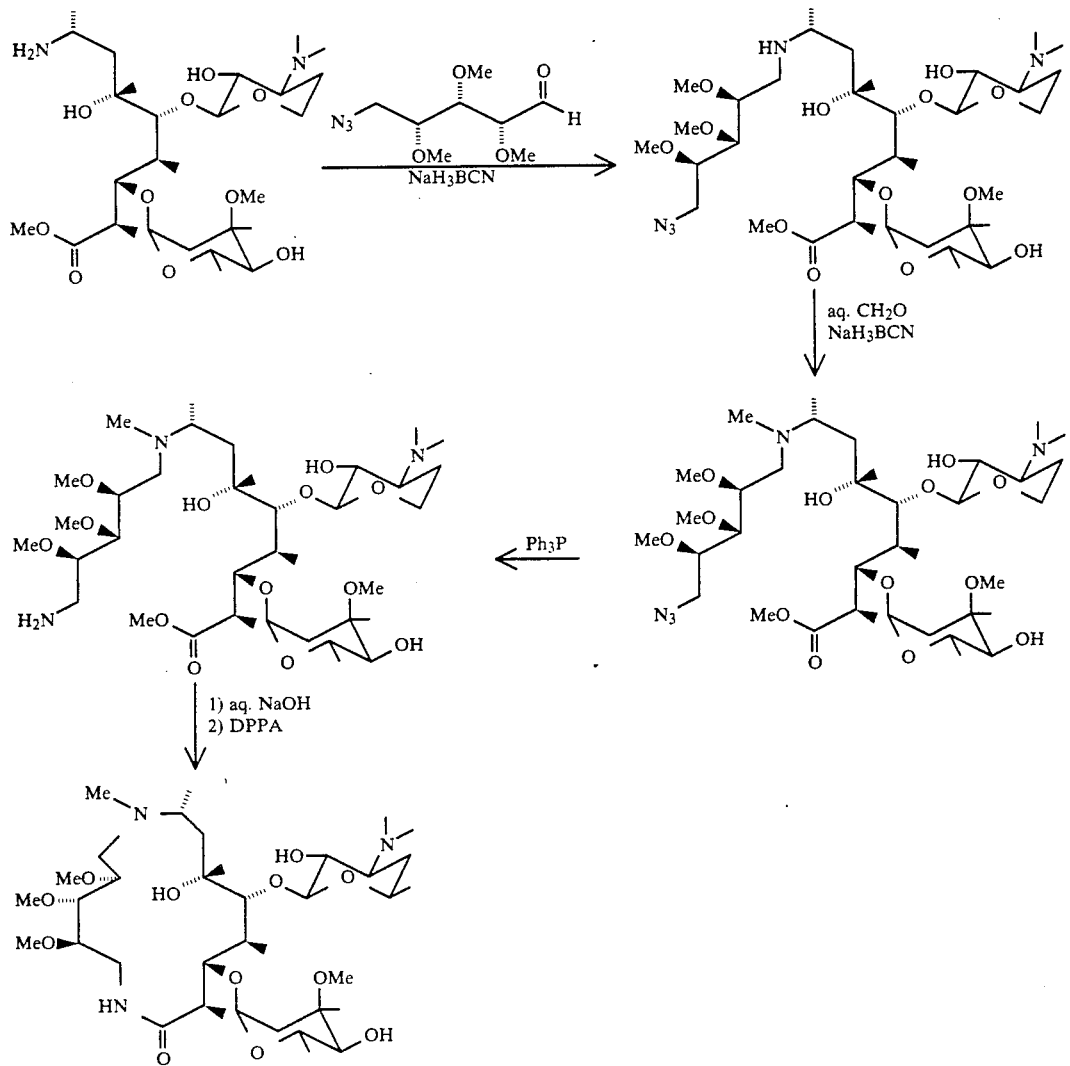

homoerythromycin A, to which was added 2 ml MeOH, 26 mg (0.12 mmol, 1.2 eq.) of the aldehyde starting material, 15 mg NaH₃BCN (0.22 mmol, 2.2 eq.), and 400 μl of AcOH. The reaction was stirred at 60° C. for 24 hours. The solvent was removed under vacuum and the residue was taken up in 94:6:1 $CH_2Cl_2$/MeOH/aq. $NH_3$ and chromatographed on silica gel using the same solvent mixture. This afforded 56 mg (83%) of the desired adduct.

Selected spectral data for 8a-(2-(S),3-(S),4-(S)-trimethoxy-5-azidopentyl)-8a-aza-9,10,11,12,13,14,15-heptanor-8a-homoerythromycin A:

¹H NMR (400 MHz, CDCl₃) δ 4.60 (d, H-1″, J=4.4 Hz), 4.36 (d, H-1′, J=7.3 Hz), 4.10 (dd, H-3, J=2.5, 7.9), 4.00 (m, H-5″), 3.63 (s, COOCH₃), 3.51 (d, H-5, J=2.6), 3.47 (s, OCH₃), 3.44 (s, OCH₃), 3.38 (s, OCH₃), 3.26 (s, OCH₃), 2.95 (br t, H-4″), 2.81 (dq, H-2), 2.50 (m, H-3′), 2.26 (s, N(CH₃)₂), 1.65 (br d, H-4′), 1.29 & 1.18 (singlets, 6-Me and 3″-Me), 1.22 (d, J=6.3 Hz), 1.21 (d, J=6.1 Hz), 1.09 (d, J=7.1 Hz), 1.09 (d, J=7.1 Hz), & 1.07 (d, J=8.1 Hz), (methyl doublets).

IR: 2100 cm⁻¹, 1730 cm⁻¹

FAB MS: 795 (M+H⁺)

Preparation of
8a-methyl-8a-(2-(S),3-(S),4-(S)-trimethoxy-5-azidopentyl)-8a-aza-9,10,11,12,13,14,15-heptanor-8a-homoerythromycin A To a 10 ml round bottom flask was introduced 57 mg (0.071 mmol) of 8a-(2-(S),3-(S),4-(S)-trimethoxy-5-azidopentyl)-8a-aza-9,10,11,12,13,14,15-heptanor-8a-homoerythromycin A, to which was added 2 ml MeOH, 0.15 ml 37% aq. formaldehyde, and 15 mg triphenylphosphine (0.22 mmol, 3 eq.). The reaction was stirred at room temperature for 0.5 hours. The solvent was removed under vacuum and the residue was taken up in 90:10:1 $CH_2Cl_2$/MeOH/aq. $NH_3$ and chromatographed on silica gel using the same solvent mixture. This afforded 52 mg (89%) of the desired adduct.

Selected spectral data for 8a-methyl-8a-(2-(S),3-(S),4-(S)-trimethoxy-5-azidopentyl)-8a-aza-9,10,11,12,13,14,15-heptanor-8a-homoerythromycin A:

¹H NMR (400 MHz, CDCl₃) δ4.61 (d, H-1″), 4.39 (d, H-1′, J=7.3 Hz), 4.09 (dd, H-3, J=2.2, 8.1 ), 4.01 (m, H-5″), 3.63 (s, COOCH₃), 3.53 (d, H-5, J=2.8), 3.49 (s, OCH₃), 3.44 (s, OCH₃), 3.34 (s, OCH₃), 3.26 (s, OCH₃), 3.23 (dd, J=7.3, 10.3, H-2′), 2.96 (d, J=9.5, H-4″), 2.87 (dq, H-2), 2.49 (m, H-3′), 2.28 (s, N(CH₃)₂), 1.64 (br d, H-4′), 1.32 & 1.19 (singlets, 6-Me and 3″-Me), 1.21 (d, J=6.4 Hz), 1.20 (d, J=6.0 Hz), 1.09 (d, J=6.3 Hz), 1.07 (d, J=6.6 Hz), & 0.93 (d, J=6.5 Hz), (methyl doublets).

FAB MS: 808 (M+H⁺)

Preparation of
8a-methyl-8a-(2-(S),3-(S),4-(S)-trimethoxy-5-aminopentyl)-8a-aza-9,10,11,12,13,14,15-heptanor-8a-homoerythromycin A To a 10 ml round bottom flask was introduced 52 mg (0.064 mmol) of 8a-methyl-8a-(2-(S),3-(S),4-(S)-trimethoxy-5-azidopentyl)-8a-aza-9,10,11,12,13,14,15-heptanor-8a-homoerythromycin A, to which was added 1.5 ml THF, 0.060 ml water, and 84 mg triphenylphosphine (0.32 mmol, 5 eq.). The reaction was stirred at 60° C. for 0.5 hours. The solvent was removed under vacuum and the residue was taken up in 90:10:1 $CH_2Cl_2$/MeOH/aq. $NH_3$ and chromatographed on silica gel using the same solvent mixture. This afforded 48 mg (92%) of the desired adduct.

Selected spectral data for 8a-methyl-8a-(2-(S),3-(S),4-(S)-trimethoxy-5-aminopentyl)-8a-aza-9,10,11,12,13,14,15-heptanor-8a-homoerythromycin A:

¹H NMR (400 MHz, CDCl₃) δ 4.59 (d, H-1″, J=4.7 Hz), 4.38 (d, H-1′, J=7.3 Hz), 4.08 (dd, H-3, J=2.2, 8.1 ), 4.01 (m, H-5″), 3.63 (s, COOCH₃), 3.53 (d, H-5, J=2.8), 3.50 (s, OCH₃), 3.41 (s, OCH₃), 3.35 (s, OCH₃), 3.26 (s, OCH₃), 3.23 (dd, J=7.3, 10.3, H-2′), 2.95 (d, J=9.5, H-4″), 2.87 (dq, H-2), 2.49 (m, H-3′), 2.27 (s, N(CH₃)₂), 2.22 (s, 8a-NCH₃), 1.65 (br d, H-4′), 1.31 & 1.18 (singlets, 6-Me and 3″-Me), 1.21 (d, J=6.3 Hz), 1.20 (d, J=6.0 Hz), 1.09 (d, J=6.1 Hz), 1.08 (d, J=6.8 Hz), & 0.93 (d, J=6.5 Hz), (methyl doublets).

FAB MS: 782 (M+H⁺)

Preparation of
8a-methyl-8a-aza-9-deoxo-10-demethyl-10-(S)-methoxy-11-O-methyl-12-O-methyl-12-demethyl-14,15-bisnor-8a-homoerythromycin A lactam To a 50 ml round bottom flask was introduced 48 mg (0.061 mmol) of starting material, to which was added 1.5 ml MeOH, 1.5 ml THF and 0.75 ml 1N aq. NaOH. The reaction was stirred at room temperature and monitored by TLC (93:7:1 $CH_2Cl_2$/MeOH/aq. NH₃, product is baseline). After 24 hours, the reaction was judged to be complete by TLC (only baseline material.) The reaction was added to 50 ml of water and the pH was adjusted to 7.7 with dilute HCl. All solvent was removed under high vacuum and the sample was dried under high vacuum for 24 hours. To the residue was added 6 ml of sieve dried DMF and the reaction was cooled in an ice/salt bath to about −10° C., at which time 100 mg NaHCO₃ and 0.05 ml of diphenylphosphorylazide (63 mg, 0.23 mmol, 3.8 eq.) was added. The reaction was stirred and allowed to warm to room temperature over several hours. After 24 hours, TLC (93:7:1 $CH_2Cl_2$/MeOH/aq. NH₃) of the crude reaction showed no material remaining on the baseline, and formation of a single mid R_f spot. Most of the solvent was removed under high vacuum, and the residue was taken up in 200 ml of methylene chloride and washed three times with water. The organic layer was dried over MgSO₄ and the solvent was removed under high vacuum. The residue was taken up in 94:6:1 $CH_2Cl_2$/MeOH/aq. NH₃ and chromatographed on silica gel using the same solvent mixture. This afforded 26 mg (56% yield) of the desired product.

Selected spectral data for 8a-methyl-8a-aza-9-deoxo-10-demethyl-10-(S)-methoxy-11-O-methyl-12-O-methyl-12-demethyl-14,15-bisnor-8a-homoerythromycin A lactam:

¹H NMR (400 MHz, CDCl₃) δ 4.80 (d, H-1″), 4.32 (d, H-1′), 4.22 (m, H-3), 4.02 (m, H-5″), 3.53 (s, OCH₃), 3.41 (s, OCH₃), 3.32 (s, OCH₃), 3.24 (s, OCH₃), 2.97 (br t, H-4″), 2.87 (dq, H-2), 2.49 (m, H-3′), 2.23 (s, N(CH₃)₂), 1.65 (br d, H-4′), 1.35 & 1.18 (singlets, 6-Me and 3″-Me), 1.28 (d, J=6.4 Hz), 1.17 (d), 1.14 (d), 1.09 (d, J=6.8 Hz), & 0.93 (d, J=6.3 Hz), (methyl doublets).

High resolution FAB MS: 750.5125 (error=0.9 mmu)

Elemental analysis: Calcd for $C_{37}H_{71}N_3O_{12}\cdot1.5H_2O$: C, 57.19; H, 9.60; N, 5.41. Found: C, 57.09,; H, 8.88; N, 5.39.

EXAMPLE 41

General Preparation of 15-Membered Azalactams

Following the procedures given in example 35, 38 & 41, 8a-aza-8a-homo-9,10,11,12,13,14,15-heptanorerythromycin A and various azidoaldehydes (which may be prepared as taught in examples 21-34) are used as starting materials for 15-membered azalactams, as diagrammed below:
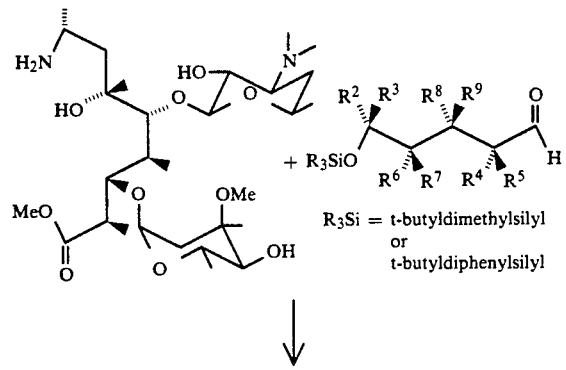
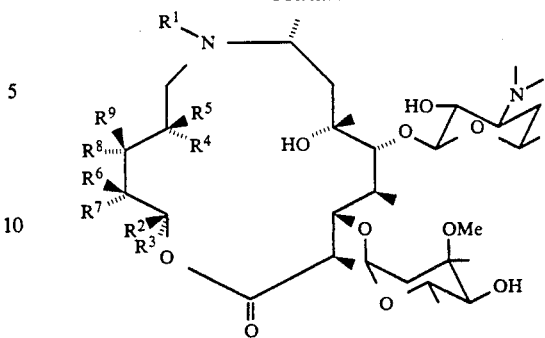
A representative but nonlimiting sampling of the compounds that can be produced in this manner include those in the following table:
TABLE 19-1
| aldehyde (R' = Me, Bn) | macrocycle (R = H or C1 to C7 alkyl or aralkyl) |
|---|---|
|  | 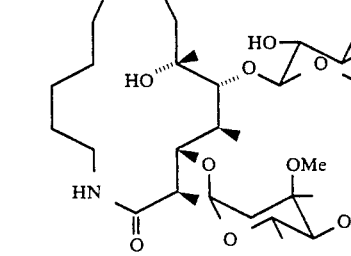 |
|  | 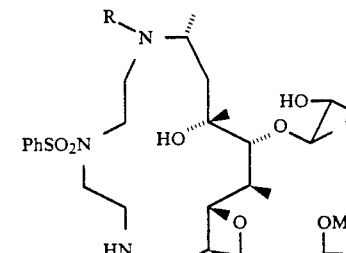 |
|  | 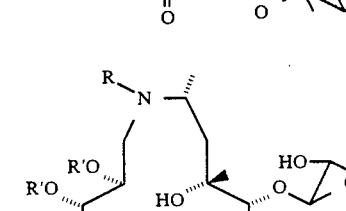 |

TABLE 19-1-continued
| aldehyde (R' = Me, Bn) | macrocycle (R = H or C1 to C7 alkyl or aralkyl) |
|---|---|
| 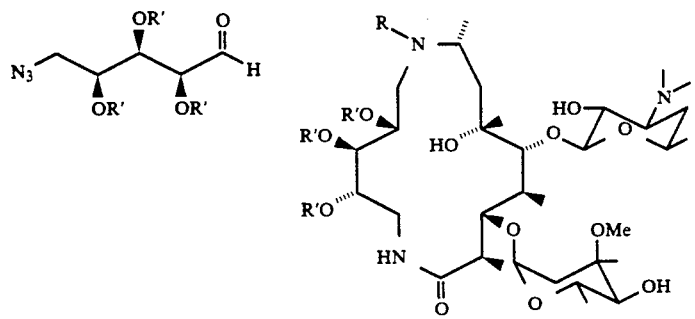 | |
| 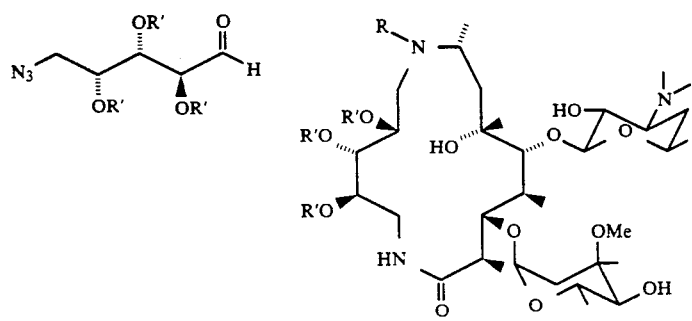 | |
TABLE 19-2
| aldehyde (R' = Me, Bn) | macrocycle (R = H or C1 to C7 alkyl or aralkyl) |
|---|---|
| 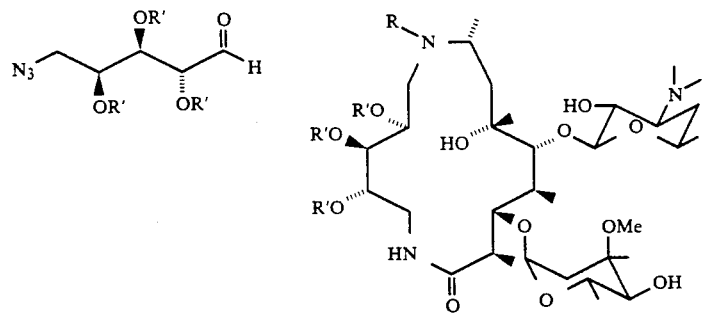 | |
| 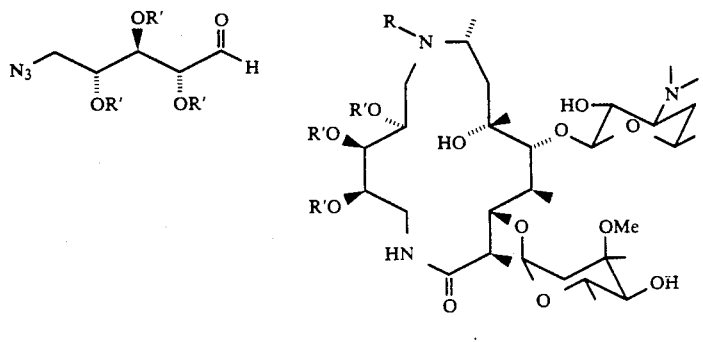 | |

TABLE 19-2-continued
| aldehyde (R' = Me, Bn) | macrocycle (R = H or C1 to C7 alkyl or aralkyl) |
|---|---|
| 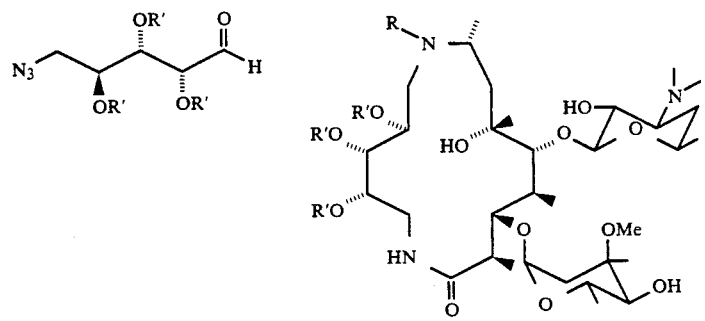 | |
| 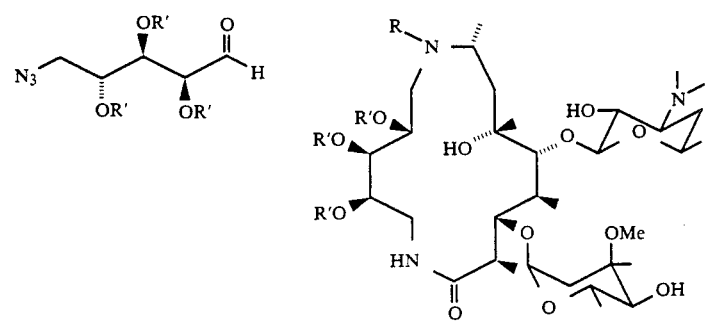 | |
| 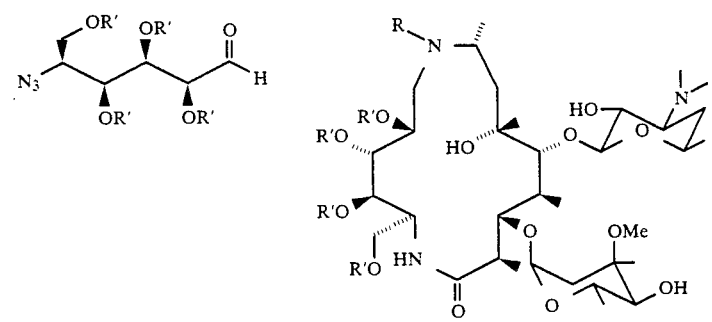 | |
TABLE 19-3
| aldehyde (R' = Me, Bn) | macrocycle (R = H or C1 to C7 alkyl or aralkyl) |
|---|---|
| 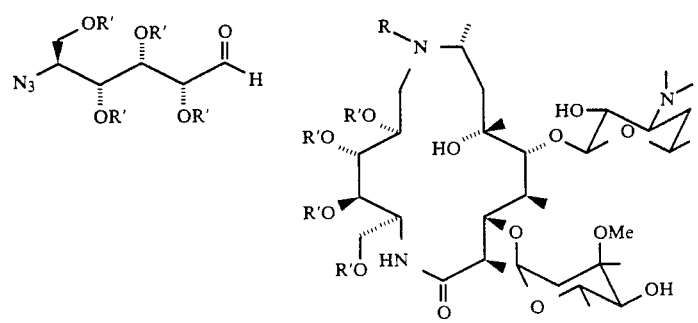 | |

TABLE 19-3-continued
| aldehyde (R' = Me, Bn) | macrocycle (R = H or C1 to C7 alkyl or aralkyl) |
|---|---|
| 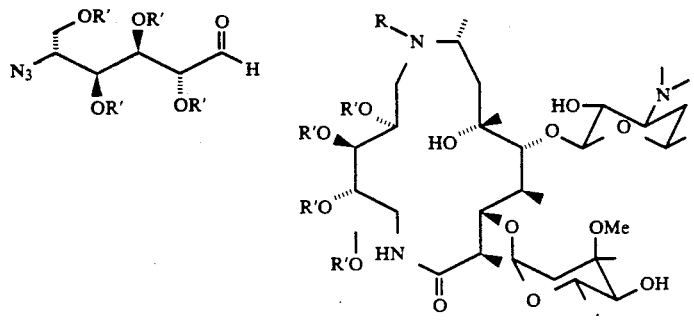 | |
| 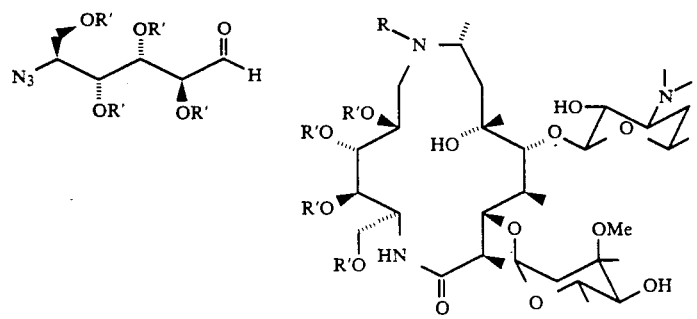 | |
| 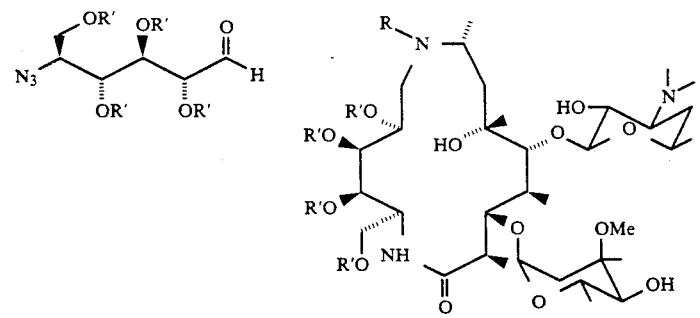 | |
| 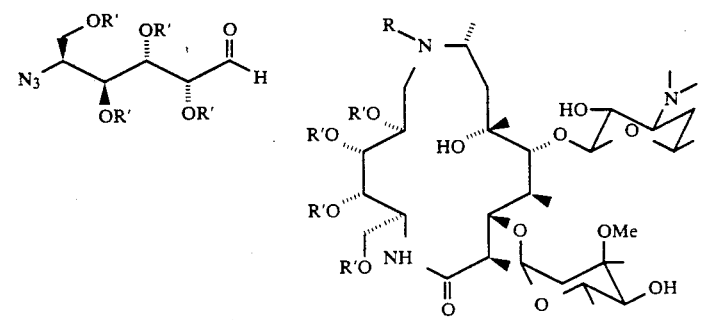 | |

TABLE 19-4

| aldehyde (R' = Me, Bn) | macrocycle (R = H or C1 to C7 alkyl or aralkyl) |
|---|---|

TABLE 19-5
| aldehyde (R' = Me, Bn) | macrocycle (R = H or C1 to C7 alkyl or aralkyl) |
|---|---|
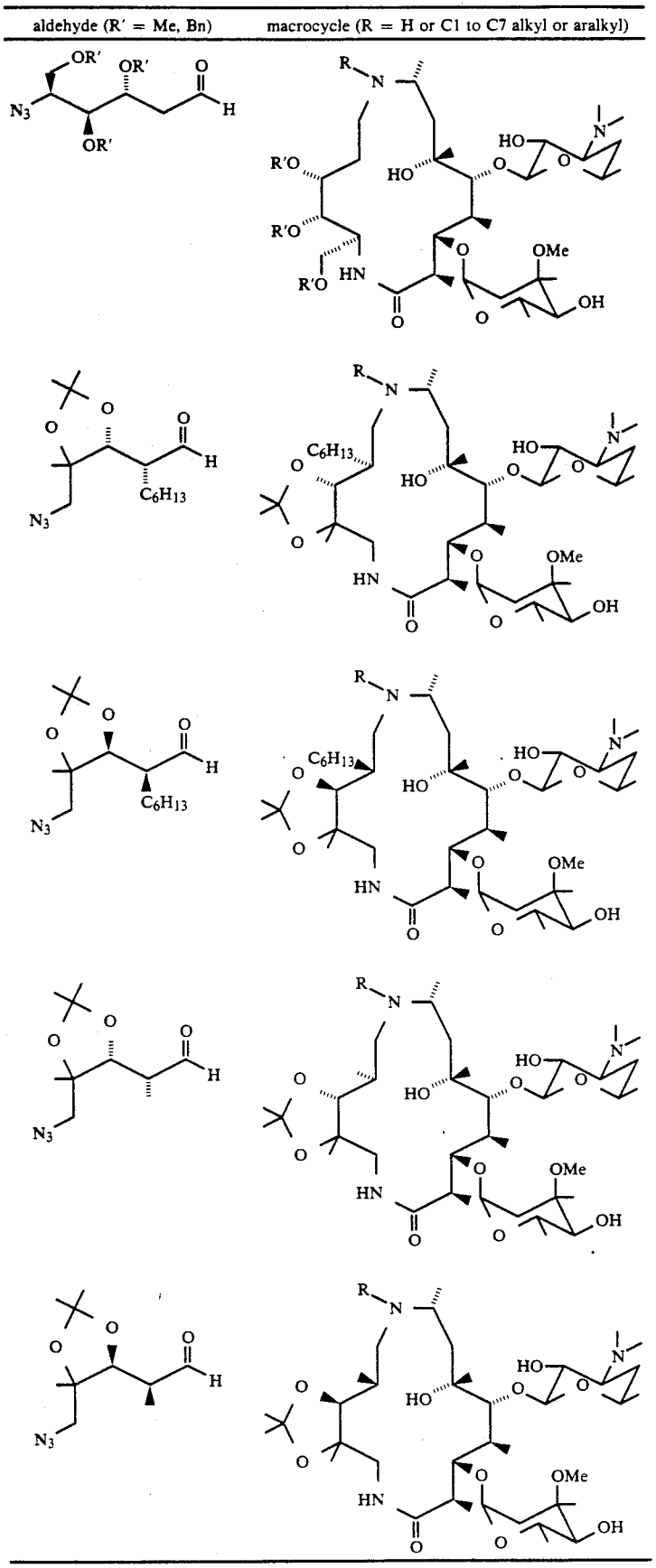

TABLE 19-6
| aldehyde | macrocycle (R = H or C1 to C7 alkyl or aralkyl) |
|---|---|
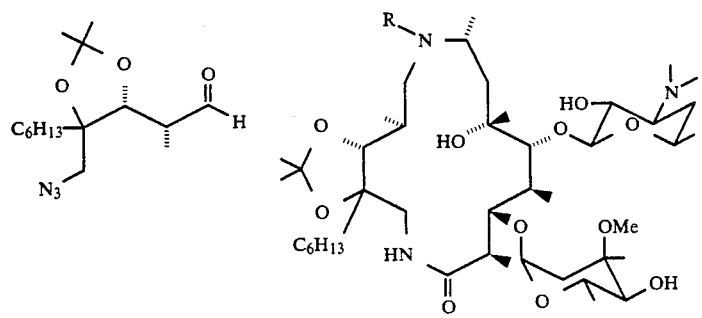
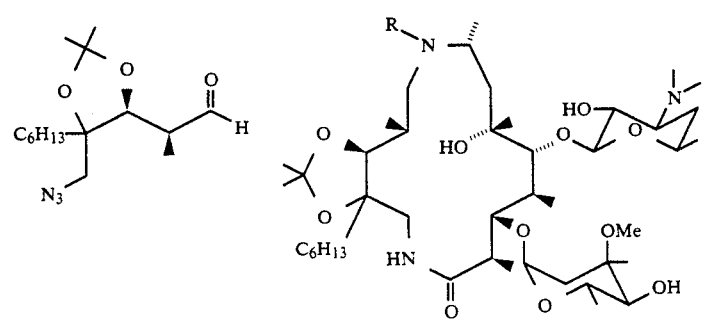
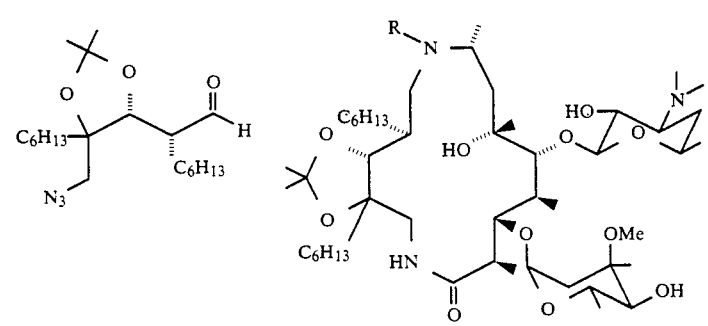
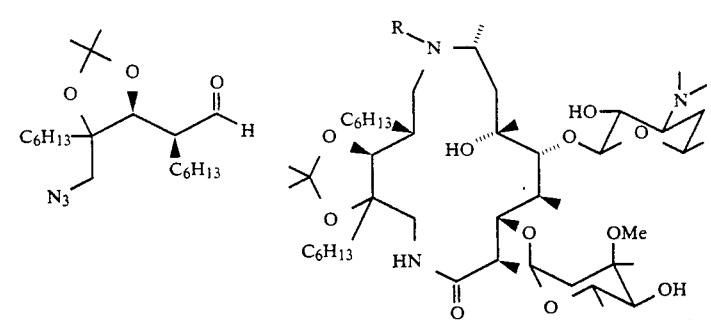
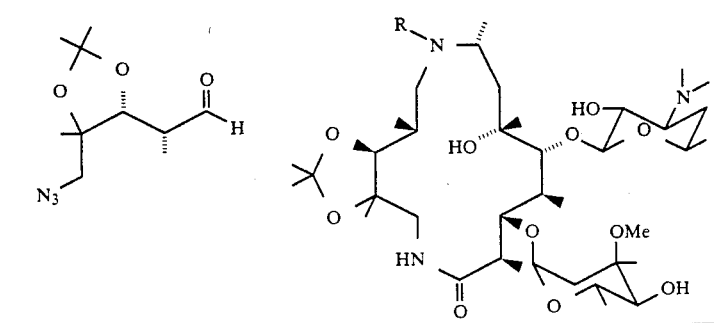

TABLE 19-7

| aldehyde | macrocycle (R = H or C1 to C7 alkyl or aralkyl) |
|---|---|
| | |

TABLE 19-8
| aldehyde | macrocycle (R = H or C1 to C7 alkyl or aralkyl) |
|---|---|
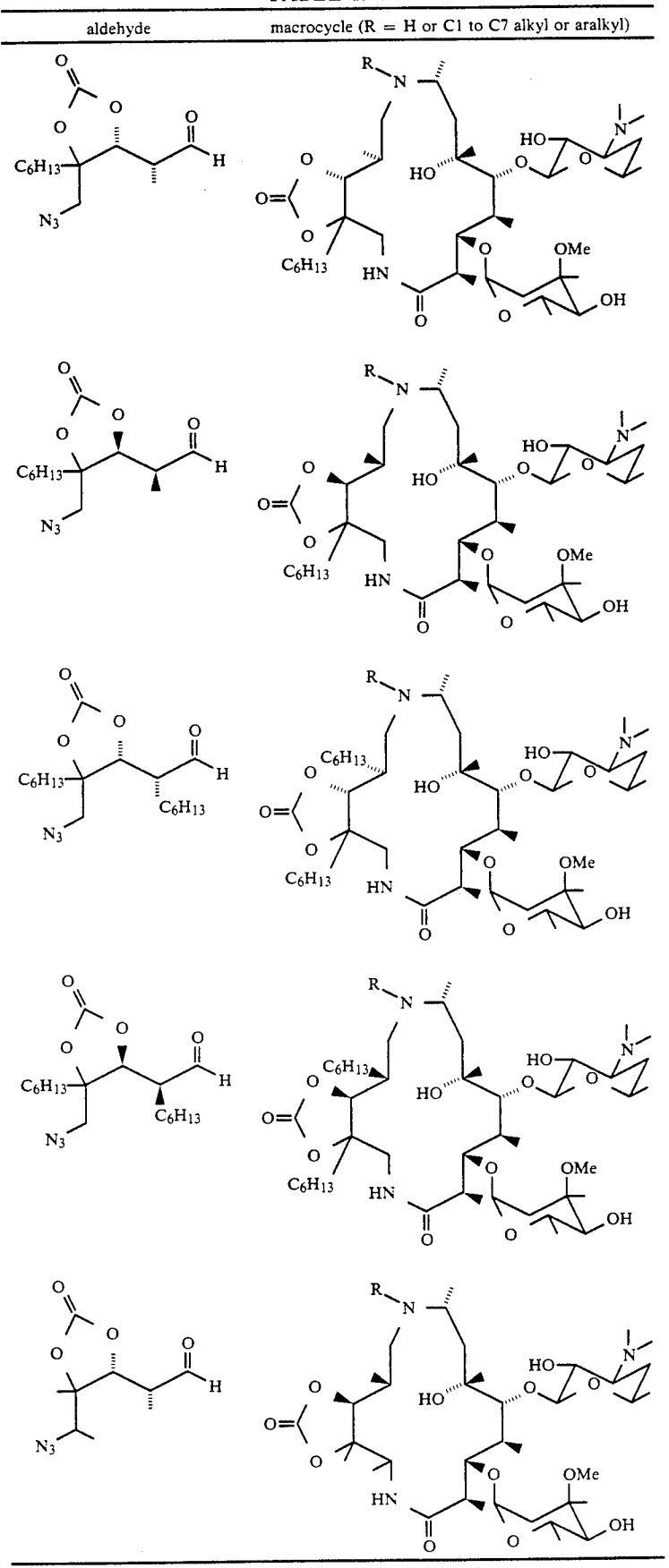

TABLE 19-9
| aldehyde | macrocycle (R = H or C1 to C7 alkyl or aralkyl) |
|---|---|
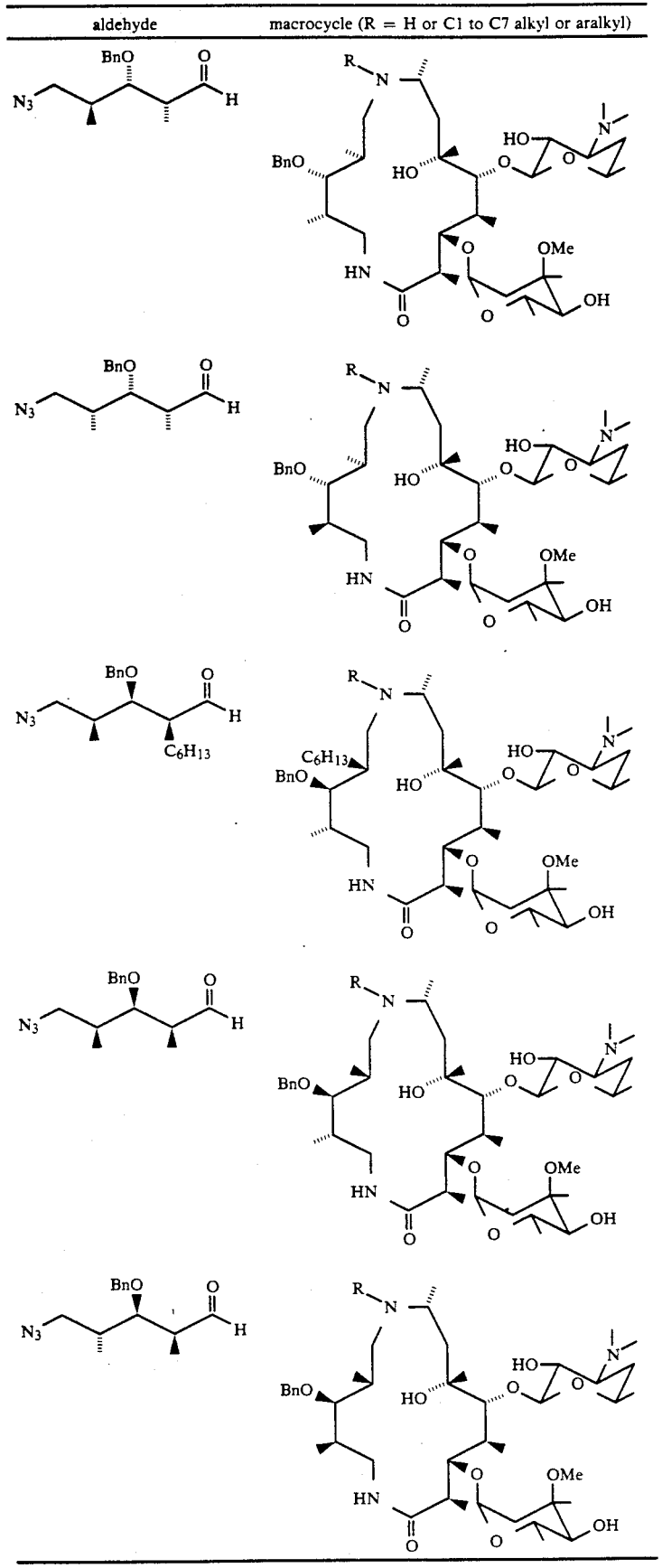

TABLE 19-10
| aldehyde | macrocycle (R = H or C1 to C7 alkyl or aralkyl) |
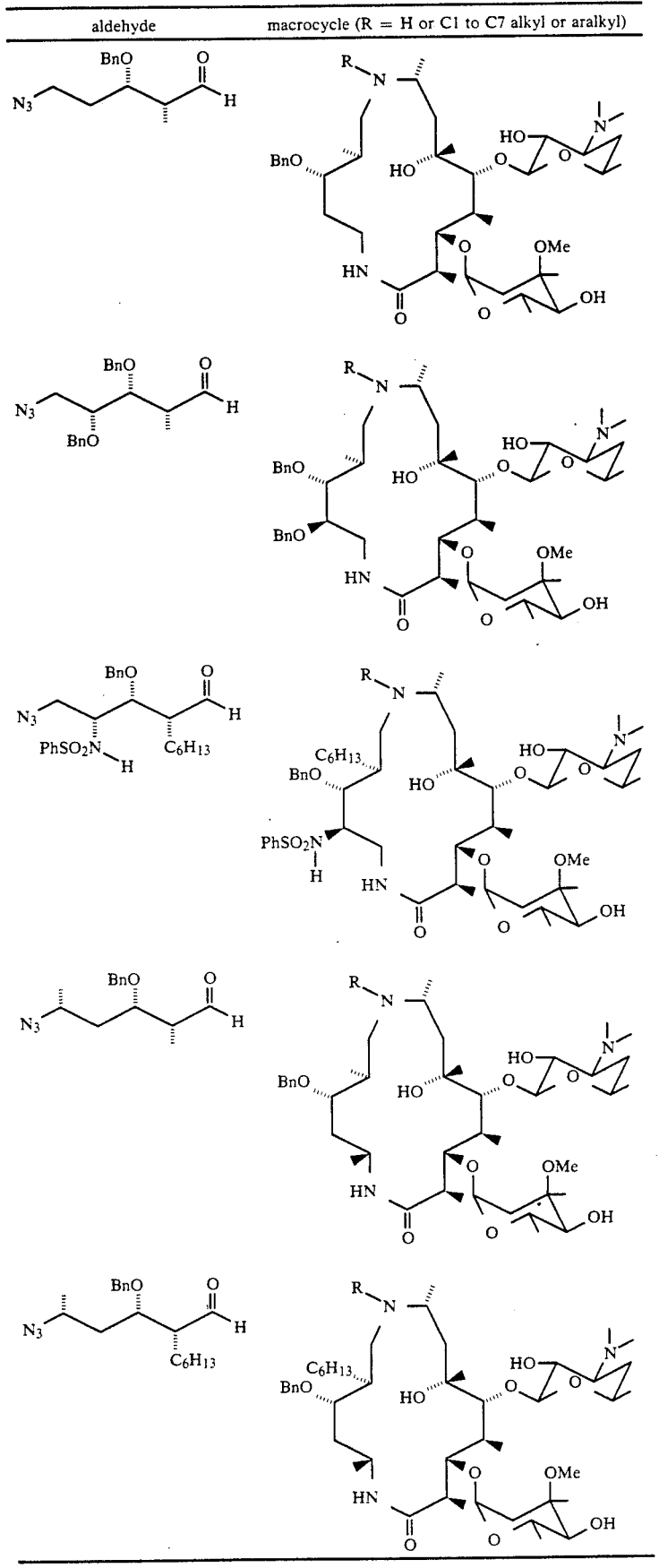

TABLE 19-11
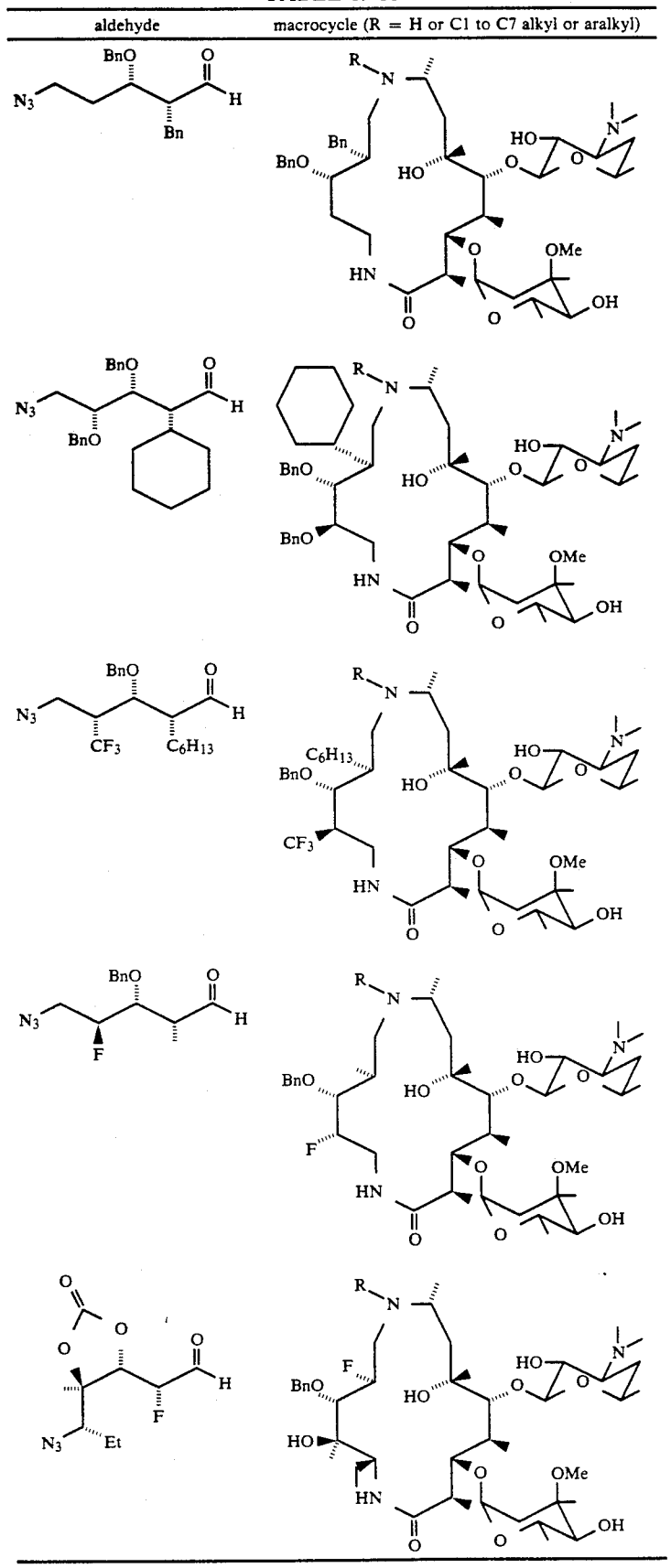
What is claimed is:

cyclizing to form the 8a- or 9a-azalide compound.

2. A process of producing an 8a- or 9a-azalide comprised of: (a) reacting an 8a-aza or 9a-aza fragment of the formula:

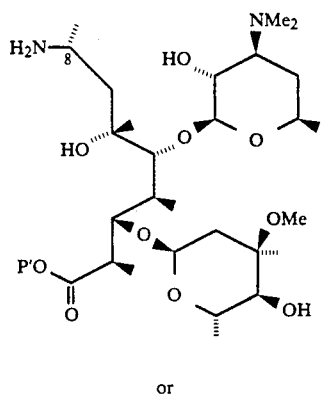

or

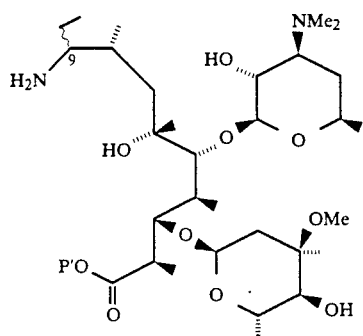

wherein P' is methyl or benzyl, or the carboxylate derivative of said 8a-or 9a-azalide fragment, with a compound of the formula X—A'—Y wherein X and Y are groups reactive with the ester or carboxylate and amine functional groups respectively of the 8a- and 9a-azalide fragments,, and A' is a chain containing three to five carbon atoms, uninterrupted or interrupted by one or two heteroatoms selected from O, S and $NR^1$, wherein $R^1$ represents H, $C_1$ to $C_7$ alkyl, aralkyl or arylsulfonyl, said alkyl, aralkyl and arylsulfonyl being unsubstituted or substituted with fluoro, alkyl or $R^{10}O$, or said chain further being optionally interrupted by a heterocycle, cycloalkyl, aryl or heteroaryl group, said —A'— being unsubstituted or substituted with lower alkyl, hydroxy, halo, alkoxy, amino, aryl, heteroaryl, cycloalkyl, aryloxy, heteroaryloxy, heterocycloalkyl, heterocycloalkoxy, haloalkyl, arylsulfonyl or arylsulfonylamino to form the 8a- or 9a-azalide compound.

3. A process in accordance with claim 2 wherein the compound X—A'—Y is a compound of the formula:

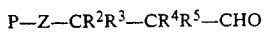

in which P represents H or a protecting group, and the azalide produced is a compound of the formula I:

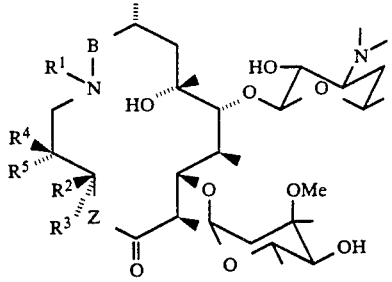

or a pharmaceutically acceptable salt or solvate thereof wherein:
$R^1$ represents hydrogen, $C_1$ to $C_7$ alkyl, aralkyl, or arylsulfonyl, said alkyl, aralkyl and arylsulfonyl groups being unsubstituted or substituted with fluoro, alkyl or $R^{10}O$;
one of $R^2$ and $R^3$ represents hydrogen and the other represents hydrogen, $C_1$ to $C_7$ alkyl, cycloalkyl, aryl or aralkyl, said groups other than hydrogen being unsubstituted or substituted with $R^{10}O$, $R^{11}R^{12}N$, azide, alkyl, cycloalkyl or F;
$R^4$ and $R^5$ are independently hydrogen, $C_1$ to $C_7$ alkyl, fluoroalkyl, cycloalkyl, aryl, aralkyl, $R^{10}O$, $R^{11}R^{12}N$, azide or F;
$R^{10}$ is hydrogen, $C_1$ to $C_7$ alkyl, fluoroalkyl, cycloalkyl, aryl or aralkyl;
$R^{11}$ is hydrogen, $C_1$ to $C_7$ alkyl, fluoroalkyl, cycloalkyl, aryl or aralkyl;
$R^{12}$ is hydrogen, $C_1$ to $C_7$ alkyl, fluoroalkyl, cycloalkyl, aryl or aralkyl, or arylsulfonyl;
Z represents O or $NR^1$, with $R^1$ as defined above, and
B represents $C^*HCH_2CH_3$, the asymmetric carbon atom * of which is in the (R) or (S) stereoconfiguration, or a bond between the carbon and nitrogen atoms to which B is attached.

4. A process in accordance with claim 2 wherein X—A'—Y represents a compound of the formula:

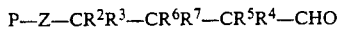

with P representing H or a protecting group, and the azalide produced is a compound represented by the formula II:

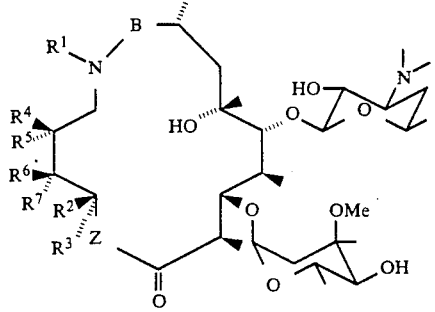

wherein:
$R^1$ represents hydrogen, $C_1$ to $C_7$ alkyl, aralkyl or arylsulfonyl, said alkyl, aralkyl and arylsulfonyl groups being unsubstituted or substituted with fluoro, alkyl or $R^{10}O$;
one of $R^2$ and $R^3$ represents hydrogen and the other represents hydrogen, $C_1$ to $C_7$ alkyl, cycloalkyl, aryl or aralkyl, said groups other than hydrogen being unsubstituted or substituted with $R^{10}O$, $R^{11}R^{12}N$, azide, alkyl, cycloalkyl or F;

$R^4$, $R^5$, $R^6$ and $R^7$ independently represent hydrogen, $C_1$ to $C_7$ alkyl, fluoroalkyl, cycloalkyl, aryl, aralkyl, $R^{10}O$, $R^{11}R^{12}N$, azide or F, or one of the pair $R^4$ and $R^6$, $R^4$ and $R^7$, $R^5$ and $R^6$, and $R^5$ and $R^7$ may be taken to represent cyclic carbonate (—OC(O)O—), cyclic acetonide (OC(CH$_3$)$_2$O), or a $C_1$ to $C_5$ alkanediyl group which forms a ring with the carbon atoms to which they are attached, said alkanediyl group being unsubstituted or substituted with $C_1$ to $C_7$ alkyl, fluoroalkyl, cycloalkyl, aryl, aralkyl, $R^{10}O$, $R^{11}R^{12}N$, azide or F;

$R^{10}$ represents hydrogen, $C_1$ to $C_7$ alkyl, fluoroalkyl, cycloalkyl, aryl or aralkyl;

$R^{11}$ is hydrogen, $C_1$ to $C_7$ alkyl, fluoroalkyl, cycloalkyl, aryl or aralkyl;

$R^{12}$ is hydrogen, $C_1$ to $C_7$ alkyl, fluoroalkyl, cycloalkyl, aryl or aralkyl, or arylsulfonyl;

Z represents O or $NR^1$, and

B represents $C^*HCH_2CH_3$, the asymmetric carbon atom * of which is in the (R) or (S) stereoconfiguration, or a bond between the carbon and nitrogen atoms to which B is attached.

5. A process in accordance with claim 2 wherein X—A′—Y represents a compound of the formula:

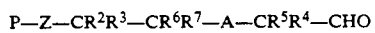

wherein P is H or a protecting group, and the azalide produced is a compound represented by the formula III:

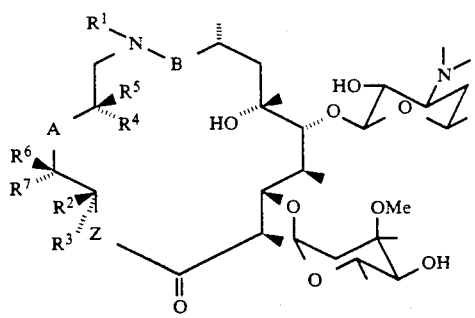

wherein:
$R^1$ represents hydrogen, $C_1$ to $C_7$ alkyl or aralkyl, or arylsulfonyl, said alkyl, aralkyl and arylsulfonyl groups being unsubstituted or substituted with fluoro, alkyl or $R^{10}O$;

one of $R^2$ and $R^3$ represents hydrogen and the other represents hydrogen, $C_1$ to $C_7$ alkyl, cycloalkyl, aryl or aralkyl, said groups other than hydrogen being unsubstituted or substituted with $R^{10}O$, $R^{11}R^{12}N$, azide, alkyl, cycloalkyl or F;

A represents

$R^{12}N$, O or S, (a) when A represents

$R^4$, $R^5$, $R^6$ and $R^7$ independently represent hydrogen, $C_1$ to $C_7$ alkyl, fluoroalkyl, cycloalkyl, aryl, aralkyl, $R^{10}O$, $R^{11}R^{12}N$, azide or F;

$R^8$ and $R^9$ independently represent hydrogen, $C_1$ to $C_7$ alkyl, aralkyl, fluoroalkyl, cycloalkyl, aryl, $R^{11}R^{12}N$, azide or F, and when $R^2$ represents hydrogen, methyl, $C_3$ to $C_7$ alkyl, aralkyl, cycloalkyl or aryl, substituted or unsubstituted as described above, $R^8$ and $R^9$ can also represent $R^{10}O$;

$R^{10}$ is hydrogen, $C_1$ to $C_7$ alkyl, fluoroalkyl, cycloalkyl, aryl, aralkyl, $R^{11}$ is hydrogen, $C_1$ to $C_7$ alkyl, fluoroalkyl, cycloalkyl, aryl or aralkyl;

$R^{12}$ is hydrogen, $C_1$ to $C_7$ alkyl, fluoroalkyl, cycloalkyl, aryl or aralkyl, or arylsulfonyl; or one of the pairs $R^4$ and $R^8$, $R^4$ and $R^9$, $R^5$ and $R^8$, $R^5$ and $R^9$, $R^6$ and $R^8$, $R^6$ and $R^9$, $R^7$ and $R^8$, and $R^7$ and $R^9$ may be taken to represent a cyclic carbonate (—OC(O)O—), cyclic acetonide (—OC(CH$_3$)$_2$O—), or a $C_1$ to $C_5$ alkanediyl group which forms a ring with the carbon atoms to which such group is attached, said alkanediyl group being unsubstituted or substituted with $C_1$ to $C_7$ alkyl, fluoroalkyl, cycloalkyl, aryl, aralkyl, $R^{10}O$, $R^{11}R^{12}N$ or F;

(b) when A represents $R^{12}N$, O or S, $R^4$, $R^5$, $R^6$ and $R^7$ independently represent H, $C_1$ to $C_7$ alkyl, fluoroalkyl, cycloalkyl, aryl or aralkyl;

Z represents O or $NR^1$, and

B represents $C^*HCH_2CH_3$, the asymmetric carbon atom *of which is in the (R) or (S) stereoconfiguration, or a bond between the carbon and nitrogen atoms to which B is attached.

6. A process in accordance with claim 2 wherein the group Y of compound X—A′—Y comprises an aldehyde moiety, which is reacted with the amine of the 8-a or 9a-azalide eastern fragment by reductive amination.

7. A process in accordance with claim 6 in which sodium cyanoborohydride is reacted with the aldehyde function.

8. A process in accordance with claim 2 wherein X is an amino or hydroxy group which is reacted with the ester or carboxylate group of the 8a- or 9a-azalide eastern fragment or derivative thereof, in the presence of base, diisopropyl azodicarboxylate and triphenyl phosphine.

9. A process in accordance with claim 2 wherein X represents an amino group which is reacted with the ester or carboxylate moiety of the 8a- or 9a-azalide eastern fragment or derivative thereof, in the presence of base and diphenylphosphorylazide.

* * * * *

UNITED STATES PATENT AND TRADEMARK OFFICE
CERTIFICATE OF CORRECTION

PATENT NO. : 5,332,807
DATED : July 26, 1994
INVENTOR(S) : Sherman T. Waddell et al It is certified that error appears in the above-indentified patent and that said Letters Patent is hereby corrected as shown below:

Column 151, line 1, claim 1 should read:

1. A process of producing an 8a- or 9a- azalide compound comprising reacting an 8a- or 9a- azalide eastern fragment or a derivative thereof with a compound of the formula: X-A'-Y wherein X and Y are appropriate reactive groups and A' is a compound which forms the western portion of the azalide, and cyclizing to form the 8a- or 9a- azalide compound.

Signed and Sealed this

Fourth Day of October, 1994

Attest:

BRUCE LEHMAN

Attesting Officer

Commissioner of Patents and Trademarks